(12) United States Patent
Stone

(10) Patent No.: US 9,289,192 B2
(45) Date of Patent: Mar. 22, 2016

(54) BIOPSY NEEDLE ACTUATOR ASSEMBLY

(71) Applicant: 3DBiopsy LLC, Vail, CO (US)

(72) Inventor: Nelson N. Stone, Vail, CO (US)

(73) Assignee: 3DBiopsy LLC, Vail, CO (US)

( * ) Notice: Subject to any disclaimer, the term of this patent is extended or adjusted under 35 U.S.C. 154(b) by 0 days.

(21) Appl. No.: 14/634,679

(22) Filed: Feb. 27, 2015

(65) Prior Publication Data

US 2015/0245825 A1 Sep. 3, 2015

Related U.S. Application Data

(60) Provisional application No. 61/946,366, filed on Feb. 28, 2014.

(51) Int. Cl.
| | |
|---|---|
| *A61B 10/00* | (2006.01) |
| *A61B 10/02* | (2006.01) |
| *A61B 8/08* | (2006.01) |
| *A61B 8/00* | (2006.01) |
| *A61B 19/00* | (2006.01) |

(52) U.S. Cl.
CPC .............. *A61B 10/0241* (2013.01); *A61B 8/463* (2013.01); *A61B 8/483* (2013.01); *A61B 10/02* (2013.01); *A61B 19/54* (2013.01); *A61B 2010/0208* (2013.01); *A61B 2019/545* (2013.01)

(58) Field of Classification Search
CPC ........... A61B 10/0275; A61B 10/0096; A61B 10/0283; A61B 2010/0225; A61B 2010/0208
See application file for complete search history.

(56) References Cited

U.S. PATENT DOCUMENTS

| | | | |
|---|---|---|---|
| 3,929,123 A | 12/1975 | Jamshidi | |
| 4,600,014 A | 7/1986 | Beraha | |
| 4,654,701 A | 3/1987 | Yabe | |
| 4,733,661 A * | 3/1988 | Palestrant | 606/108 |
| 5,031,634 A | 7/1991 | Simon | |
| 5,040,542 A | 8/1991 | Gray | |
| 5,127,537 A | 7/1992 | Graham | |
| D338,965 S | 8/1993 | Glanz et al. | |

(Continued)

FOREIGN PATENT DOCUMENTS

| | | |
|---|---|---|
| WO | WO8905608 | 6/1989 |
| WO | WO2014081908 | 5/2014 |
| WO | WO2014091502 | 6/2014 |

OTHER PUBLICATIONS

"Patents; Patent Application Titled 'Adjustable-Throw Biopsy Needle' Under Review"; Politics & Government Week; Oct. 18, 2012; p. 5872; ProQuest LLC; Atlanta, GA, USA; http://search.proquest.com/professional/docreview/1112854497?accountid=157282.

(Continued)

*Primary Examiner* — Rene Towa
(74) *Attorney, Agent, or Firm* — Spencer Fane LLP

(57) ABSTRACT

A biopsy needle actuator assembly used with a biopsy needle for excising a tissue specimen from a target tissue in an animal includes a counter assembly for tracking the individual biopsy event associated with the actuator assembly, and tracking the cumulative number of firings of the actuator assembly to ensure the actuator assembly is replaced prior to failure. The counter assembly registers movement of the biopsy needle during use, aids an operator in proper identification of the biopsy specimen during a biopsy event, and aids the user in correlating the location and orientation of pathological findings of the biopsy specimen in the target tissue in vivo to aid in treatment of the target tissue.

15 Claims, 82 Drawing Sheets

(56) References Cited

U.S. PATENT DOCUMENTS

| | | | |
|---|---|---|---|
| 5,301,684 A | 4/1994 | Ogirala | |
| 5,335,672 A | 8/1994 | Bennett | |
| 5,358,692 A | 10/1994 | Reynolds | |
| 5,383,466 A | 1/1995 | Partika | |
| 5,477,862 A | 12/1995 | Haaga | |
| 5,492,130 A | 2/1996 | Chiou | |
| 5,494,039 A | 2/1996 | Onik et al. | |
| 5,526,821 A | 6/1996 | Jamshidi | |
| 5,546,957 A | 8/1996 | Heske | |
| 5,549,112 A | 8/1996 | Cockburn et al. | |
| 5,752,923 A | 5/1998 | Terwilliger | |
| 5,820,554 A | 10/1998 | Davis et al. | |
| 5,916,175 A | 6/1999 | Bauer | |
| 6,017,476 A | 1/2000 | Renshaw | |
| 6,258,327 B1 | 7/2001 | Tatum | |
| 6,432,064 B1 | 8/2002 | Hibner | |
| 6,464,648 B1 | 10/2002 | Nakamura | |
| 6,749,576 B2 | 6/2004 | Bauer | |
| 6,860,856 B2 | 3/2005 | Ward | |
| 6,899,850 B2 | 5/2005 | Hayward et al. | |
| 7,831,293 B2 | 11/2010 | Ellis | |
| 8,139,831 B2 | 3/2012 | Khamene et al. | |
| 8,163,252 B2 | 4/2012 | Booker et al. | |
| 8,197,419 B2 | 6/2012 | Field et al. | |
| 8,343,072 B2 | 1/2013 | Bacon et al. | |
| 8,447,384 B2 | 5/2013 | Xu et al. | |
| 8,500,654 B2 | 8/2013 | Goldenberg | |
| 8,501,435 B2 | 8/2013 | Gustafsson et al. | |
| 8,506,504 B2 | 8/2013 | Field et al. | |
| 8,548,562 B2 | 10/2013 | Trachtenberg et al. | |
| 8,562,542 B2 | 10/2013 | Binette et al. | |
| 8,666,128 B2 | 3/2014 | Chaney et al. | |
| 8,741,232 B2 | 6/2014 | Baysal et al. | |
| 8,774,901 B2 | 7/2014 | Velusamy et al. | |
| 8,787,651 B2 | 7/2014 | Potts et al. | |
| 8,788,019 B2 | 7/2014 | Downey et al. | |
| 8,900,147 B2 | 12/2014 | Yoo et al. | |
| 8,915,855 B2 | 12/2014 | Lee | |
| 2003/0135119 A1 | 7/2003 | Lee | |
| 2004/0249307 A1* | 12/2004 | Thompson et al. | 600/568 |
| 2005/0090765 A1 | 4/2005 | Fisher | |
| 2005/0159676 A1 | 7/2005 | Taylor et al. | |
| 2006/0064031 A1 | 3/2006 | Miller | |
| 2007/0116612 A1 | 5/2007 | Williamson, IV | |
| 2008/0175760 A1 | 7/2008 | Justin et al. | |
| 2009/0143698 A1 | 6/2009 | Janssens | |
| 2010/0160826 A1* | 6/2010 | Parihar | 600/567 |
| 2011/0009748 A1 | 1/2011 | Greene et al. | |
| 2011/0105946 A1* | 5/2011 | Sorensen et al. | 600/567 |
| 2011/0224574 A1 | 9/2011 | Sadler et al. | |
| 2011/0313288 A1 | 12/2011 | Chi Sing et al. | |
| 2012/0010511 A1 | 1/2012 | O'Laughlin | |
| 2012/0071749 A1 | 3/2012 | Xu et al. | |
| 2012/0087557 A1 | 4/2012 | Miller et al. | |
| 2012/0150067 A1 | 6/2012 | Booker et al. | |
| 2012/0179065 A1 | 7/2012 | Ferree et al. | |
| 2012/0206448 A1 | 8/2012 | Embrey | |
| 2012/0253228 A1 | 10/2012 | Schembre et al. | |
| 2012/0253230 A1 | 10/2012 | Williams et al. | |
| 2013/0006144 A1 | 1/2013 | Clancy et al. | |
| 2013/0018509 A1 | 1/2013 | Korus | |
| 2013/0108523 A1 | 5/2013 | Tawfik et al. | |
| 2013/0131547 A1 | 5/2013 | Hardert et al. | |
| 2013/0222444 A1 | 8/2013 | Cummins et al. | |
| 2013/0310680 A1 | 11/2013 | Werahera et al. | |
| 2014/0039343 A1 | 2/2014 | Mescher et al. | |
| 2014/0113328 A1 | 4/2014 | Williamson, IV | |
| 2014/0233826 A1 | 8/2014 | Agaian et al. | |
| 2014/0257136 A1 | 9/2014 | Leahy et al. | |

OTHER PUBLICATIONS

Prostate Cancer; Information from Prostate Needle Biopsy Reports Surveyed; Medical Devices & Surgical Technology Week (Feb. 26, 2006) p. 463; Publisher NewsRx, Atlanta, GA, USA; Feb. 26, 2006; http://search.proquest.com/professional/docview/206956168?accountid=157282.

H. Ho; J.S.P. Yuen; P. Mohan, E.W. Lim; and D.W.S. Cheng; "Robotic Transperineal Prostate Biopsy: Pilot Clinical Study"; Elsevier Inc., Urology 78 (5), 2011; pp. 1203-1208.

International Search Report and Written Opinion dated Jun. 5, 2015 in PCT/US2015/018199, filed Feb. 27, 2015, 14 pages.

* cited by examiner

OF 240,000 NEW CASES 63,000 AS AND FT~50%

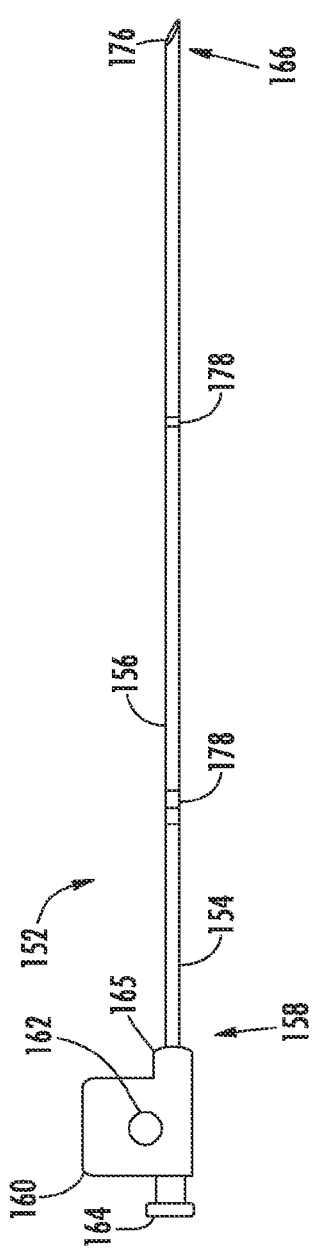
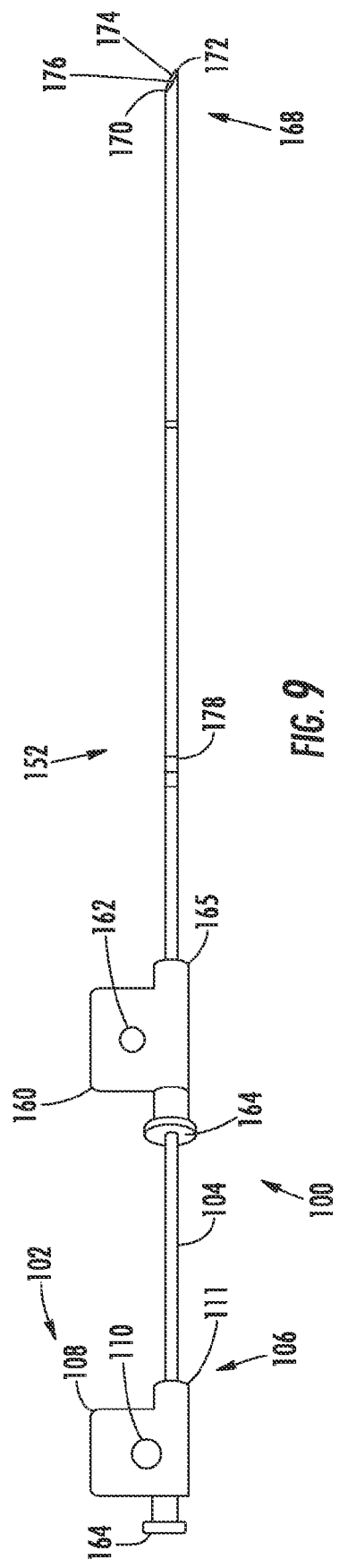
FIG. 8
FIG. 9

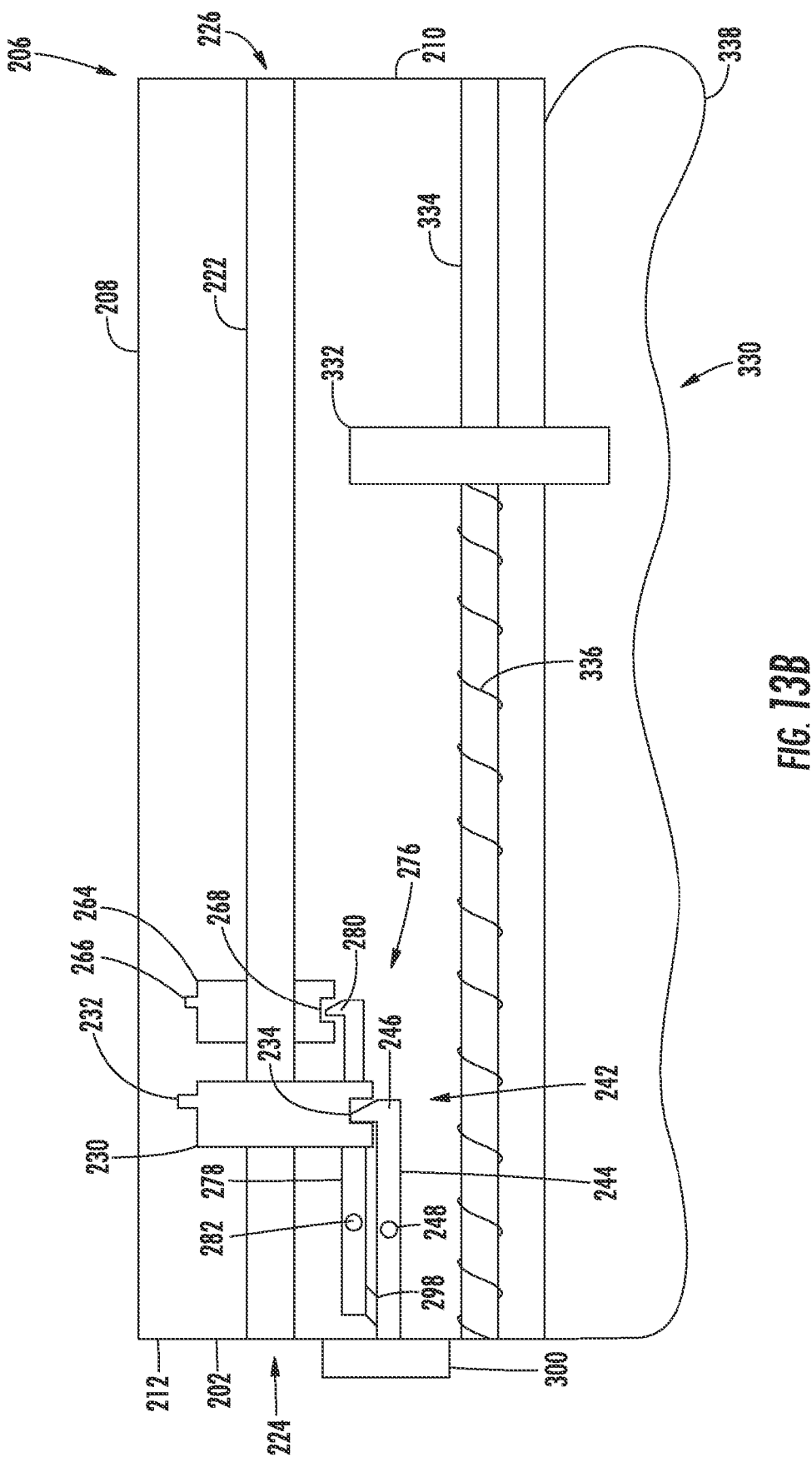

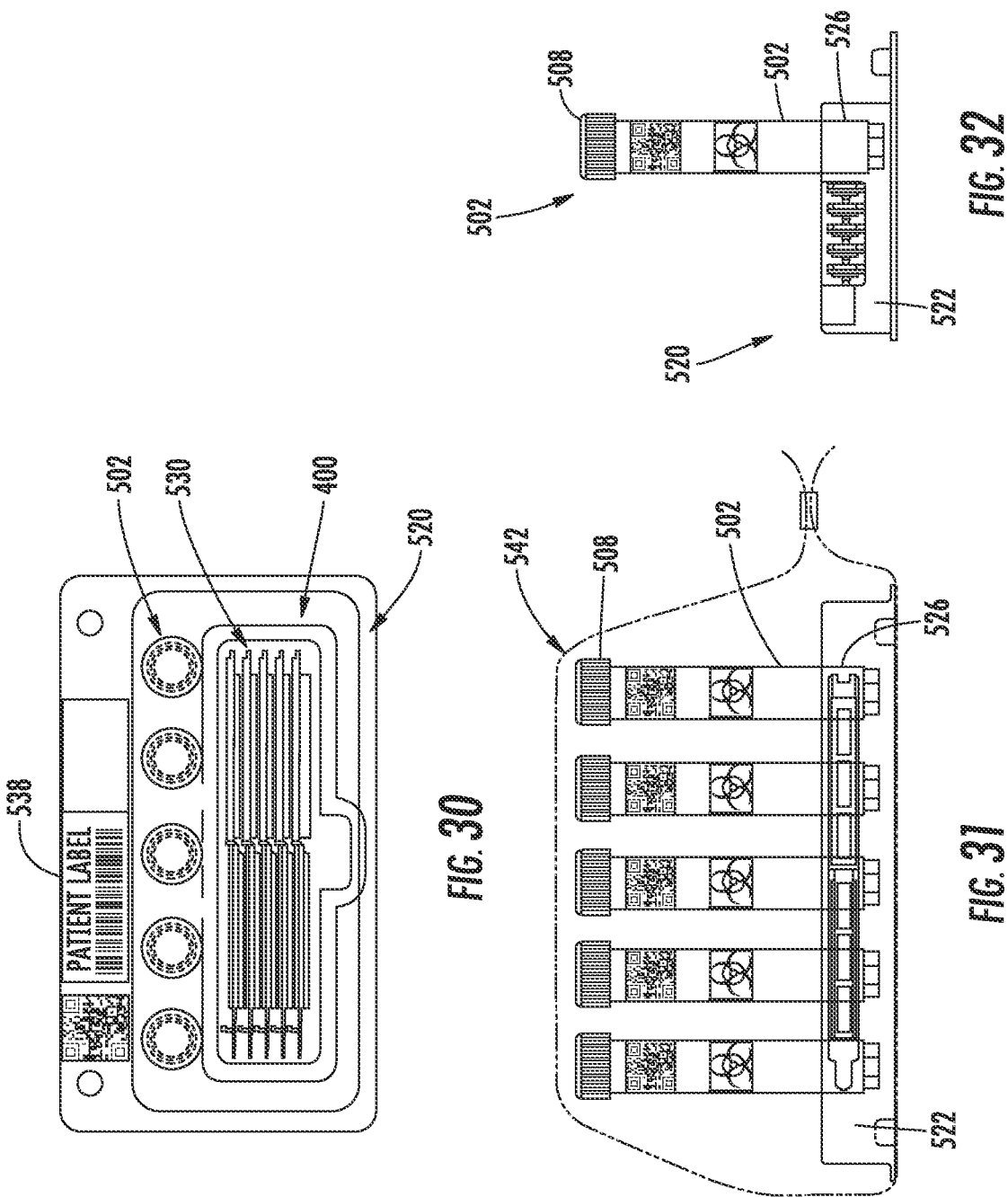

BIOPSY NEEDLE ACTUATOR ASSEMBLY

CROSS-REFERENCE TO RELATED APPLICATIONS

This application claims the benefit of U.S. Provisional Application No. 61/946,366, filed Feb. 28, 2014, the contents of which are hereby incorporated by reference.

BACKGROUND

The present disclosed subject matter relates generally to a transperineal prostate needle biopsy system and method, and more particularly to a biopsy needle used in conjunction with imaging and planning software to identify and treat lesions of the prostate.

Prostate cancer is the most frequently diagnosed solid tumor in men and second leading cause of cancer death in the United States. Early detection and treatment of such tumors has progressively decreased the age-adjusted death rates. A diagnosis of a prostate tumor may be confirmed by a biopsy and assessment of the suspect tissue.

The standard biopsy needle used to confirm a diagnosis of prostate cancer consists of a fixed length core bed. Such a needle, and similar devices, are designed to be used in conjunction with a transrectal ultrasound probe allowing real time imaging of the prostate gland as biopsies are being performed. When transrectal ultrasound was originally introduced large prostate cancer lesions were easily identifiable by ultrasound imaging allowing an operator to see a representative image of the prostate and lesions at the time of biopsy. The wide application of prostate specific antigen (PSA) screening has allowed for the detection of smaller and smaller prostate cancer lesions thereby making visualization of such discrete lesions unlikely when using ultrasound alone. Today, the typical patient presents with an elevated PSA and no discernible lesion on physical exam or by ultrasound exam.

During a typical needle biopsy procedure a urologist uses a traditional transrectal ultrasound-guided approach taking multiple individual biopsies trying to sample the lateral regions of the gland in what amounts to a semi "blind" approach. A patient undergoing this type of procedure has a 20-30% chance of having a cancer diagnosed. A majority of these cancers are low grade. With 240,000 new cases of prostate cancer expected in the United States in 2013, over 75% will be considered low risk cancers meaning these cancers have a low likelihood of being the principle cause of a patient's death. However, biopsy specimens retrieved using the blind approach often leads to inconclusive results. For example, in 50-75% of the situations when a transrectal biopsy is followed by a radical prostatectomy (removal of the entire prostate gland) the pathology predicted by the biopsy is not representative of the final specimen.

Data from radical prostatectomy specimens demonstrates a high likelihood of bilateral and multifocal disease. In a study of 2,388 specimens, the incidence of multifocal lesions ranged from 33%-87% (average 67.6% for 12 studies). Of the more than 180,000 new prostate cancer diagnoses that are found to be low risk on biopsy today, only a third would meet the criteria for observation (no active treatment). The other two-thirds would be candidates for complete or focal (partial) therapy. Identifying these candidates based on transrectal biopsy is extraordinarily difficult, if not impossible. In a study 538 low-risk prostatectomy specimens were examined with the goal of looking for pretreatment characteristics to accurately identify patients for focal therapy. A total of 6 to 16 cores were taken by transrectal biopsy and the median number of positive cores was 1 (range, 1-12). When the prostatectomy specimens were examined, upgrading to Gleason Score (GS) 8-10 occurred in 6.3%. Extracapsular extension was found in 19% and seminal vesicle involvement in 2.4%. Although unilateral disease was found by biopsy in 71% of the patients, it was present in only 22.5% of the prostatectomy specimens.

Based on current data, if accurate prostate biopsies could be performed, a treatment algorithm for an estimated 240,000 new prostate cancer cases (United States) as diagnosed by current biopsy procedures would yield approximately 210,00 candidates with a low grade lesion (GS 6-7) who would be candidates for transperineal mapping (TPM) biopsies and approximately 30,000 candidates with higher grade lesions (GS 8-10) who would be candidates for a radical prostatectomy (RP) or radiotherapy (RT) (FIG. 1). Of the approximately 210,000 candidates undergoing TPM for further examination, approximately 20,000 would yield high grade lesions (GS 8-10) who would be candidates for RP or RT (FIG. 2). Of the remaining approximately 190,000 having undergone TPM, approximately 33 percent would warrant active surveillance (AS), approximately 33 percent would warrant RP or RT, and approximately 33 percent would warrant focal therapy. With improved tools and technology a larger number of candidates could avoid RP or RT.

SUMMARY

A biopsy needle assembly for excising a tissue specimen from a target tissue in an animal includes a mandrel with a core bed with an inner surface forming a projection for marking the tissue specimen at excision. The mandrel has a body extending longitudinally between a proximal end and a distal end about a longitudinally-extending central axis. The body forms a core bed adjacent the distal end for containing the tissue specimen, the core bed having an inner surface extending longitudinally between a first a first end and a second end, and laterally between a first longitudinal edge and an opposing second longitudinal edge.

In an embodiment, the projection is one or more adjacent longitudinal ridges extending between the first longitudinal edge and the second longitudinal edge. In an embodiment, the projections present a contact surface for marking the tissue specimen. In an embodiment, the contact surface includes a marking agent for marking the tissue specimen. In an embodiment, the inner surface defines an upwardly open lower cavity providing additional room for containing the tissue specimen, with the first longitudinal edge and second longitudinal edge forming the upper edges of the lower cavity. In an embodiment, the upwardly open cavity has a C-shaped cross sectional configuration. In an embodiment, the upwardly open cavity has a box-shaped cross sectional configuration. In an embodiment, the first and second longitudinal edges are disposed at a horizontal plane coincident with the central axis, and the bottom of the lower cavity is disposed below the central axis. In an embodiment, the first and second longitudinal edges are disposed above the horizontal plane, and the bottom of the lower cavity is disposed below the central axis. In an embodiment, the first end of the core bed forms a projection extending into the cavity presenting a contact surface for marking the distal end of the tissue specimen. In an embodiment, the marking left on the tissue specimen by the projection aids a pathologist in proper identification of the biopsy specimen during pathological examination, and aid the pathologist in correlating the location and orientation of the findings from the biopsy specimen in the target tissue in vivo to aid in treatment of the target tissue.

A biopsy needle actuator assembly used with a biopsy needle for excising a tissue specimen from a target tissue in an animal includes a counter assembly for tracking the individual biopsy event associated with the actuator assembly, and tracking the cumulative number of firings of the actuator assembly to ensure the actuator assembly is replaced prior to failure. The actuator assembly includes a counter assembly that registers movement of the biopsy needle during use.

In an embodiment, the counter assembly registers movement of the biopsy needle between a rest position and a first position, whereby the needle assembly is ready for firing when it is in the first position. In an embodiment, the counter assembly includes a register wheel for registering movement of a biopsy needle, where the register wheel is operably connected to an index wheel for recording the movement of the biopsy needle. In an embodiment, the index wheel includes an event counter for sequentially recording movement of the biopsy needle as it moves from the rest position to the firing position, and a cumulative counter for contemporaneously recording the needle movement. In an embodiment, a user can bypass the event counter. In an embodiment, a mechanical lockout engages when the cumulative counter registers a defined number of movements of the biopsy needle preventing the actuator assembly from being used beyond its useful life. In an embodiment, the counter assembly aids an operator in proper identification of the biopsy specimen during a biopsy event, and aids the user in correlating the location and orientation of pathological findings of the biopsy specimen in the target tissue in vivo to aid in treatment of the target tissue.

A pathology specimen cassette includes a cartridge assembly having a media retained between a base and a lid. A biopsy tissue specimen is applied to the media and retained within the closed cartridge assembly preserving the tissue until it is removed for pathological examination. The base is hingedly connected to the lid. The base forms a cavity with openings in its lower wall. The lid includes a middle wall forming openings. The openings allow fluids to move in and out of the closed cartridge assembly. A fluid transfer element, bound by the media and a semi-permeable membrane, is retained within the cartridge assembly. The fluid transfer element absorbs fluid allowing the tissue specimen on the media to be constantly immersed in the fluid. The media facilitates handling and examination of the tissue specimen without a need to remove the specimen from the media. The cartridge assembly with tissue is put in a collection vial containing a preservative and stored in a collection tray. The tray includes unused cartridge assemblies and vials, and unique markings identifying the patient and specimen locations.

In an embodiment, a tissue specimen is placed on the media where the specimen includes markings made by the projections on a biopsy needle aiding a pathologist in proper identification of the biopsy specimen during pathological examination, and aiding the pathologist in correlating the location and orientation of the pathological findings from the biopsy specimen in the target tissue in vivo to aid in treatment of the target tissue.

A system, method, and apparatus for planning and performing biopsies on a target tissue located within an animal includes a three-dimensional imaging system for imaging and mapping of a target tissue for the planning and performing biopsies of the target tissue, and for planning and performing treatments of the target tissue.

A three-dimensional biopsy mapping and focal therapy system, method, and apparatus uses an imaging system to: generate and store a three-dimensional image of the target tissue based on an ultrasound image of the target tissue, store a user generated contour of the target tissue and surrounding anatomical structures, and calculate the volume of the target tissue and surrounding anatomical structures; plan the location and orientation of the biopsy sites; generate and store a three-dimensional image of the location, orientation, and volume of tissue biopsied from the target tissue, store a map of diseased tissue based on the three-dimensional image and user inputs of diseased tissue identified by pathological examination. During biopsy planning, the system calculates the recommended number of biopsy sites and biopsy needle core lengths needed, and calculates probabilities for encountering lesions of a particular size. The system generates a visual representation of the location and orientation of the biopsy needles and sites in the three-dimensional target tissue. The system is used to identify and log the biopsies. A pathologist identifies lesions in each biopsy specimen and uses the stored images of the patient target tissue in the system to identify the size and location of the lesion according to each biopsy site. Based on the pathology information and biopsy sites, the volume of the overall tumor is calculated and represented in the three-dimensional image. The three-dimensional image of the target tissue and lesion tissue is used to provide localized therapy to the diseased tissue.

BRIEF DESCRIPTION OF THE DRAWINGS

The drawings constitute a part of this specification and include exemplary embodiments of the disclosed subject matter and illustrate various objects and features thereof.

FIG. 8 is a side elevation view of an embodiment of a cannula.
FIG. 9 is a side elevation view of an embodiment of a needle assembly.
FIG. 13B is a side elevation view of an embodiment of an actuator assembly showing a device cocking mechanism.

FIG. 30 is a plan view of an embodiment of a tray.

FIG. 31 is a front elevation view of an embodiment of a tray.

FIG. 32 is a side elevation view of an embodiment of a tray.

DETAILED DESCRIPTION

As required, detailed aspects of the disclosed subject matter are disclosed herein; however, it is to be understood that the disclosed aspects are merely exemplary of the disclosed subject matter, which may be embodied in various forms. Therefore, specific structural and functional details disclosed herein are not to be interpreted as limiting, but merely as a basis for the claims and as a representative basis for teaching one skilled in the art how to variously employ the disclosed technology in virtually any appropriately detailed structure.

Certain terminology will be used in the following description for convenience in reference only and will not be limiting. For example, up, down, front, back, right and left refer to the disclosed subject matter as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning.

A needle biopsy system includes a biopsy needle assembly used in conjunction with an actuator assembly to remove a tissue specimen from a target tissue, storage of the tissue specimen in a pathology specimen cassette until pathological examination, and a three-dimensional tissue mapping system for planning the biopsy procedure, guiding removal of the tissue specimen, identifying and recording pathological remarks, and conducting targeted tissue treatment. Target tissue may be any animal tissue type or organ, including humans. Tissue types include, but are not limited to, epithelial tissue, connective tissue, muscle tissue, nervous tissue. Organs include, but are not limited to, prostate, breast, kidney, and liver.

Needle Assembly

Figure 1:
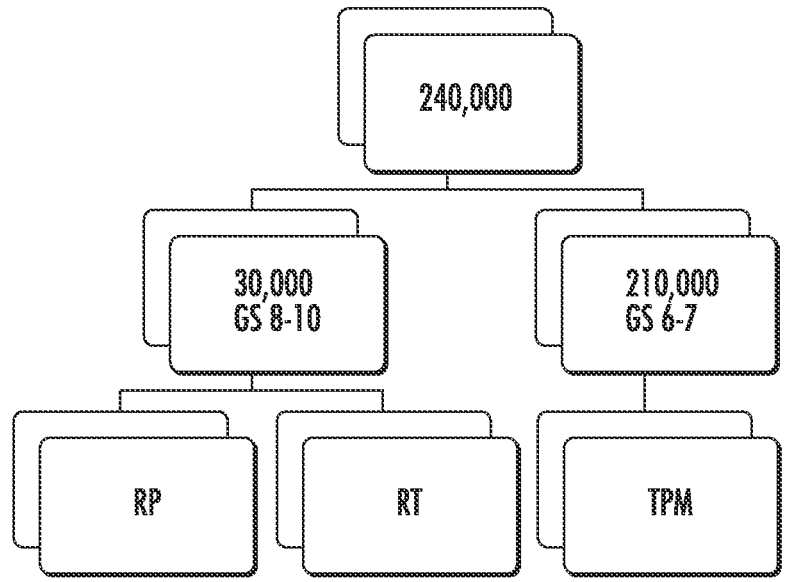
FIG. 1 is a schematic of a treatment algorithm.
Figure 2:
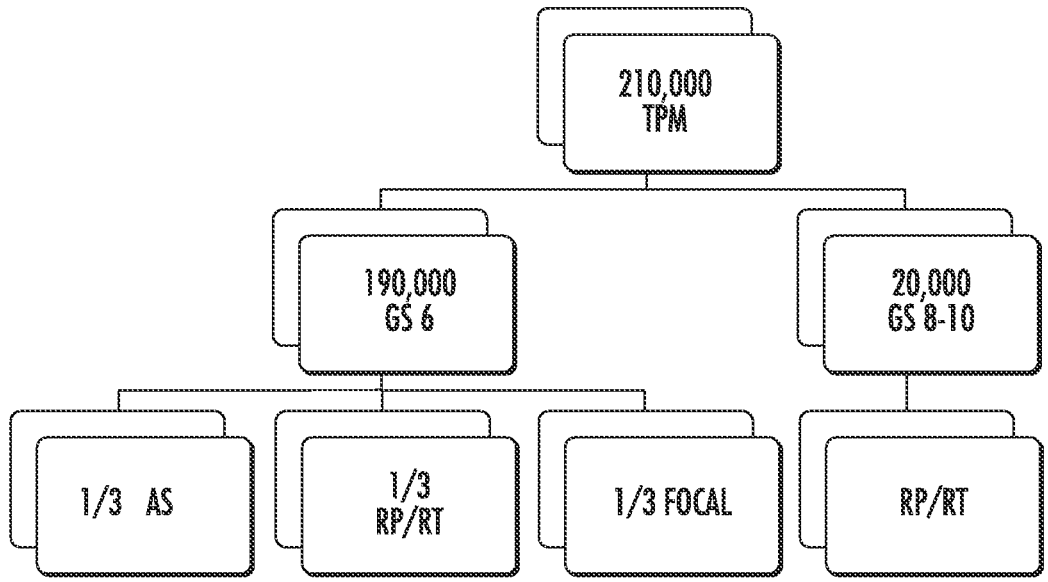
FIG. 2 is a schematic of a treatment algorithm.
Figure 3A:
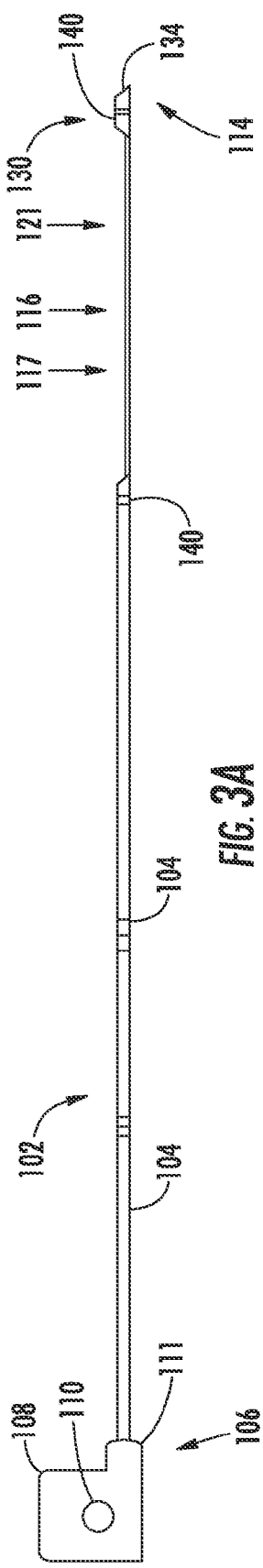
FIG. 3A is a side elevation view of an embodiment of a mandrel.
Figure 3B:
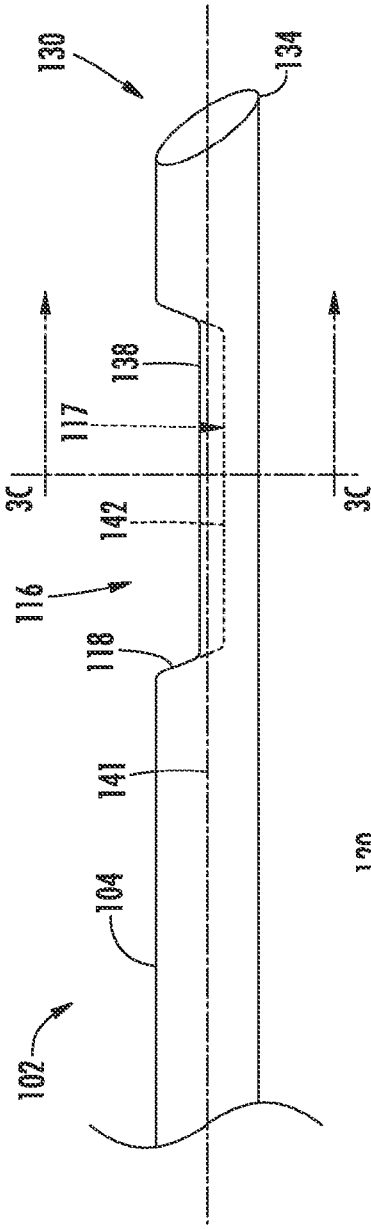
FIG. 3B is a side elevation view of an embodiment of a mandrel.
Figure 3C:
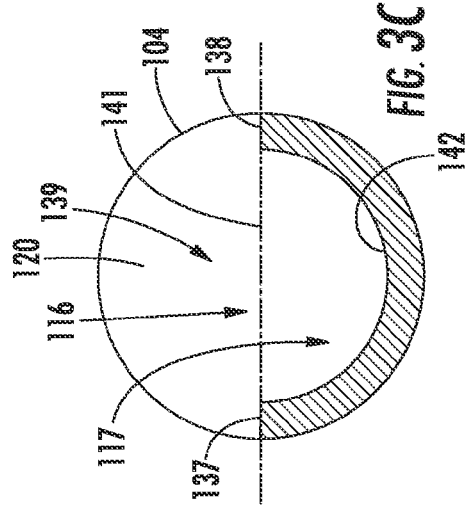
FIG. 3C is a cross section view of the mandrel taken along line 3C-3C in FIG. 3B.
Figure 3D:
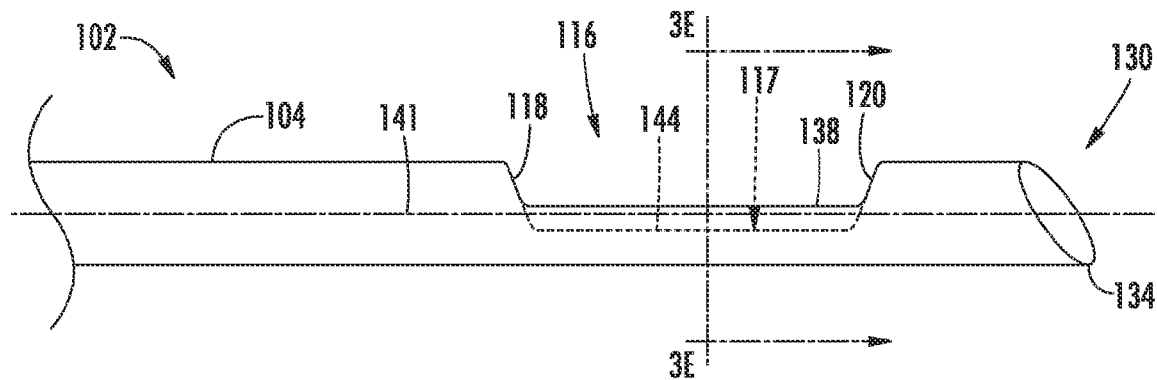
FIG. 3D is a side elevation view of an embodiment of a mandrel.
Figure 3E:
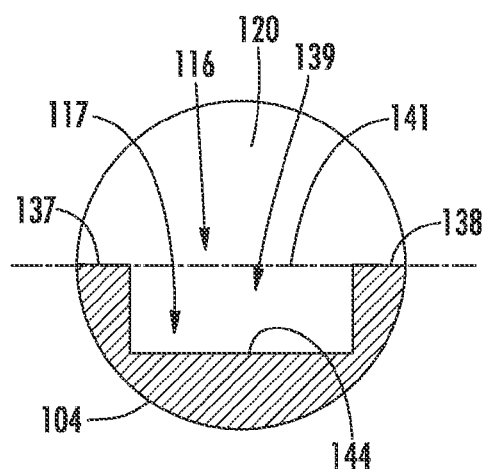
FIG. 3E is a cross section view of the mandrel taken along line 3E-3E in FIG. 3D.
Figure 4:
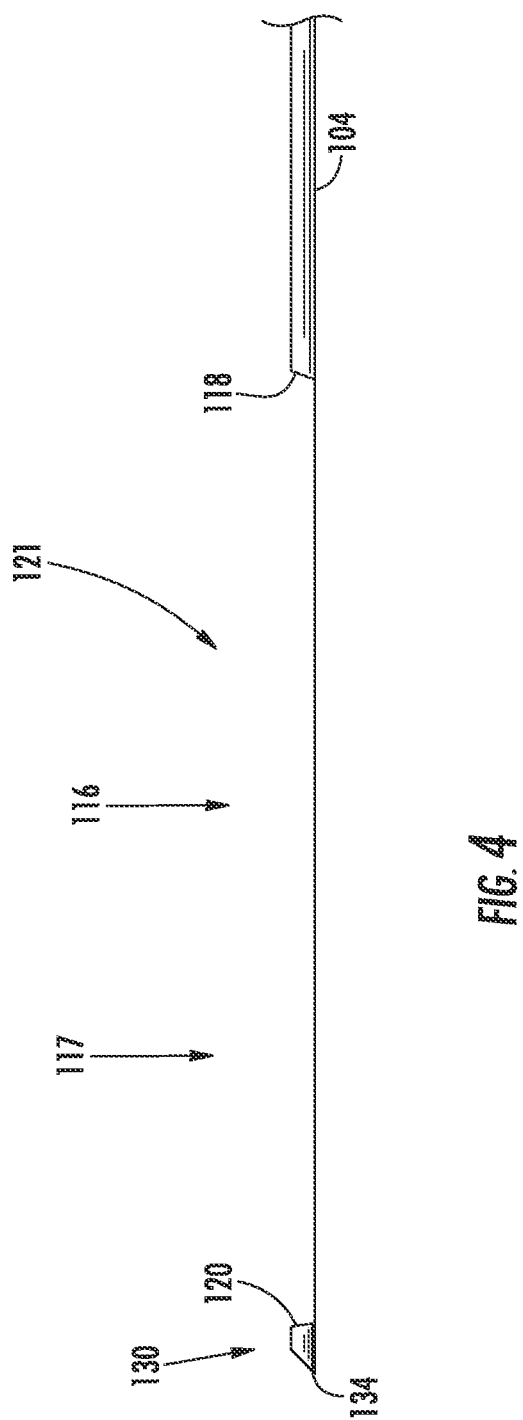
FIG. 4 is a side elevation view of an embodiment of a mandrel.

A needle assembly 100 is used to excise a tissue specimen from a target tissue site. Referring to FIGS. 3A-E, and 8-9, the needle assembly 100 includes an inner component 102 or mandrel that travels within an outer component 152 or cannula. Referring to FIGS. 3A-4, the mandrel or inner needle includes an elongated cylindrical body 104, extending from a proximal end 106 to a distal end 114. The body 104 has an outer diameter. In some embodiments the body 104 outer diameter is from about 0.1842 mm to about 4.572 mm, preferably from to about 1.27 mm to about 2.77 mm. The body 104 is manufactured from a surgically suitable material, including stainless steel. A generally rectangular first connecting element 108 forming an offset aperture 110 is located at the proximal end 106 for connecting the inner component 102 to an actuating assembly. The first connecting element 108 is molded to the proximal end 1006 forming a collar 111 about the body 104. The distal end 114 forms a tip 130 terminating at a point 134. The body 104 forms an adjacent core bed 116 extending between a first end 118, and a second end 120 located adjacent the tip 130, providing a cavity 121 for retaining a tissue specimen. In some embodiments, the second end 120 is about 5 mm from the point 134. The core bed 116 presents an inner surface 117 bound laterally by a first longitudinal edge 137 and an opposite second longitudinal edge 138, and extending from a distal end by the second end 120, and from a proximal end by the first end 118.

The core bed 116 has a longitudinal length between the first end 118 and second end 120 from about 1 mm to about 200 mm, preferably from about 20 mm to about 60 mm. The use of a mandrel with a core bed 116 of substantial length can result in poor stiffness, in particular, when the inner surface 117 lies below the central axis 141 of the body 104, the needle can deflect or break during use. In an embodiment, the core bed 116 forms an upwardly open lower cavity 139 whereby a substantial portion of the inner surface 117 lies below the central axis 141 between adjacent first and second longitudinal edges 137, 138 (FIGS. 3B-E). Longitudinal edges 137, 138 are at or above a horizontal plane coincident with the central axis thereby improving the stiffness of the body 104 at the core bed, and thus the cross sectional moment of inertia. Referring to FIGS. 3B-C, and embodiment of the cavity 139 is formed from a core bed 116 having a C-shaped cross sectional configuration presenting a trough-shaped cavity 142 with the bottom of the cavity 142 disposed below the central axis 141. Referring to FIGS. 3D-E, an embodiment of the cavity 139 is formed from a core bed 116 having a rounded bottom box-shaped cross sectional configuration presenting a rectangular cavity 144 with the bottom of the cavity 144 disposed below the central axis 141.

Figure 5:
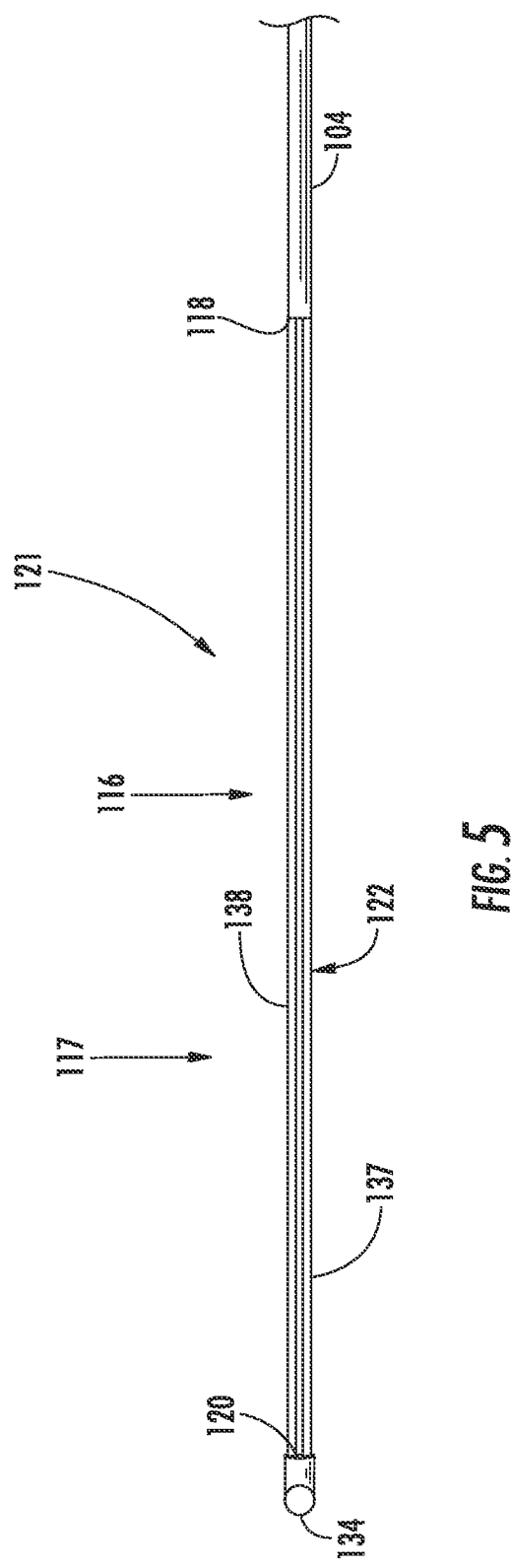
FIG. 5 is a plan view of an embodiment of a mandrel.
Figure 6:
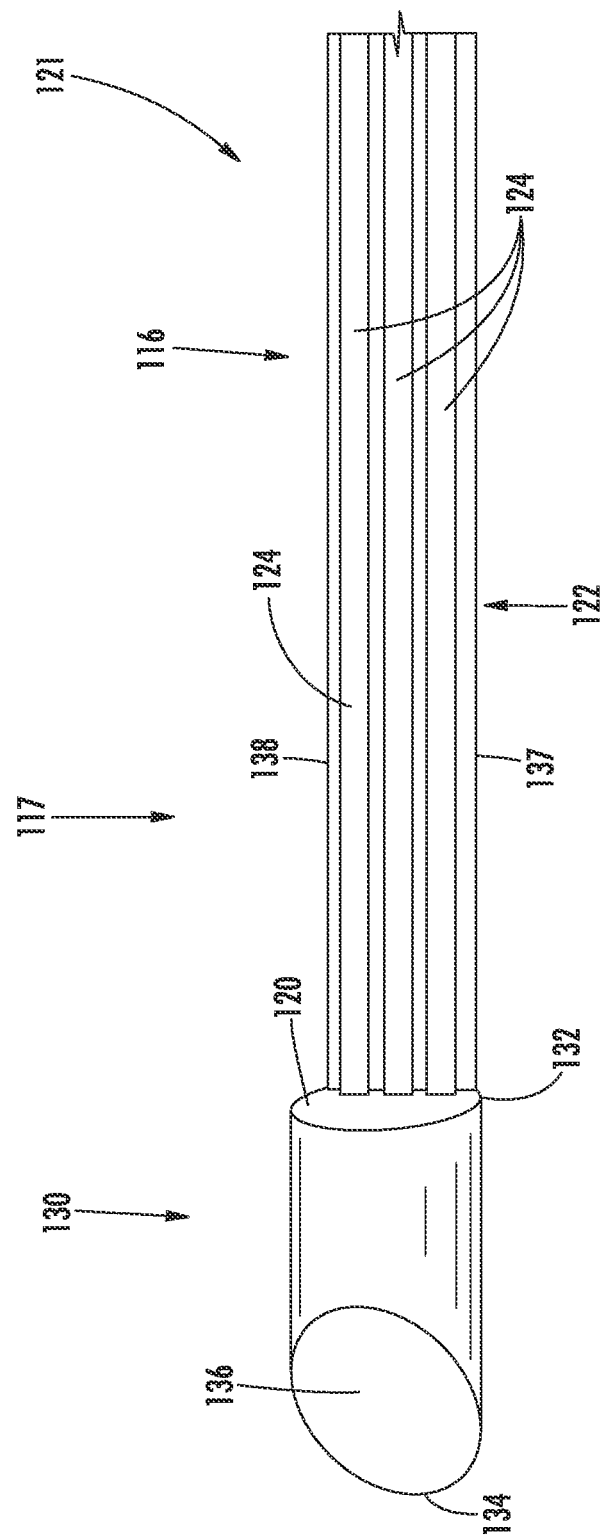
FIG. 6 is an enlarged plan view of the mandrel of FIG. 5.
Figure 7:
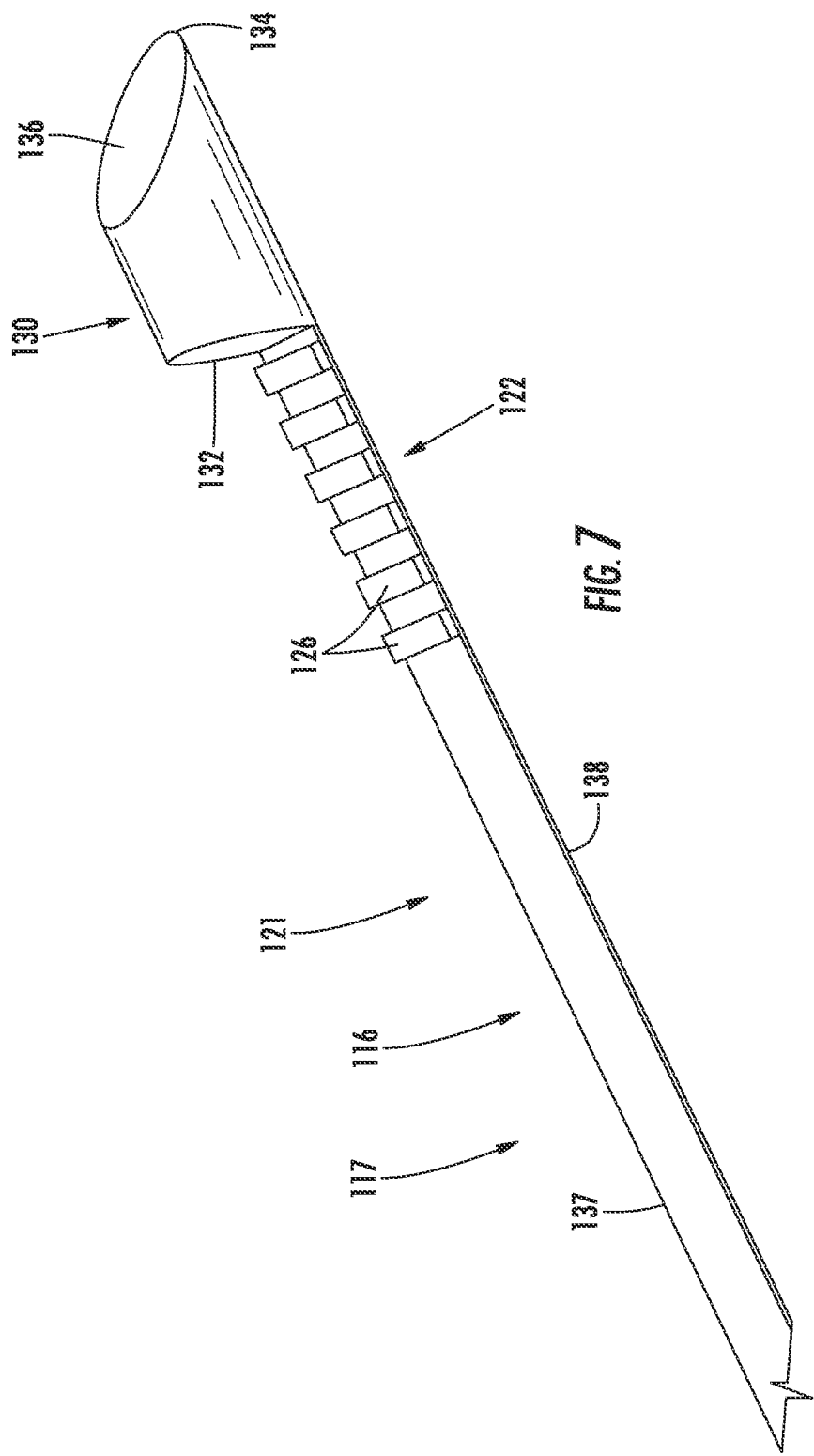
FIG. 7 is an isometric view of an embodiment of a mandrel.

In some embodiments, the core bed 116 forms one or more projections 122 with a contact surface 123 for one or more of marking, securing, impressing, engaging, orientating, and scoring the tissue specimen within the core bed 116. In some embodiments the projection 122 includes a plurality of adjacent longitudinal ridges 124 formed by the inner surface 117 extending the length of the core bed 116 between the first end 118 and second end 120 (FIG. 5-6) that contact the tissue specimen. In some embodiments the retaining member 122 includes a plurality of adjacent transverse ridges 126 formed by the inner surface 117 extending between the first longitudinal edge 137 and second longitudinal edge 138 spaced between the first end 118 and the second end 120 (FIG. 7) that contact the tissue specimen.

In some embodiments, ridges 126 are grouped at one end of the core bed 116 leaving the remainder of the inner surface 117 free from ridges 126. In an embodiment, ridges 126 are grouped at each end of the core bed 116 leaving the inner surface 117 between free from ridges.

Figure 7A:
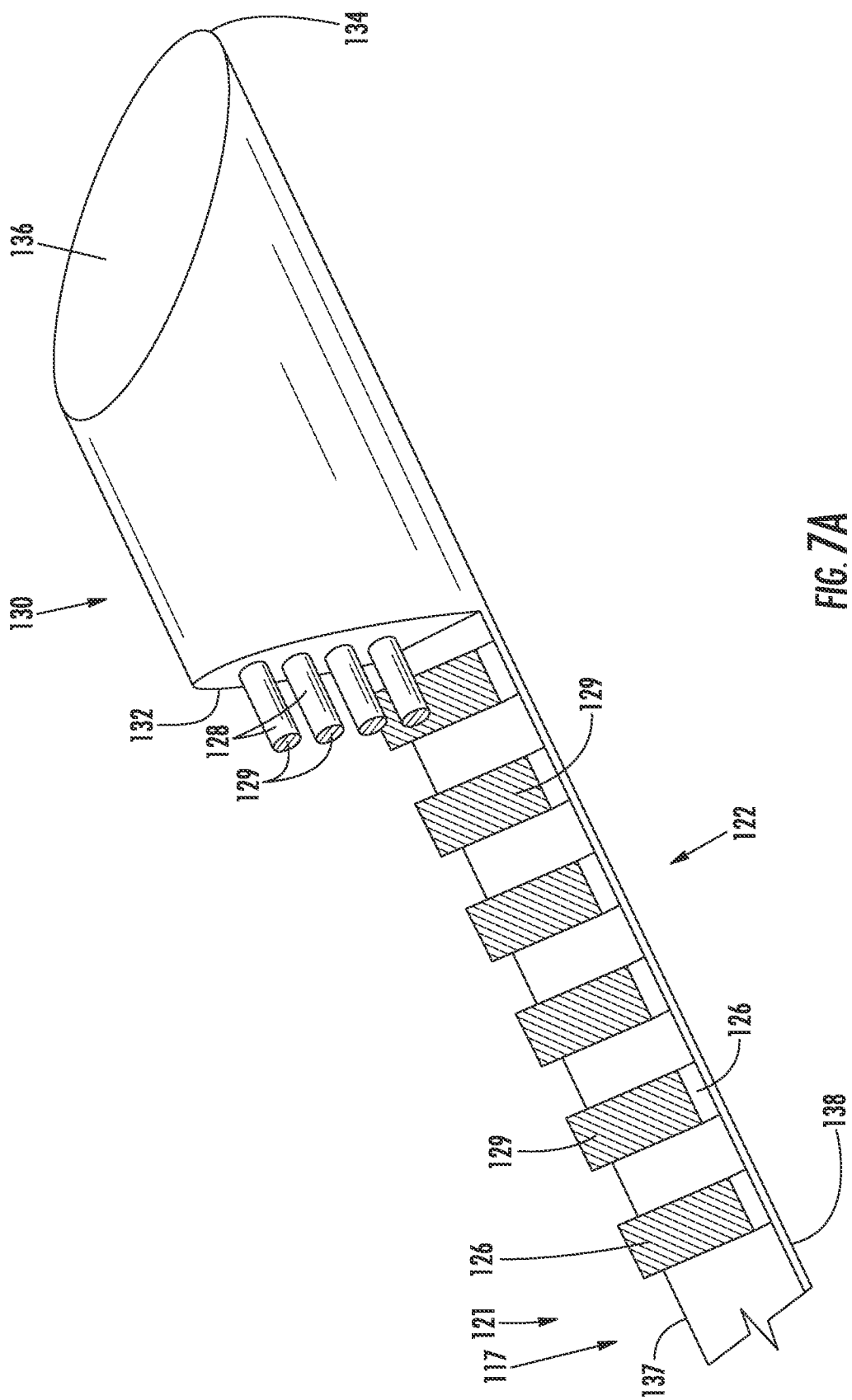
FIG. 7A is an isometric view of an alternative embodiment of a mandrel.

In some embodiments the projections 122 include one or more projections 128 formed by, and extending from, one or both the first end 118 and second end 120 that contact the ends of the tissue specimen. In an embodiment, the projections 128 extend generally longitudinally into the cavity 121 (FIG. 7A). In an embodiment, the projections 128 extend upward into the cavity 121. In some embodiments the projection 122 includes a plurality of adjacent ridges formed by the inner surface 117 spaced between the first end 118 and the second end 120 that are disposed at an angle that is between longitudinal and transverse. In some embodiments the projection 122 includes a plurality of spaced ridges formed by the inner surface 117 that are curvilinear across the core bed 116. The projection 122 creates a marking or impression on the excised tissue specimen providing a visual indication to the user of the orientation of the tissue specimen in the core bed. Because the orientation and location of the core bed 116 and cavity are known by the user, the marking or impression by the projections on the excised tissue specimen provide a visual indication to the user of the orientation of the tissue specimen in the target tissue prior to removal. The marking or impression on the excised tissue specimen and core bed 116 location and orientation can be correlated by a user allowing the pathological characteristics of the tissue specimen to be correlated with the target tissue.

In an embodiment, the projections 122, 128 include a marking agent 129 that is transferred to the tissue specimen, including an FDA approved ink or coloring agent, India ink, or a biocompatible natural or synthetic pigment capable of marking hard or soft tissue. In an embodiment, the marking agent further includes a biocompatible membrane that is transferred to and adheres to the tissue specimen. The marking agent is applied to the projection at the time of manufacture, or prior to use. The projection may be treated to releasably accept the marking agent. In an embodiment, the projection is mechanically treated, including etching or ablation, to releasably accept the marking agent. In an embodiment, the projection is chemically treated, including etching, ablation, or application of a releasing agent, to releasably accept the marking agent. The marking agent provides a visual indication to the user of the orientation of the tissue specimen in the core bed.

The tip 130 extends from a base 132 at a proximal end to the point 134 at a distal end. A cutting face 136 at the tip 130 allows the inner component 102 to cut tissue as it passes through the body. In some embodiments, one or more marks 140 at intervals along the body 104 enhance visibility of the inner component 102 when it is used with the imagining system 1032. In some embodiments, the one or more marks 140 appear at 5.0 cm intervals along the length of the body 104 between the tip 130 and first connecting element 108.

Referring to FIG. 8, the outer component 152 or outer needle includes an elongated tubular body 154 forming a sidewall 156 that extends from a proximal end 158 to a tip 168 at a distal end 166. The interior diameter of the body 154 is equal to or greater than the corresponding outer diameter of the mandrel body 104 used therewith thereby allowing the inner component 102 to freely travel therein. The body 154 is manufactured from a surgically suitable material, including stainless steel. A generally rectangular second connecting element 160 forms an offset aperture 162 located at the proximal end 158 for connecting the outer component 152 to an actuating assembly. The second connecting element 160 is molded to the proximal end 158 forming a collar 165 about the body 154. The end of the second connection element 160 forms a first opening 164, such as a Luer lock tip, allowing access to the interior of the body 154. The opening 164 allows the distal end 114 of the inner component 102 to be inserted into the proximal end 158 of the outer component 152 thereby allowing the tip 130, core bed 116, and body 104 to extend beyond the tip 168 through a second opening 176. The tip 168 extends from a base 170 at a proximal end to a point 172 at the distal end 166. A cutting face 174 at the tip 168 allows the outer component 152 to cut tissue as it passes. In some embodiments, one or more marks 178 at intervals along the body 154 enhance visibility of the outer component 152 when it is used with the imagining system 1032, and allow the location of the outer component 152 to be viewed within the body by an imagining system 1032. In some embodiments, the one or more marks 178 appear at 5.0 cm intervals along the length of the body 154 between the tip 168 and second connecting element 160. The opening 164 also allows an operator to introduce a liquid or a solid, such as medication or other agents, into the outer component 152 for depositing at the location of the tip 168. Other agents include a marker that is visible using an imaging system, such as ultrasound, allowing an operator subsequently identify the location of the removed biopsy tissue specimen for manipulation or treatment of the target tissue.

The inner component 102 and outer component 152 cooperate to remove a tissue specimen from a target tissue site. The needle assembly 100 is prepared for use by first inserting the inner component 102 into the outer component 152 as described above (FIG. 9). The overall length of each component 102, 152 is determined by the depth of the target tissue site from the exterior of the body, however, the overall length of the selected interior component 102 will be greater than the overall length of the selected outer component 152. In some embodiments, the length of the outer component 152 between the proximal end of the second connecting element 160 and the point 172 is equal to about less than the distance between the distal end of the first connecting element and the first end 118 of the core bed 116. In some embodiments, the length of the core bed 116 is greater than the length of the tissue intended to be excised.

The length of the inner component 102 between the collar 111 and the point 134 is greater than the length of outer component 152 between the collar 165 and point 172. In some embodiments, the second end 120 of the core bed 116 is approximately 6 cm beyond the point 172 when the collar 111 abuts the first opening 164.

In use, the needle assembly 100 is arranged in a first position whereby the first connecting element 108 and second connecting element 160 are mounted in an actuator assembly so that the tip 130 extends just beyond tip 168 to allow the needle assembly 100 to cut tissue as it is advanced into the body toward a target tissue site. Because the inner component 102 is designed to be of greater length than the outer component 152, the first connecting element 108 and second connecting element 160 are offset a distance when in the first position allowing the inner component 102 to travel within the outer component 152.

The needle assembly 100 is advanced toward the target tissue site until the tip 130 reaches an area adjacent the tissue to be removed. The maximum length of the tissue specimen capable of being excised is equal to the length between the first end 118 and second end 120 of the core bed 116. For an inner component 102 having a core bed 116 of great length, an operator can use the needle assembly 100 to excise tissues of varying lengths by limiting the length of core bed 116 that is exposed beyond the point 172 of the outer component 152. The target tissue is prepared for excision by first transitioning the needle assembly 100 from the first position to a second position. The transition occurs by advancing the inner component 102 within the outer component 152 exposing the desired length of core bed 116 beyond the point 172. In the second position the core bed 116 is exposed to the tissue to excise and the projection 122 engages the tissue, and alternatively holding it in place. The projection 122 and/or marking agents leave identifiers on the tissue specimen providing identification and orientation of the tissue specimen, and allowing any pathological characteristics of the tissue specimen to be correlated with the target tissue.

The tissue specimen is removed from the target tissue site by next transitioning the needle assembly 100 from the second position to a third position. The transition occurs by advancing the outer component 152 along the inner component 102 a sufficient distance whereby the point 172 advances from a position proximal the first end 118 of the cored bed 116 to a position distal the second end 120 of the core bed 116. The cutting face 174 cuts the tissue exposed above the core bed 116 as the point 172 advances encapsulating a portion of tissue between the inner component 102 and the outer component 152. The needle assembly 100 is then withdrawn from the tissue site, with the selected tissue specimen, to the exterior of the body.

The tissue specimen may be removed from the needle assembly 100 by transitioning the needle assembly 100 from the third position to a fourth position. The transition occurs by advancing the inner component 102 within the outer component 152 a sufficient distance to expose the core bed 116 beyond the point 172 of the outer component 152 thereby exposing the tissue within the core bed 116. The excised tissue may then be transferred to a medium until pathological evaluation. Alternatively, the tissue specimen may be removed from the needle assembly 100 by withdrawing the inner component 102 from the outer component 152 thereby exposing the tissue within the core bed 116.

Figure 33:
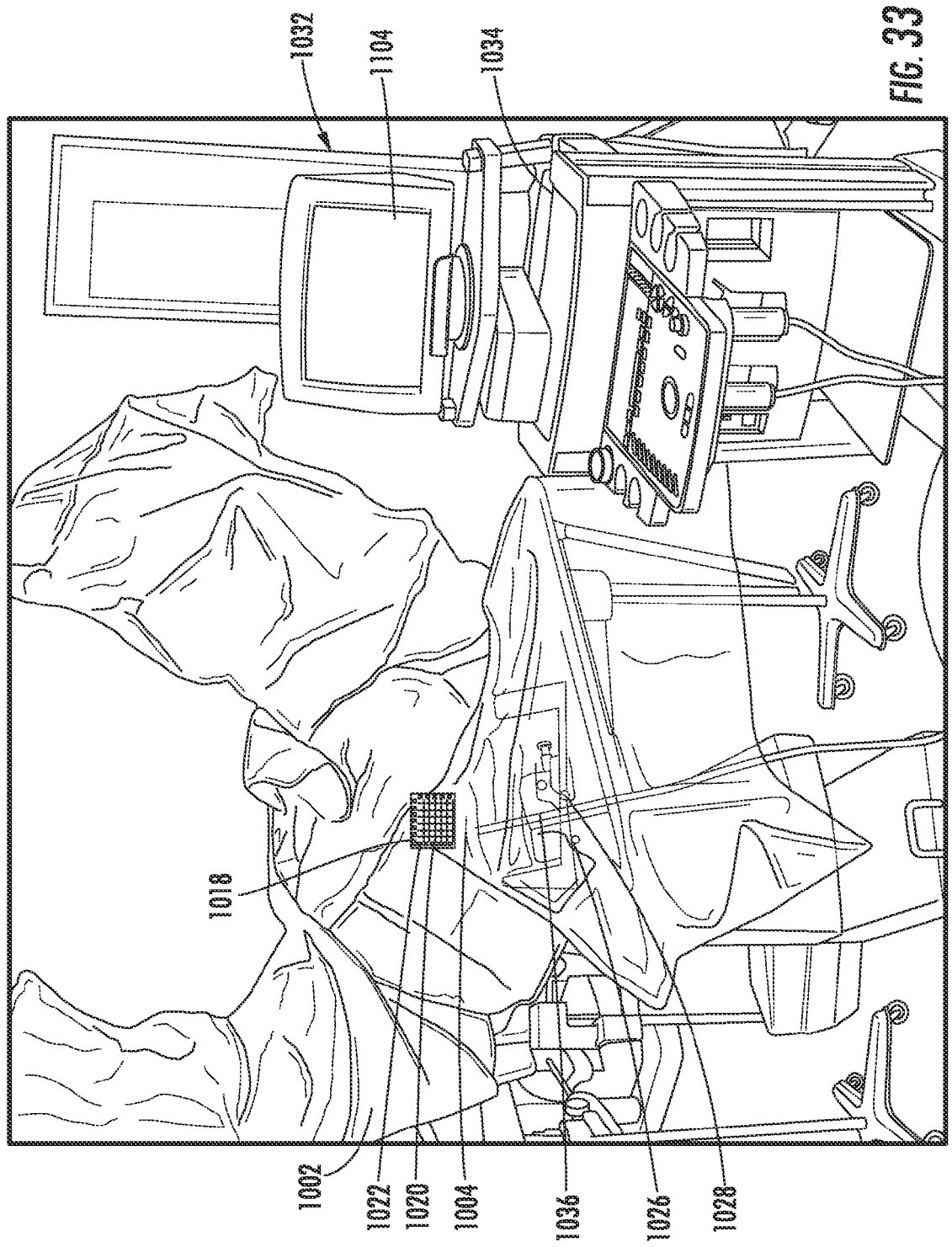
FIG. 33 is an illustration of a patient positioned for a prostate biopsy procedure.

The needle assembly 100 can be used with various target tissue types, including breast tissue, kidney tissue, liver tissue, and prostate tissue. In an embodiment, the needle assembly 100 is used to excise or biopsy a tissue specimen from a prostate gland, whereby the prostate gland is the target tissue. Biopsies of the prostate gland can take place with the patient in various positions. An approach to a procedure for removing biopsies from the prostate gland is shown in FIG. 33, whereby a patient 1002 is positioned in a lithotomy position whereby the prostate is orientated above or anterior the rectum, the rectum is orientated below or posterior the prostate, the base of the prostate orientated toward the head of the patient and the apex of the prostate opposite, and the prostate is accessed in a transperineal manner. During a transperineal biopsy procedure, the needle assembly 100 is arranged in the first position whereby the core bed 116 is orientated to face posterior or toward the rectum. The needle assembly 100 is advanced into the prostate from the apex toward the base until the tip 130 reaches an area adjacent the tissue to be removed. The inner component 102 is advanced into the prostate with the core bed 116 facing downward, and the projections contacting the target tissue. The projection 122 and/or marking agents leave identifiers on the tissue specimen providing the user with identification and orientation information after the tissue specimen is removed and processed. For example, use of an inner component 102 with transverse ridges 126 and projections 128 extending into the cavity 121 from the second end 120, and where the ridges 126 and projections 128 include marking agents, the excised tissue specimen would have visible marks on the base end of the specimen from the projections 128, and would have visible marks on the anterior end of the specimen adjacent the base end from the ridges 126. The markings on the tissue specimen allow a user to correlate any pathological findings associated with the tissue specimen to their location in the target tissue.

In some embodiments, the inner component 102 can be used for the introduction of a liquid or a solid, such as medication or other agents, or an elongated flexible element, such as a fiber or wire for manipulating tissue structures when the needle assembly 100 is in either the first position or the second position. Other agents include a marker that is visible using an imaging system, such as ultrasound, allowing an operator subsequently identify the location of the removed biopsy tissue specimen for manipulation or treatment of the target tissue. In some embodiments, the body 104 is a hollow tubular member forming a passage extending between an opening at a proximal end 106 and an opening at the first end 118 for introducing the liquid, solid, or elongated flexible member. In some embodiments, the tip 130 is a hollow tubular member forming a passage extending between an opening at the second end 120 and an opening at the cutting face 136 allowing further extension of the elongated flexible element past the tip 130.

It will be appreciated that the bodies 104, 154 can be used with or without connecting elements, and may be used with the core bed 116 in any orientation with respect to an aspect of the target tissue.

It will be appreciated that the components of the needle assembly 100 can be used for various other applications. Moreover, the needle assembly 100 can be fabricated in various sizes and from a wide range of suitable materials, using various manufacturing and fabrication techniques.

Actuator Assembly

Figure 10:
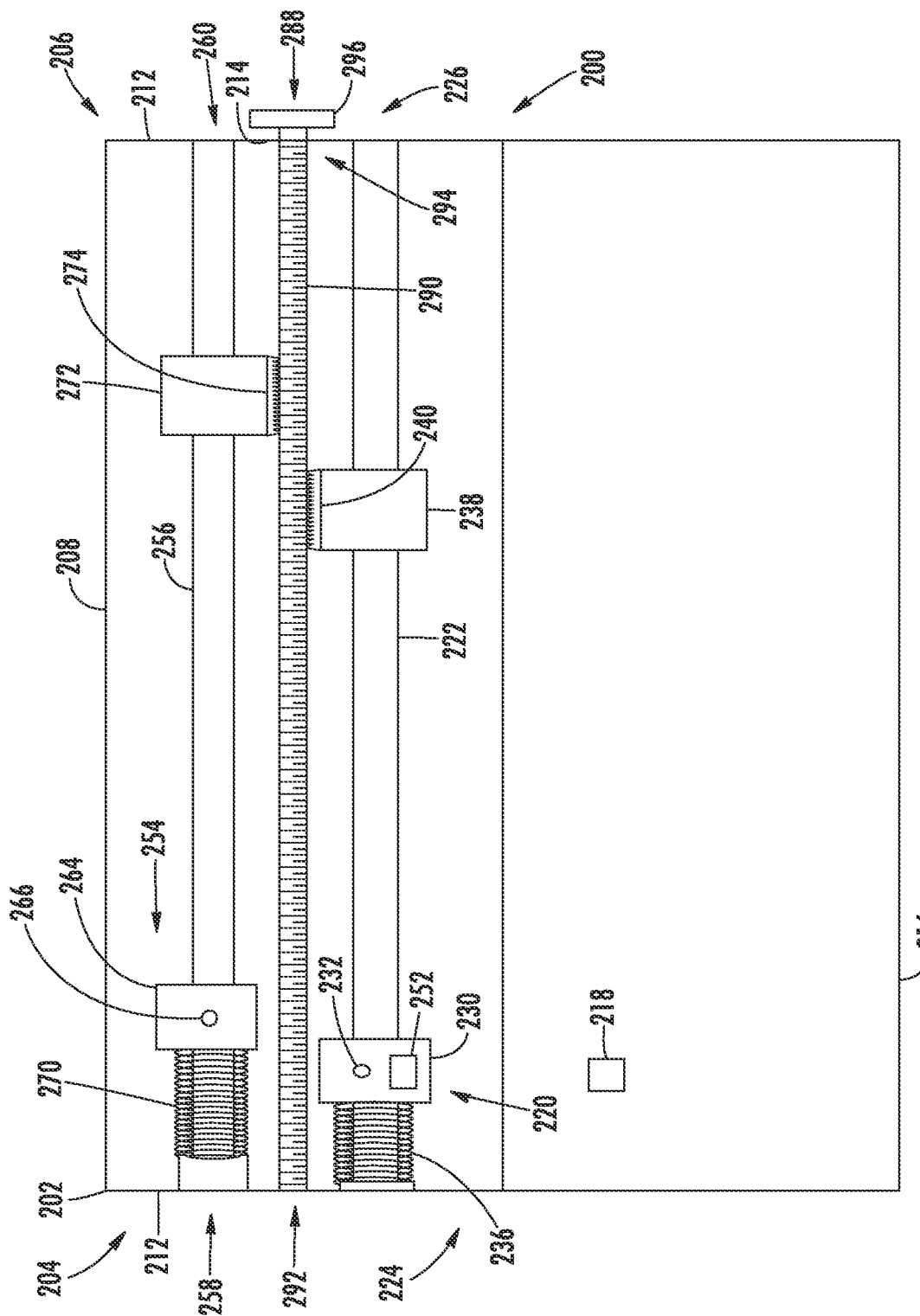
FIG. 10 is a plan view of an embodiment of an actuator assembly.

In some embodiments, an actuator assembly 200 is used with the needle assembly 100 to excise the tissue specimen from the target tissue site. Referring to FIG. 10, an embodiment of the actuator assembly 200 includes a body 202 extending from a proximal end 204 to a distal end 206 forming sidewalls 208, including a front wall 210 at the distal end 206, and a rear wall 212 at the proximal end 204. An opening 214 in the front wall 210 allows the needle assembly 100 to extend from the actuator assembly 200. A cover 216 is movable on the body 202 allowing access to the interior of the actuator assembly 200.

The actuator assembly 200 includes an actuator for axially moving each of a mandrel and a cannula. A first actuator member 220 for moving the mandrel or inner component 102 includes a first guide 222 extending from a proximal end 204 at the rear wall 212, to a distal end 206 at the front wall 210. A first carriage assembly 230 moves axially along the first guide 222 for moving the inner needle within the cannula or outer component 152. A biasing member, such as a spring 236, is disposed between the first carriage assembly 230 and the rear wall 212, and when compressed, biases the first carriage assembly 230 toward the distal end 206 of the actuator assembly 200. A pin 232 extending from the first carriage assembly 230 receives the first connecting element 108 of the mandrel. A notch 234 in the first carriage assembly 230 receives a first firing pin 242 when the first carriage assembly 230 is moved to the distal end 206. A first carriage stop 238 disposed between the first carriage assembly 230 and the front wall 210 limits the forward movement of the first carriage assembly 230 along the first guide 222.

A second actuator member 254 for moving the outer component 152 is disposed adjacent the first actuator member 220. The second actuator member 254 includes a second guide 256 extending from a proximal end 258 at the rear wall 212, to a distal end 260 at the front wall 210. A second carriage assembly 264 moves axially along the second guide 256 for moving the outer component 152 about the inner component 102. A biasing member, such as a spring 270, is disposed between the second carriage assembly 264 and the rear wall 212, and when compressed, biases the second carriage assembly 264 toward the distal end 206 of the actuator assembly 200. A pin 266 extending from the second carriage assembly 264 receives the second connecting element 160 of the cannula. A notch 268 in the second carriage assembly 264 receives a second firing pin 276 when the second carriage assembly 264 is moved to the distal end 206. A second carriage stop 272 disposed between the second carriage assembly 264 and the front wall 210 limits the forward movement of the second carriage assembly 230 along the second guide 256.

An adjusting member 288 allows an operator to move the first carriage stop 238 and second carriage stop 272. The adjusting member 288 includes an externally threaded member 290 disposed between the first guide 222 and second guide 256, and extend between a proximal end 292 rotatably disposed adjacent the rear wall 212, and a distal end 294 rotatably disposed at the front wall 210. A wheel 296 at the exterior of the body 202 is operably connected to the threaded member 290 for rotating the threaded member 290. A threaded surface 240 on the first carriage stop 238, and a threaded surface 274 on the second carriage stop 272 interface with the threaded member 290 whereby rotation of the threaded member 290 moves the threaded members along their respective guides. The distance between the distal edge of the first carriage assembly 230 and proximal edge of the first carriage stop 238 can be adjusted in some embodiments from about 0 mm to about 70 mm, and in some embodiments from about 20 mm to about 60 mm. An indicator on the wheel 296 or at another location on the actuator assembly 200, provides an indication of the distance between the first carriage assembly 230 and first carriage stop 238, and thus, the distance an inner component 102 will travel through a target tissue, discussed in more detail below.

Figure 11:
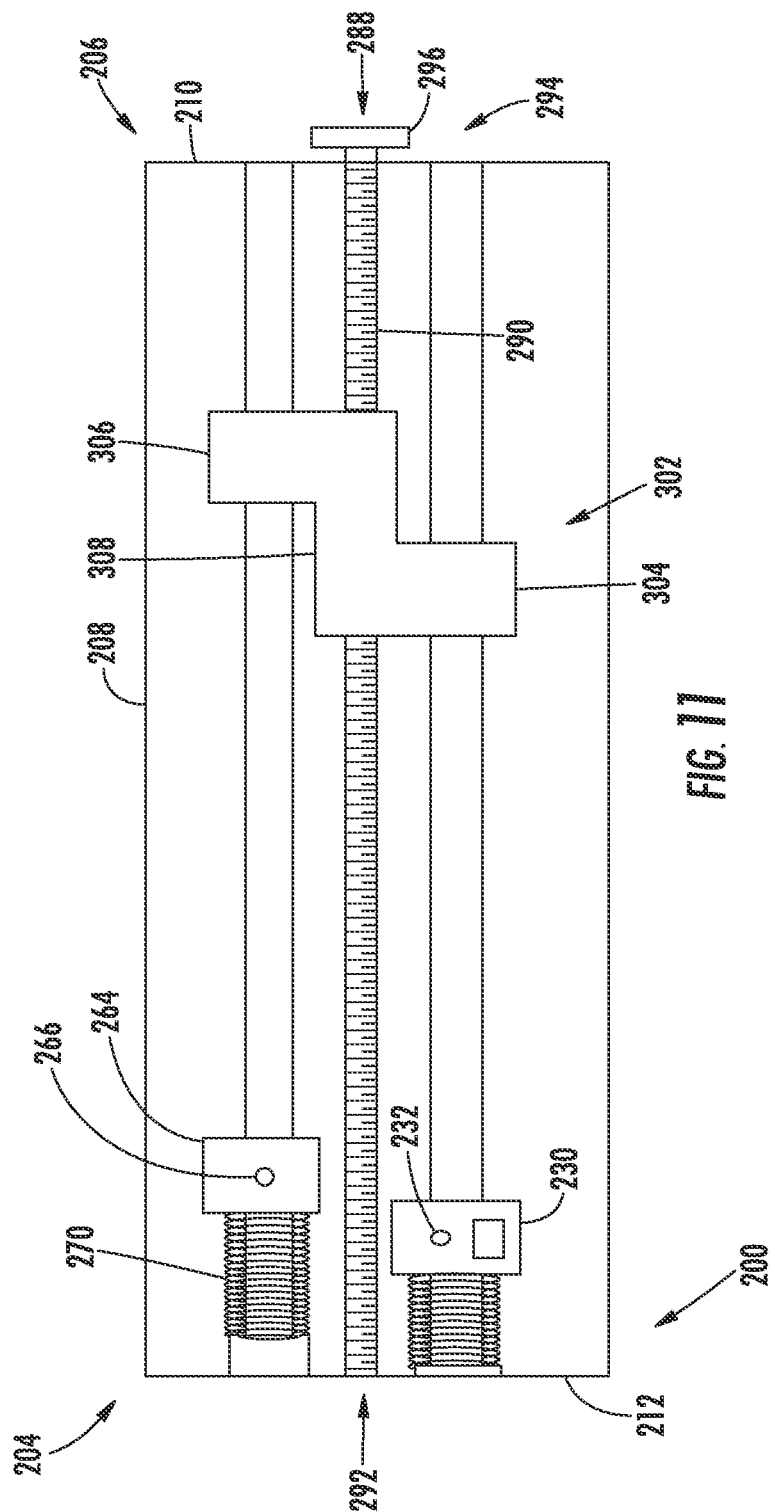
FIG. 11 is a plan view of an embodiment of an actuator assembly.

In some embodiments, the first carriage stop and second carriage stop is a unitary stop 302 (FIG. 11). The unitary stop 302 includes a first carriage stop 304 and second carriage stop 306 connected by a bridge 308, with the first and second carriage stops 304, 306 and bridge 308 forming an internally threaded passage that is received on the threaded member 290.

Figure 12:
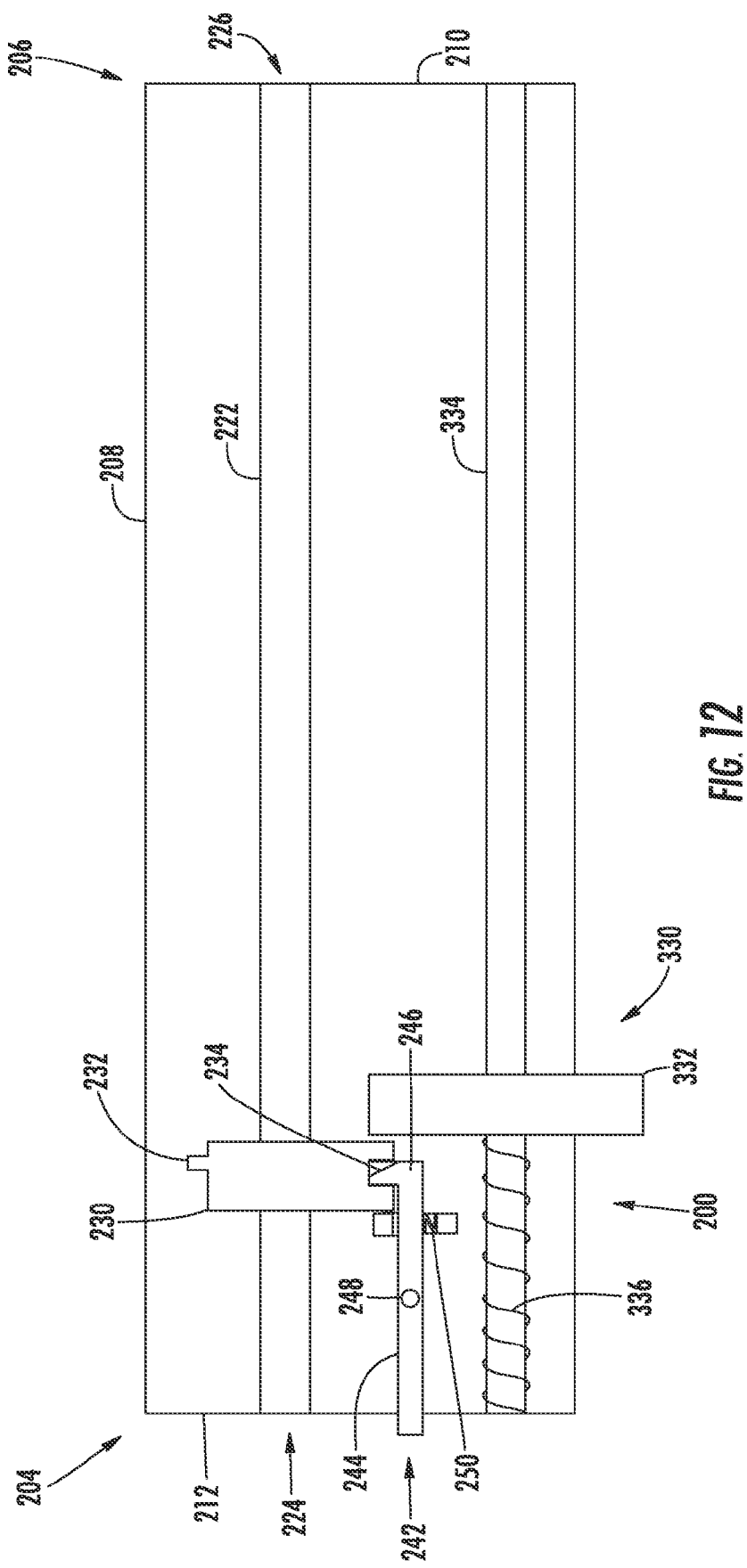
FIG. 12 is a side elevation view of an embodiment of an actuator assembly showing a first carriage assembly and associated firing pin.
Figure 13A:
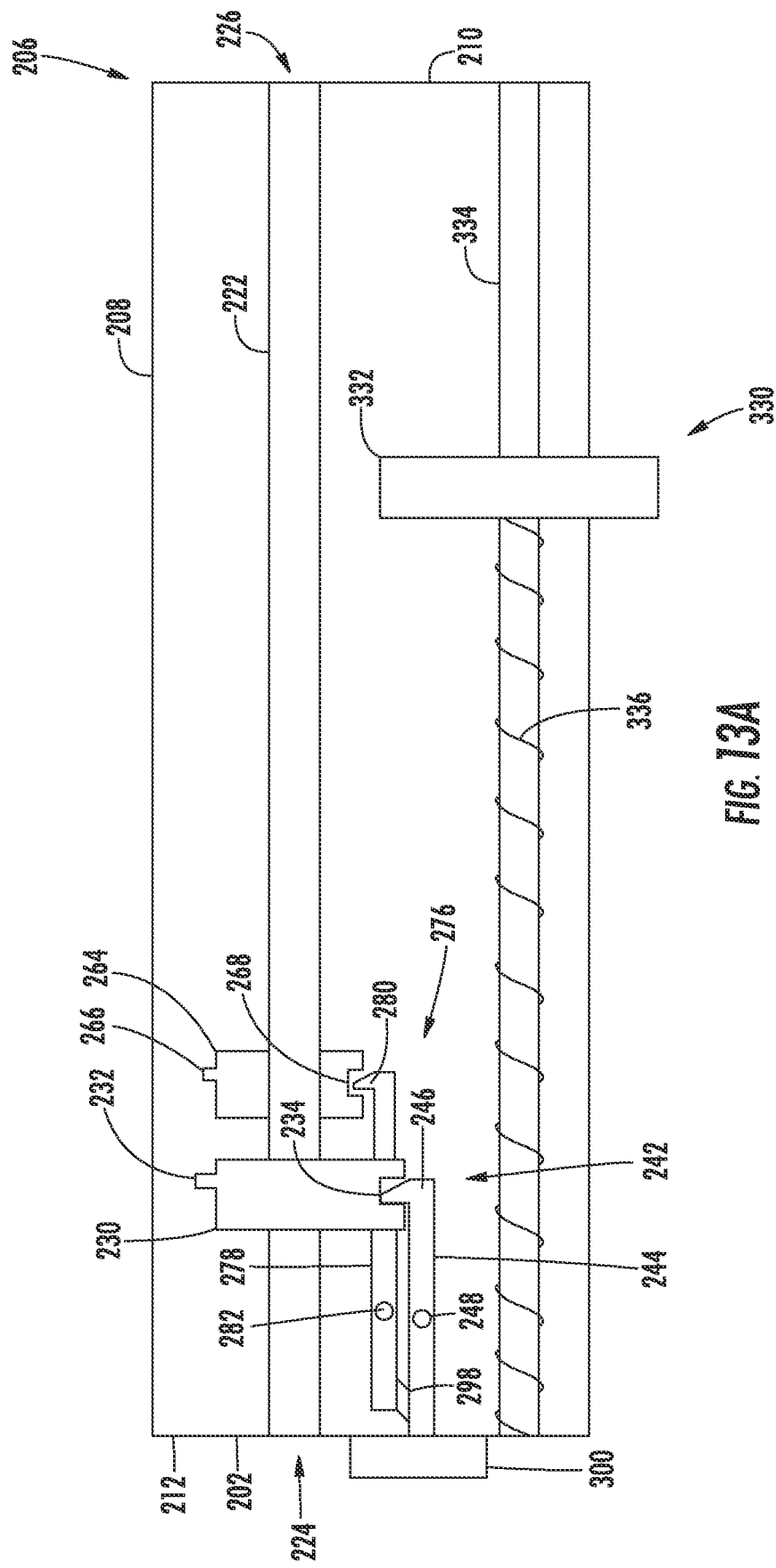
FIG. 13A is a side elevation view of an embodiment of an actuator assembly showing a first and second carriage assembly and associated firing pins.

The actuator assembly 200 is prepared for use by actuating the adjusting member 288 to set the distance between the first carriage stop 238 and the first carriage assembly 230 when the first carriage assembly 230 is in a first position or firing position. A needle assembly 100 with body 104 positioned within body 154 is loaded into the actuator assembly 200 by opening the cover 216 and inserting pin 232 into aperture 110 and inserting pin 266 into aperture 162, with the needle assembly 100 exiting from the body 202 through the opening 214. The cover 216 is closed and the first and second carriage assemblies 230, 264 are moved to their first position or firing position. The first carriage assembly 230 is moved to a first position by moving it toward the rear wall 212, such as by pushing or pulling it into position by a first cocking mechanism 330. The mechanism 330 includes a third guide 334 extending between the front wall 210 and rear wall 212. A first biasing arm 332 extends outward to the exterior of the body 202 and moves axially along the third guide 334 within a channel in the sidewall 208 for moving the first carriage assembly 230 to the first position. Moving the first biasing arm 332 from a start position toward the proximal end 204 compresses spring 236, until the protrusion 246 of the first firing pin 242 engages the notch 234. Moving the first biasing arm 332 compresses a spring 336 (FIG. 12), wherein upon engagement of the first firing pin 242 and the notch 234, the spring 336 biases the first biasing arm 332 to the neutral starting position (FIG. 13). In the first position the first firing pin 242 ceases rearward movement of the first carriage assembly 230 and prevents forward movement of the inner needle. The first firing pin 242 includes an arm 244 extending from the interior of the body 202 through the rear wall 212 to the exterior of the actuator assembly 200. A spring 250 biases against the arm 244 causing the protrusion to engage the notch 234. A pivot 248 connected to the arm 244 inside the body 202 allows the first firing pin 242 to be actuated between an engaged position and a disengaged position from the exterior of the body 202. The first carriage assembly 230 includes a marking 252 that are visible through a window 218 in the cover 216 showing a user that the first carriage assembly 230 is ready for firing.

The second carriage assembly 264 is moved to a first position by moving it toward the rear wall 212, such as by pushing or pulling it into position by a second cocking mechanism. The second mechanism includes a fourth guide, adjacent the third guide, extending between the front wall 210 and ear wall 212. A second biasing arm extends outward to the exterior of the body 202 and moves axially along the fourth guide within a channel in the sidewall 208 for moving the second carriage assembly 264 to the first position. Moving the second biasing arm from a start position toward the proximal end 204 compresses spring 270, until the protrusion 280 of the second firing pin 276 engages the notch 268. Similar to above, moving the second biasing arm compresses a spring, wherein upon engagement of the second firing pin 276 and the notch 268, the spring biases the second biasing arm to the neutral starting position. In the first position the second firing pin 276 ceases rearward movement of the second carriage assembly 264 and prevents forward movement of the outer needle. The second firing pin 276 includes an arm 278 extending from the interior of the body 202 through the rear wall 212 to the exterior of the actuator assembly 200. A spring 284 biases against the arm 278 causing the protrusion to engage the notch 266. A pivot 282 connected to the arm 278 inside the body 202 allows the second firing pin 276 to be actuated between an engaged position and a disengaged position from the exterior of the body 202.

The length of travel of the inner component 102 is determined by the distance of the first carriage assembly 230 in its first position from the first carriage stop 238. As described above, forward movement of the first carriage assembly 230 is limited by the location of the first carriage stop 238. The distance between the first carriage stop 238 and the first carriage assembly 230 in its first position, or needle throw length, determines the length of forward movement of the inner needle and thus the length of the core bed 116 exposed beyond the point 172 of the cannula. The needle throw length can be adjusted in some embodiments from about 0 mm to about 70 mm. In some embodiments, the needle throw length is from about 20 mm to about 60 mm. In some embodiments, the adjusting member 288 is indexed whereby the needle throw length is about 25 mm, about 30 mm, and about 35 mm. The needle throw length determines the length of the tissue specimen removed from the target tissue site. Forward movement of the second carriage assembly 264 is limited by the location of the second carriage stop 272. The distance between the second carriage stop 272 and the second carriage assembly 264 in its first position determines the throw length.

Figure 16:
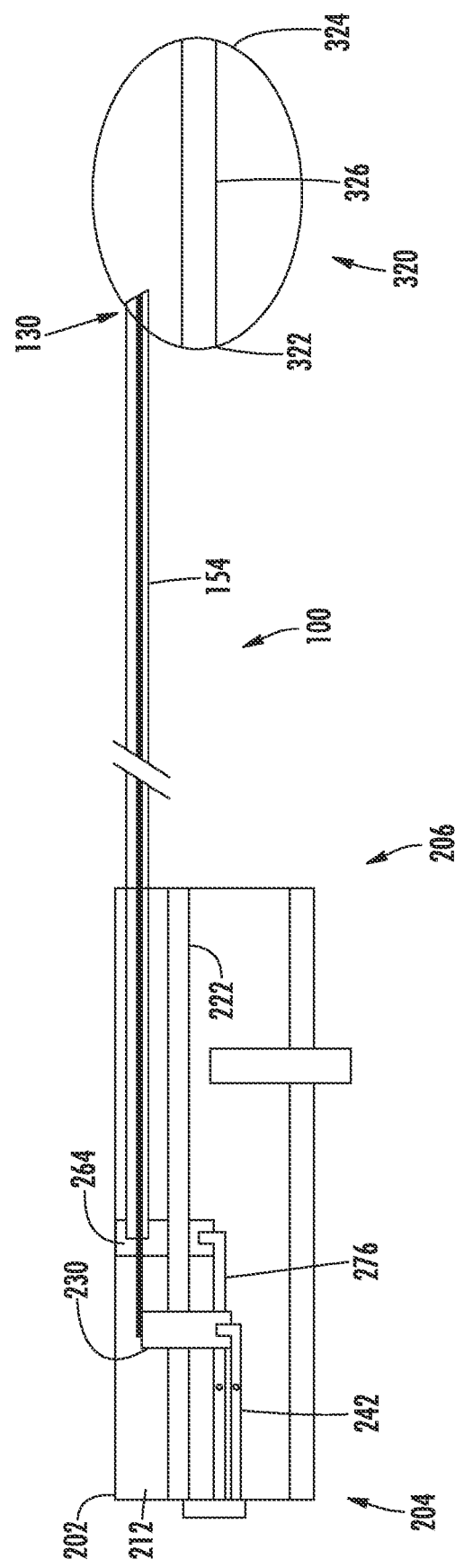
FIG. 16 is a schematic showing a side elevation view of a needle assembly and a target tissue.
Figure 17:
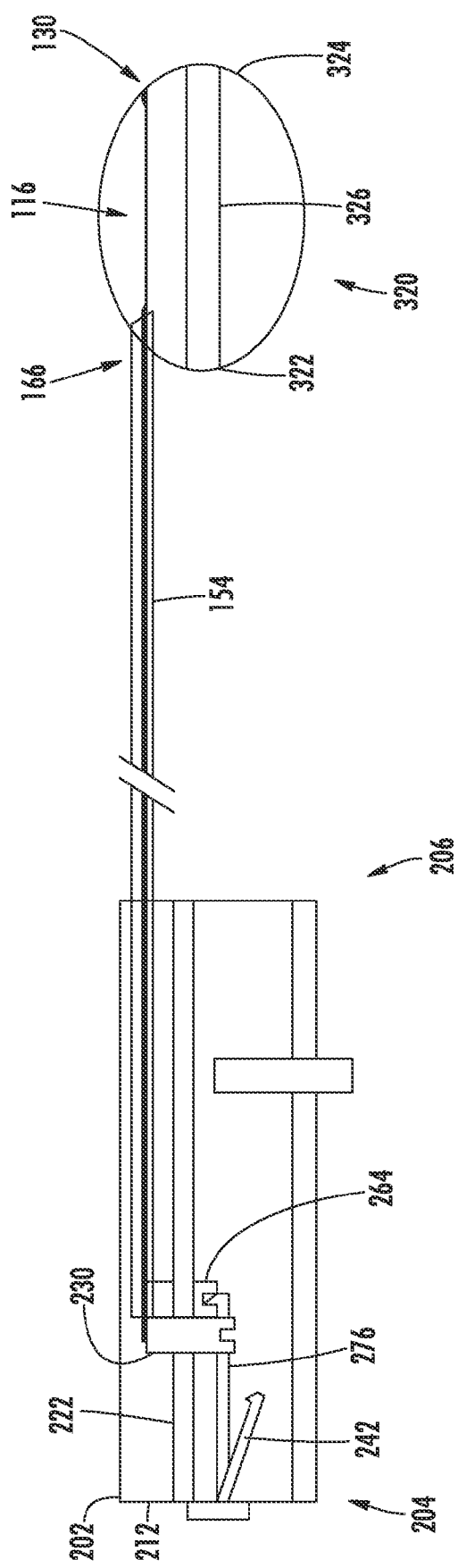
FIG. 17 is a schematic showing a side elevation view of a mandrel within a target tissue.
Figure 18:
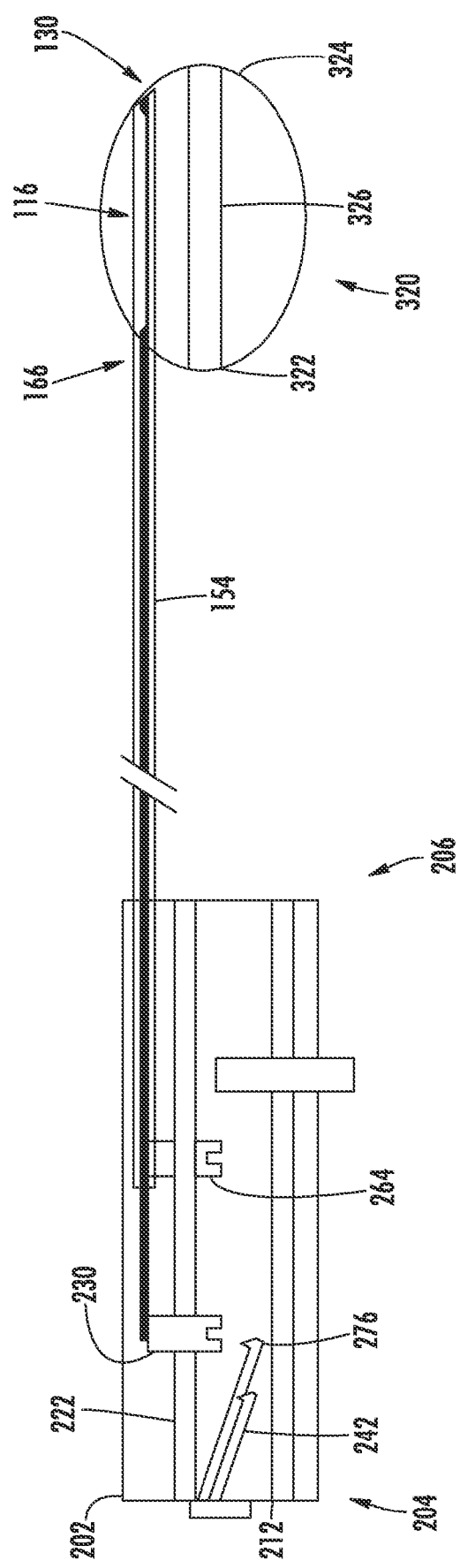
FIG. 18 is a schematic showing a side elevation view of a cannula within a target tissue.
Figure 19:
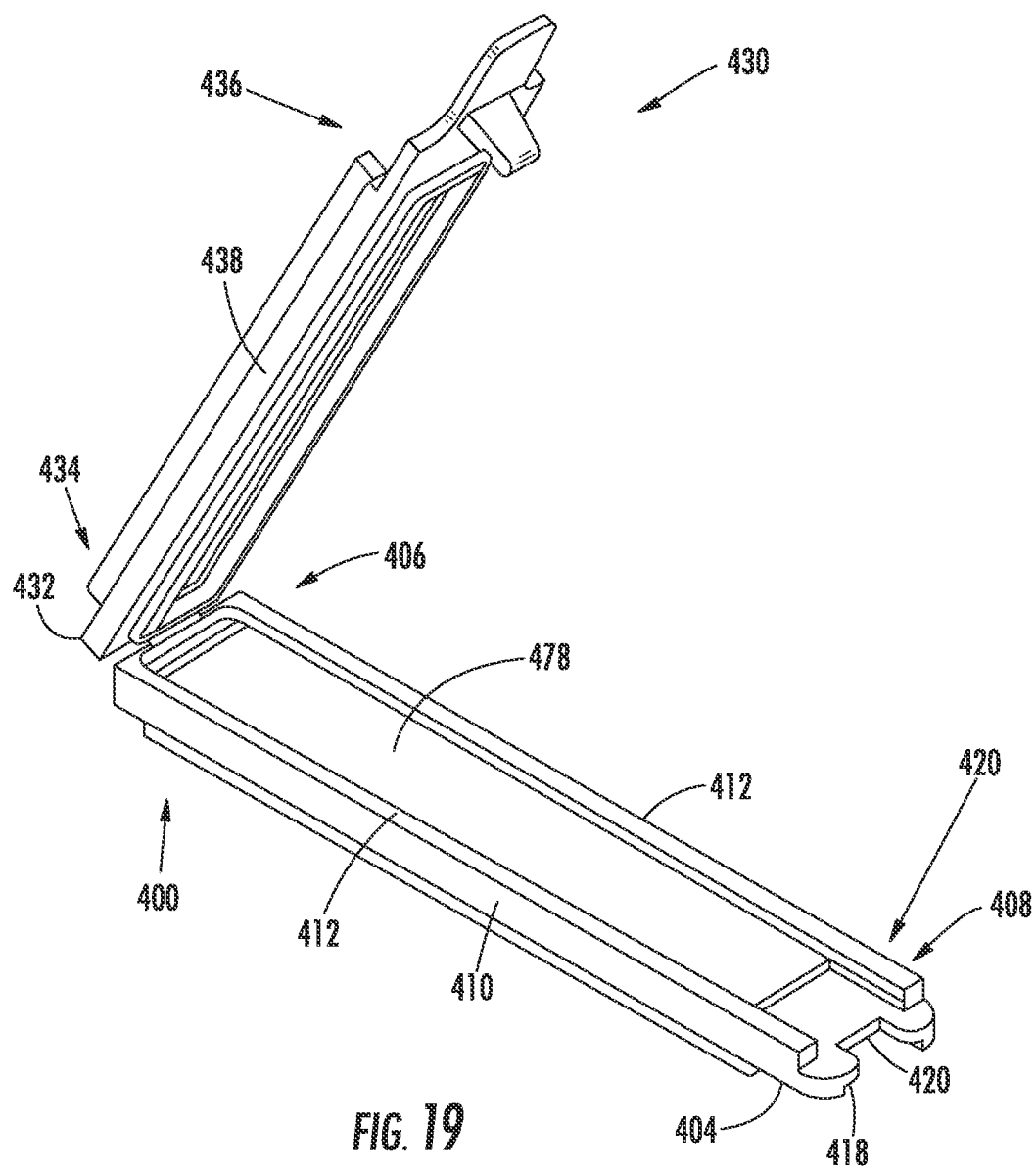
FIG. 19 is an isometric view of an embodiment of a cartridge assembly in an open position.

Once the inner and outer needles are in their first positions in the actuator assembly 200 the variable throw biopsy device is ready for use to excise tissue. As described above, the tip of the needle assembly 100 is advanced from outside the body toward the target tissue site until the tip 130 reaches an area adjacent the tissue to be removed. At this time, the throw length can be adjusted before firing by actuating the adjusting member 288 to set the distance between the first carriage stop 238 and the first carriage assembly 230. An adjustment to the throw length may be made, for example, after viewing the position of the needle assembly 100 in the body by an imaging system, such as an ultrasound image. Referring to FIG. 16, the needle assembly 100 is shown being advanced toward a schematic of a target tissue site, such as a prostate gland 320, with the tip 130 at the apex 322 of the prostate gland 320 and the core bed 116 facing upward. As discussed above, the core bed 116 can be manufactured for use with an actuator assembly 200 whereby the core bed 116 faced downward or posteriorly when used with the actuator 200 as shown in FIGS. 16-18. The inner needle or mandrel is fired or moves from its first position to a second position by actuation of the first firing pin 242. When the first firing pin 242 is actuated, disengaging the protrusion 246 from the notch 234, the first carriage assembly 230 is no longer held stationary against the biasing force of the compressed spring 236, and the spring 236 rapidly decompresses forcing the first carriage assembly 230 and biopsy needle forward toward the first carriage stop 238 and exposing a corresponding length of the core bed 116 (FIG. 17). The length of core bed 116 exposed to the tissue for removal from the prostate gland 320 includes tissue extending from the apex 322 to the base 324 of the prostate gland 320 in a region above the urethra 126. In some embodiments, as described above, the projections 122 engage the tissue specimen holding it in place within the core bed 116. In some embodiments, as described above, the projections 122 engage the tissue specimen leaving marks on the tissue specimen for later identification and proper orientation of the tissue specimen relative to its position in the target tissue.

Referring to FIG. 18, the tissue specimen is excised from the target tissue by firing the cannula. Referring to FIG. 17, the cannula is fired or moves from its first position to a second position by actuation of the second firing pin 276. When the second firing pin 276 is actuated disengaging the protrusion 280 from the notch 268, the second carriage assembly 264 is no longer held stationary against the biasing force of the compressed spring 270, and the spring 270 rapidly decompresses, forcing the second carriage assembly 264 forward toward the second carriage stop 272 covering the exposed length of the core bed 116. As the outer component 152 moves along the inner component 102 the point 172 advances from a position adjacent the first end 118 of the cored bed 116 to a position distal the second end 120 of the core bed 116. The cutting face 174 cuts the tissue exposed above the core bed 116 as the point 172 advances, encapsulating a portion of tissue between the inner component 102 and the outer component 152. The needle assembly 100 is then withdrawn from the target tissue site to the exterior of the body.

The tissue specimen is removed from the needle assembly 100 by first moving the second carriage assembly 264 from its second position to a third position by returning the second carriage assembly 264 to its first position, re-exposing the core bed 116. The tissue within the core bed 116 may then be transferred to a medium, such as a medium in a pathology specimen cassette, or into a vial with preservative, until pathological examination.

In some embodiments, the first and second firing pins 242, 276 are connected by a bridge 298. The bridge 298 operates to immediately disengage the second firing pin 276 from the second carriage assembly 264 immediately after the first carriage assembly 230 contacts the first carriage stop 238. In such an arrangement, a trigger 300 connected to the first firing pin 242 at the exterior of the body 202 is actuated to initiate the firing sequence.

In some embodiments, a safety release 312 obstructs movement of the first firing pin 242 from the engaged position to the disengaged position relative to the first carriage assembly 230. To fire the needles, the safety release 312 is moved from a position obstructing movement of the first firing pin 242 to a position that does not obstruct movement of the first firing pin 242.

Figure 14A:
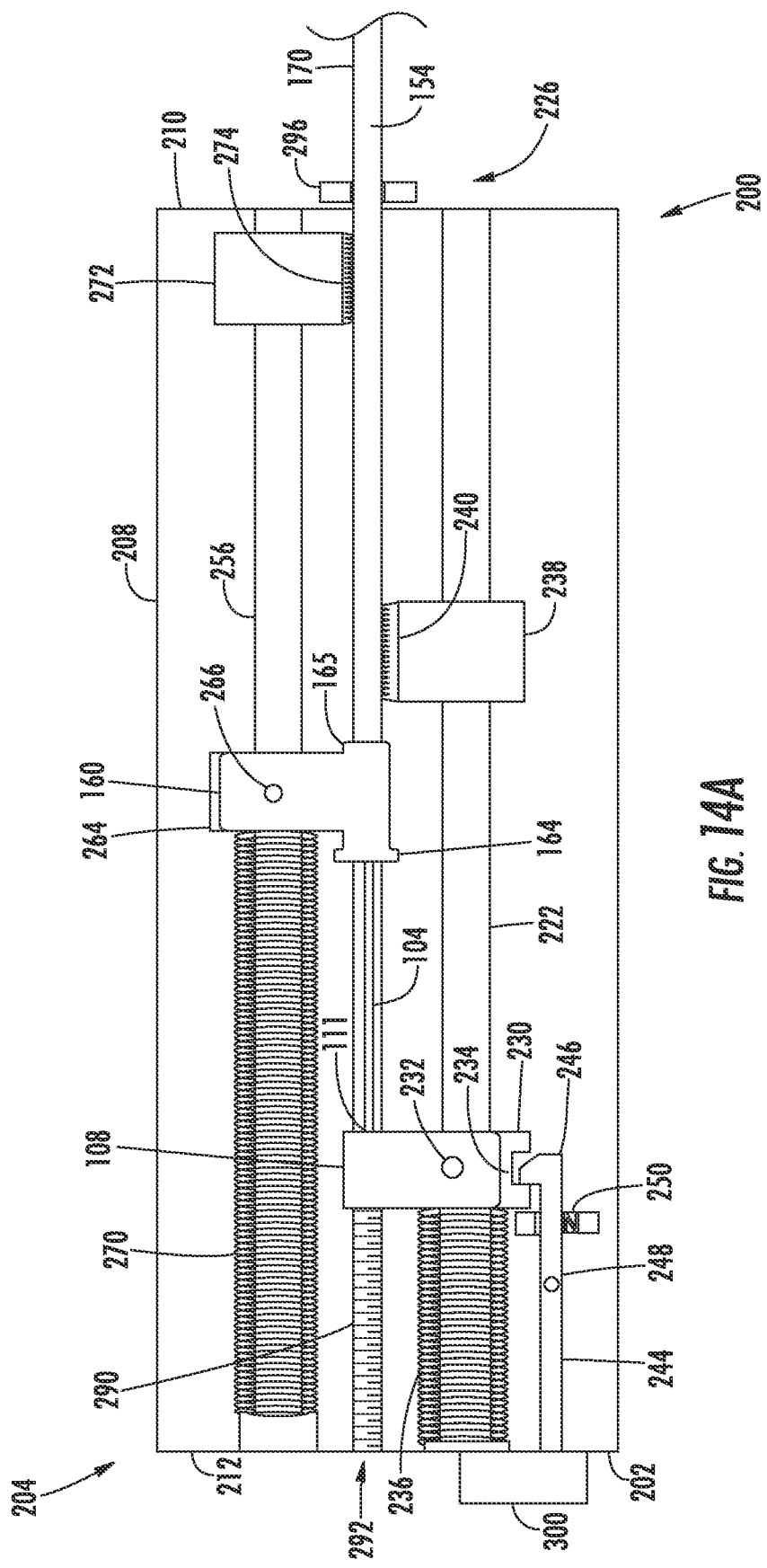
FIG. 14A is a plan view of an embodiment of an actuator assembly showing a safety release.
Figure 14B:
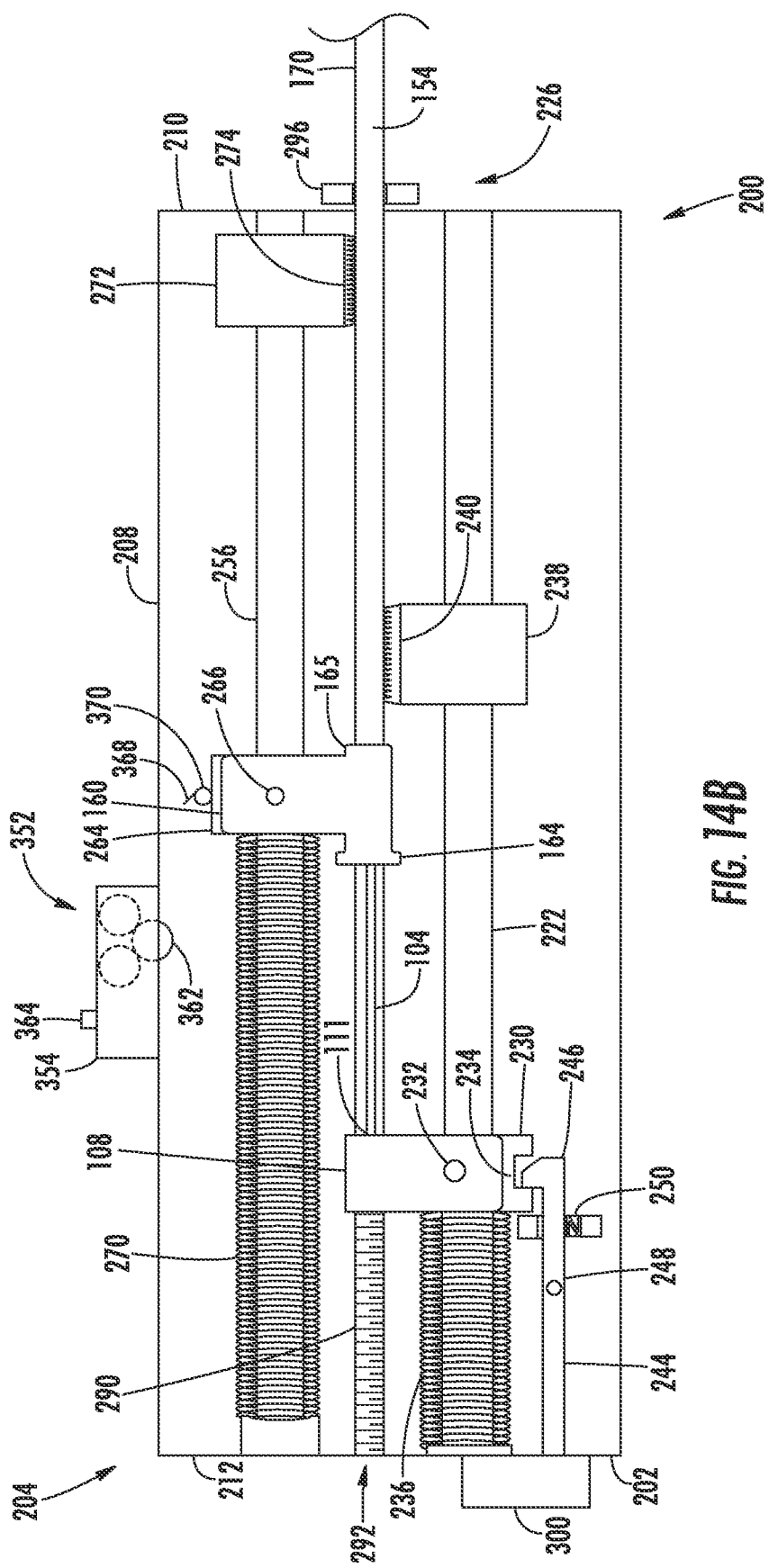
FIG. 14B is a view of an embodiment of an actuator assembly showing a counter assembly
Figure 14C:
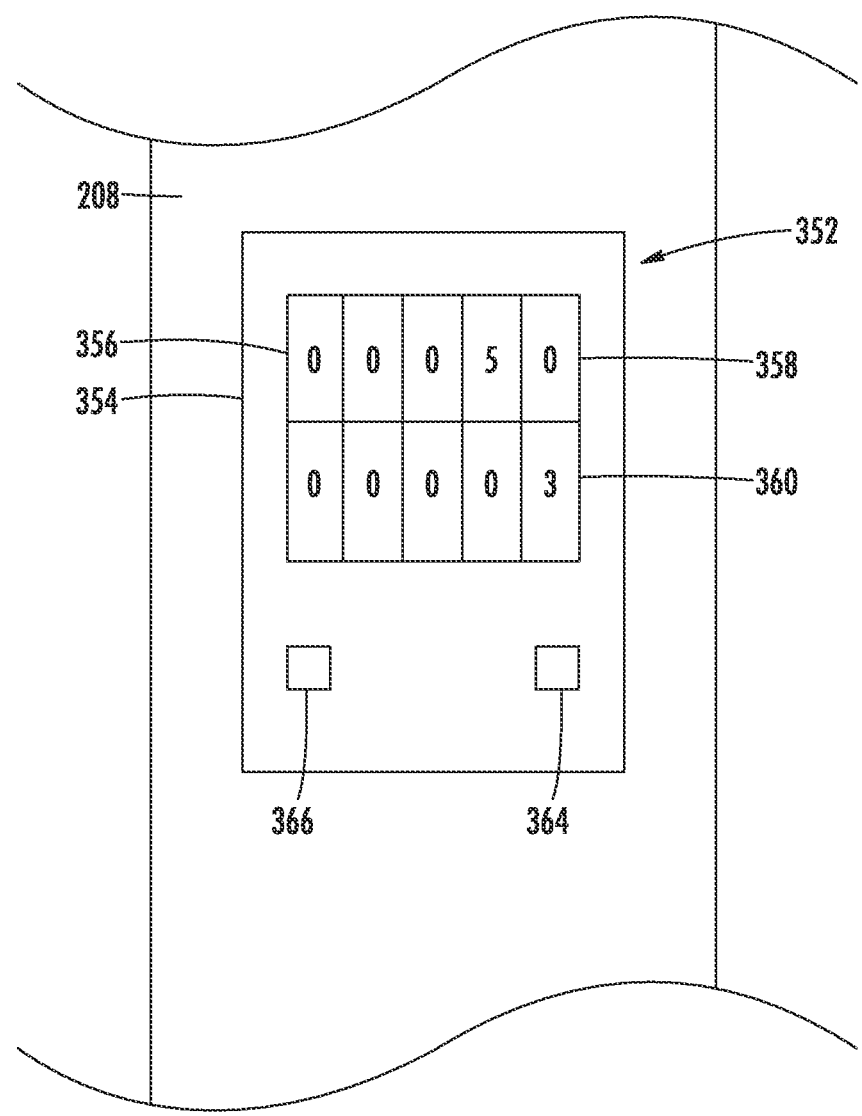
FIG. 14C is a plan view of the counter assembly.
Figure 15:
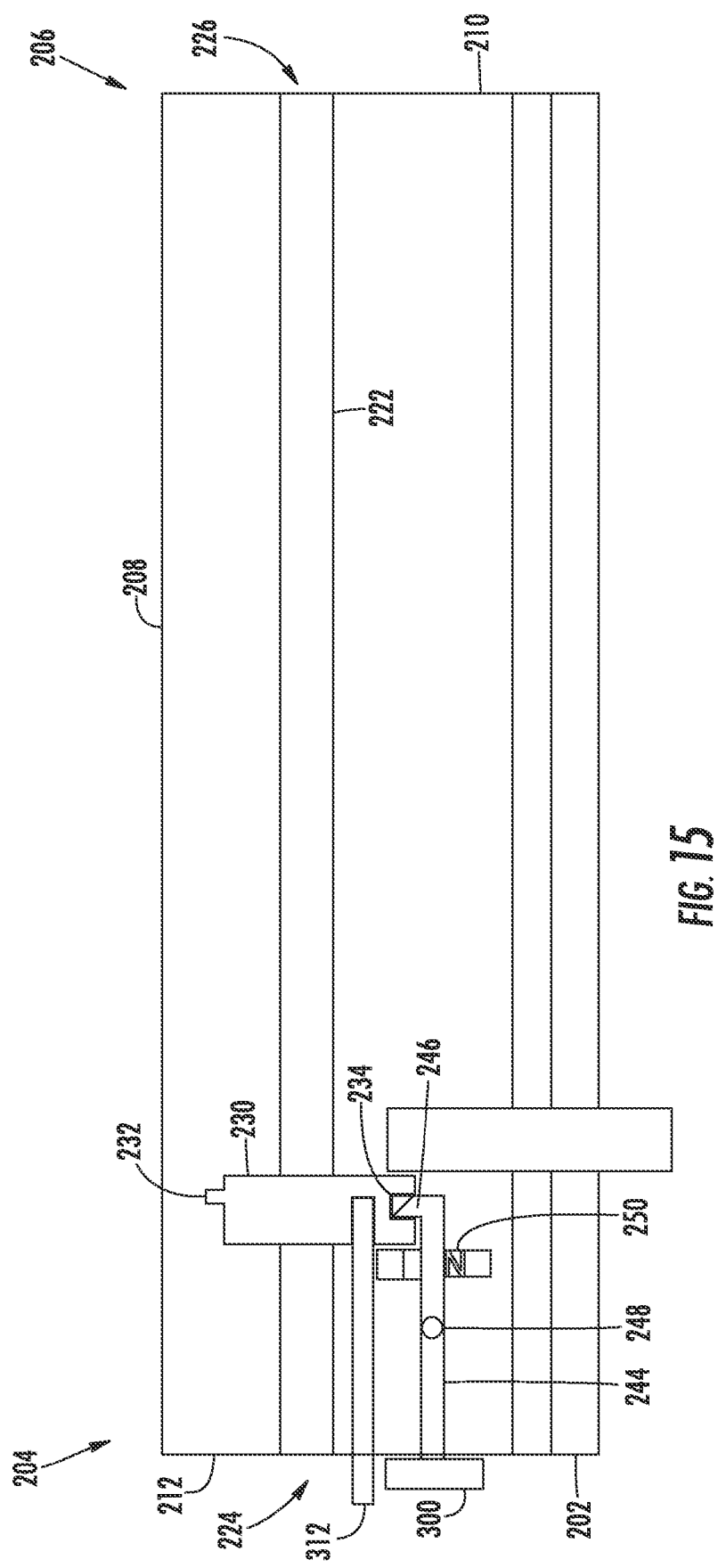
FIG. 15 is a side elevation view of an embodiment of an actuator assembly showing a safety release and a firing pin.

In some embodiments, the actuator assembly includes a counter that records the number of actuations of the biopsy needle assembly. Referring to FIGS. 14B-14C, an embodiment of a counter assembly 352 for use with the actuator assembly 200 is shown and described whereby the counter assembly 532 registers movement of the biopsy needle component connected to the second carriage assembly 264, here the outer component 152 or cannula. In an embodiment, the counter assembly 352 registers movement of the biopsy needle component connected to the first carriage assembly 230, here the inner component 102 or mandrel.

The counter assembly 352 includes a cumulative counter 358 and a resettable event counter 360. The counters each comprise a row of index wheels with numbers visible through an opening 356 in a housing 354, whereby the wheels are operably connected to a register wheel 362 within the actuator assembly 200. In an embodiment, the wheel 362 is configured to register unidirectional movement of the biopsy needle assembly. In an embodiment, the wheel 362 includes a toothed exterior that contacts the end of a lever 368 connected to the second carriage assembly 264, where the lever 368 extends from the second carriage assembly 264 toward the rear wall of the body 202 when the second carriage assembly 264 is at the rest position. As the second carriage assembly 264 moves from rest to its first position or firing position, the lever 368 contacts and rotates the wheel 362 rotating an index wheel of the cumulative counter 358 and event counter 360, advancing and increasing the numerical value of the counter by one whole number. A biasing member 370 or spring extends the lever 368 into the path of the wheel 362 when the second carriage assembly 264 is moved from rest to the first position. Upon the firing or movement of the second carriage assembly 264 from the first position to a second position, the biasing member 370 allows the lever 368 to move away from the wheel 362 and to pass by the wheel 362 without arresting movement of the second carriage assembly 264. Thus the firing of the cannula is recorded by each arming of the actuator assembly 200. A bypass 364 button is adapted for allowing the carriage assembly 264 to move from rest to the first position without advancing event counter 360. In an embodiment, the wheel 362 is moved out of the path of lever 368 to avoid rotating the wheel 362 or an index wheel. Allowing a biopsy to be taken without advancing the event counter 360 is useful when an operator desires to excise an additional tissue specimen from a target tissue from the same sample site. Upon completion of a biopsy procedure, the event counter 360 can be resent to zero by actuation of the event counter reset 366 button.

The cumulative counter 358 records the cumulative number of firings of the cannula, and the event counter 360 simultaneously records each arming of the actuator assembly 200. Tracking the cumulative number of firings of the cannula with the cumulative counter 358 is important to ensure the actuator assembly is used for no more than the manufacturer's recommendation number of biopsy events, thereby decreasing the likelihood the actuator assembly would be used under conditions whereby the mechanical components of the device would malfunction during a biopsy procedure due to use beyond its recommended number of firings. In an embodiment, the cumulative counter 358 engages a lockout device that prevents actuation of the carriage assemblies 230, 264 when the counter 358 reaches a number specified by the manufacturer, thereby requiring return or servicing of the actuator assembly.

Tracking the number of firings of the cannula with the event counter 360 is important to ensure the operator properly accounts for each biopsy event during a biopsy procedure. For example, an operator using an actuator assembly with the three-dimensional tissue mapping system below can correlate actuator assembly in use and the value represented by the event counter 360, with the location of the biopsy needle in the template 1018 and biopsy site number assigned by the software. For example, if the biopsy site number assigned by the software indicates the next biopsy event is biopsy number fifteen, the operator ensures they are holding an actuator that is ready for firing, and the event counter 360 presents the number "15" in the opening 356.

In an embodiment, the counter assembly 352 includes a firing detector that registers the firing of the cannula, the actuator in use, the value of the cumulative counter 358, and the value of the event counter 360, and transmits a data signal to a device or system external to the actuator assembly 200 for registering the data. In an embodiment, the system external to the actuator assembly 200 is the three-dimensional imaging system 1102 discussed below.

In an embodiment, the firing detector includes the wireless transmission of the data signal from the actuator assembly 200 to the imaging system 1102. In an embodiment, the firing detector includes circuitry connecting a processor, a power source, a firing sensor, a cumulative counter sensor, an event counter sensor, a memory, and a transceiver. The firing sensor detects the firing of the cannula and sends a signal to the processor. The cumulative counter sensor detects the numerical value represented by the cumulative counter and sends a signal to the processor. The event counter sensor detects the numerical value represented by the event counter and sends a signal to the processor. The memory includes the unique ID of the actuator assembly, instructions for processing the signals received by the processor, and instructions for transmitting the data signal from the actuator assembly 200 to the imaging system 1102 using the transceiver.

In use, an operator prepares to use an actuator assembly, for example an actuator assembly with the unique ID of "A-01," with a cumulative counter value of "52," an event counter value of "3," and the cannula carriage assembly at rest. The operator moves the carriage assembly from the rest position to the firing position, actuating the cumulative counter 358 and changing the value from "52" to "53," and actuating the event counter 360 and changing the value from "3" to "4." The firing detector registers the new counter values and communicates the values and the unique actuator assembly device ID A-01 to the imaging system 1102 where the information is registered as associated with biopsy number 4. Upon firing of the cannula, the sensor detects the firing of the cannula and sends a data signal to the imaging system 1102 where the information is registered as associated with biopsy number 4.

In an embodiment, the operator alternates use of two actuator assemblies, each with a unique device ID, to conduct a biopsy procedure, where the value of the event counter is staggered so that the alternating use of the actuators corresponds to a sequential progression of numerical values.

Referring to FIG. 14C, an embodiment of the actuator assembly 200 includes a lever 338 forming an ergonomic handle at the bottom or posterior of the actuator assembly 200, operably connected to the actuator members 220, 254 for moving the actuator members 220, 254 from rest to the first position. In addition, the lever 338 may be formed to fit comfortably in the hand of the operator whereby the lever 338 induces the operator to orientate the needle assembly 100 loaded therein to present the core bed 116 in the proper direction. In an embodiment, the actuator assembly 200 orientates the core bed 116 upward. In an embodiment, the actuator assembly 200 orientates the core bed 116 downward. By dictating the orientation of the core bed 116 the operator is able to correlate the subsequent pathological characteristics of the tissue specimen to the target tissue. Such correlation is enhanced by use of a needle assembly employing one or more projections 122, 128, and marking agents, as described above.

In an embodiment, the actuator assembly 200 includes a bubble level assembly on its upper surface providing an indication to a user during use that the actuator assembly 200, and thereby the needle assembly 100, is level and plumb, and not obliquely orientated thereby creating a misalignment of the biopsy tissue specimen excised from the target tissue.

It will be appreciated that the components of the actuator assembly 200 can be used for various other applications. Moreover, the actuator assembly 200 can be fabricated in various sizes and from a wide range of suitable materials, using various manufacturing and fabrication techniques.

Pathology Specimen Cassette

Referring to FIGS. 19-27, a pathology specimen cassette for retaining a biopsy tissue specimen, such as a tissue specimen obtained using the needle assembly 100, includes a cartridge assembly 400 having a media 478 retained between a base 402 and a lid 430. The biopsy specimen is applied to the media 478 and retained within the closed cartridge assembly 400 until the biopsy specimen is removed for pathological examination.

The base 402 includes sidewalls 410 forming a generally rectangular body 404 extending between a front wall 405 at a first end 406 and a back wall 407 at a second end 408. The body 404 forms a cavity 414 that is bound by an inner surface 411 of walls 405, 407, 410, a top surface 424 of a lower wall 422. The cavity 414 can be from about 5 mm to about 30 mm in width between the sidewalls 410, and from about 10 mm to about 100 mm in length between the front wall 405 and back wall 407. The cavity 414 is open at the top, and is intermittently open at the bottom by way of one or more openings 428 passing through the top surface 424 and a bottom surface 426 of the lower wall 422. The openings 428 allow fluids to move in and out of the closed cartridge assembly 400. In some embodiments the body 404 forms a hinge element 416 at the first end 406 allowing movable connection of the lid 430 to the base 402. In some embodiments the body 404 forms a lip 418 that extends outward from the second end 408 and includes an outwardly-open notch 420 for receiving a latch 472 connected to the lid 430.

The lid 430 includes sidewalls 438 forming a generally rectangular body 432 extending between a first end 434 and a second end 436. The body 432 includes a middle wall 454 with a lower wall 440, a lip 448, and an upper wall 462 extending therefrom. The middle wall 432 extends between the sidewalls 438 and the first and second ends 434, 436 forming one or more openings 460 extending between a bottom surface 456 and a top surface 458. The openings 460 allow fluids to move into and out of the closed cartridge assembly 400. The lower wall 440 depends from the bottom surface 456 and extends between the sides and the first and second ends 434, 436, forming a bottom surface 422, and inner surface 444, and an outer surface 446. The inner surface 444 forms a cavity that is open at the bottom, and is bound by the lower wall 440 at the first end 434, second end 436, sides, and the bottom surface 456. A lip 448 extends outward from the middle wall 454 forming a bottom surface 450 and a top surface 452. The upper wall 462 extends upward from top surfaces 458 and 452 forming a top surface 465.

Figure 20:
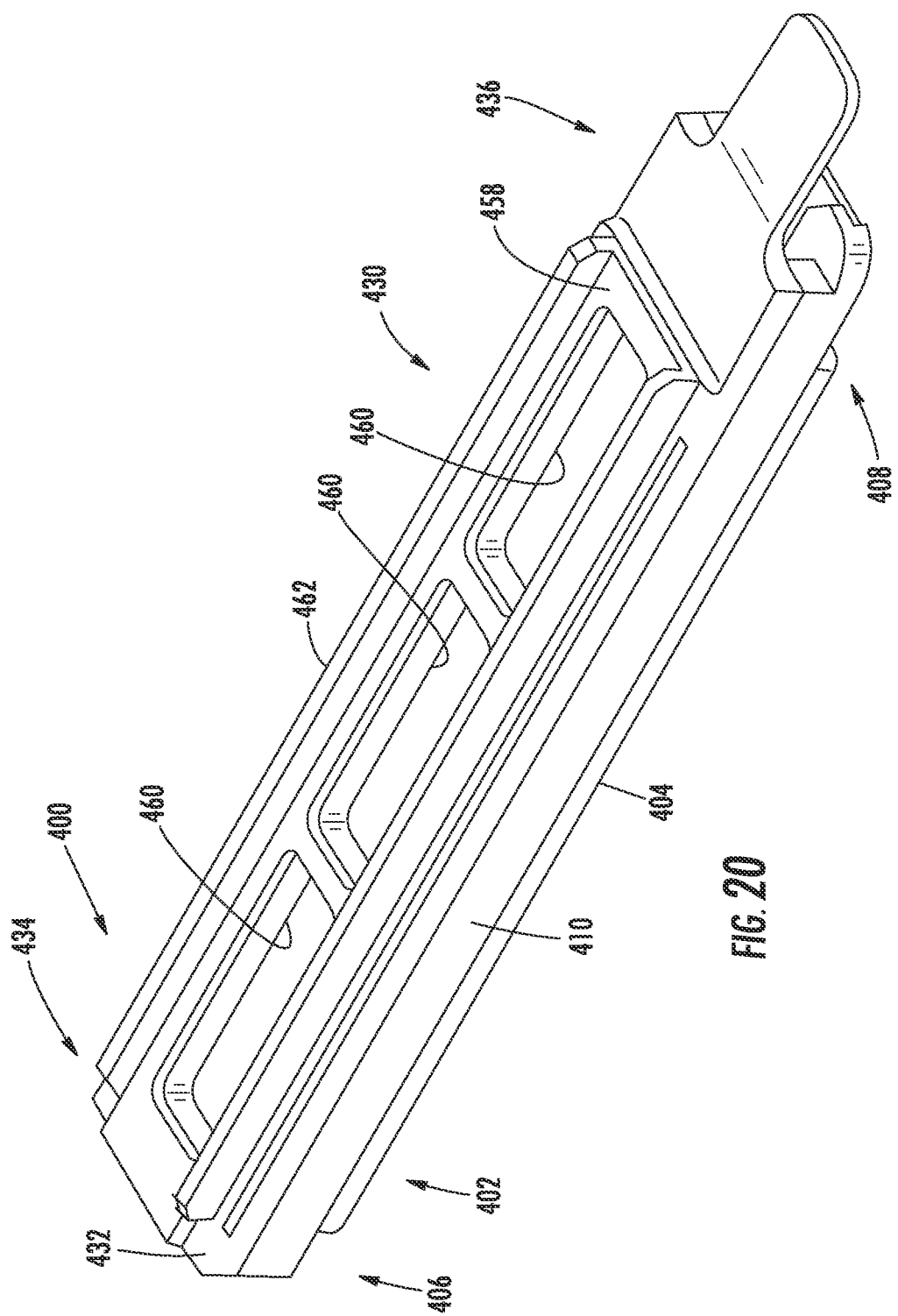
FIG. 20 is an isometric view of an embodiment of a cartridge assembly in a closed position.
Figure 21:
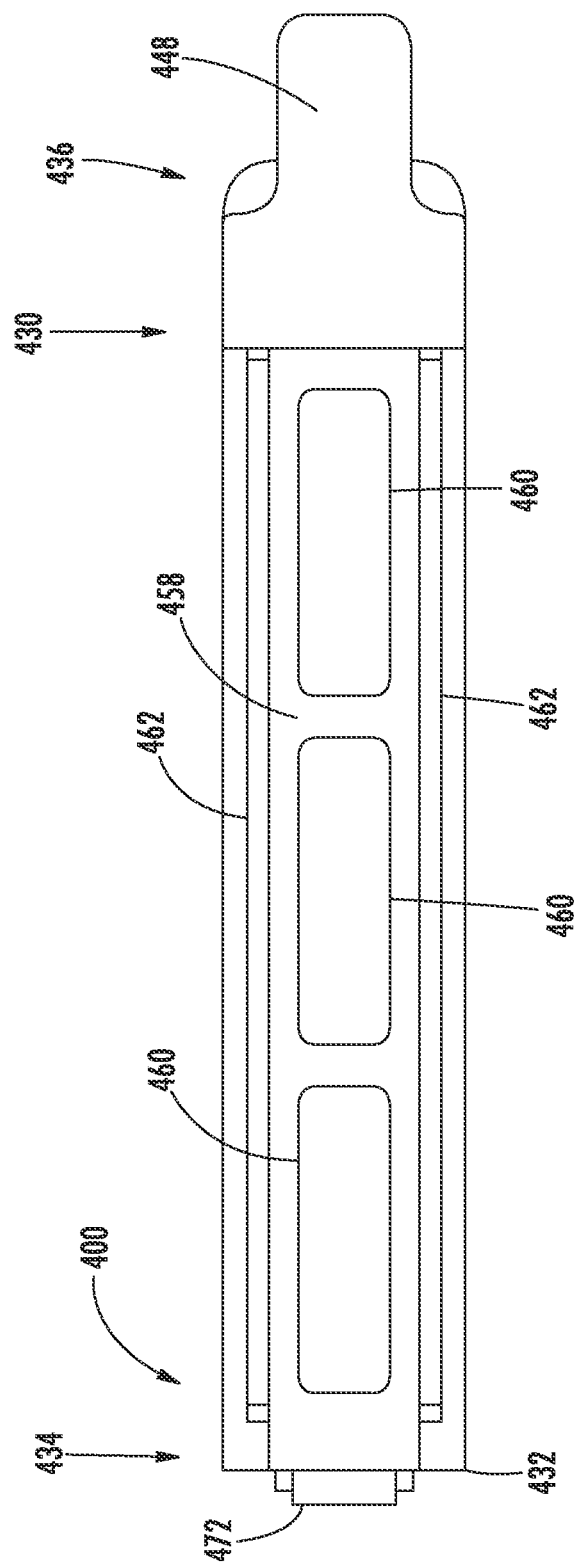
FIG. 21 is a plan view of an embodiment of the cartridge assembly of FIG. 20.
Figure 22:
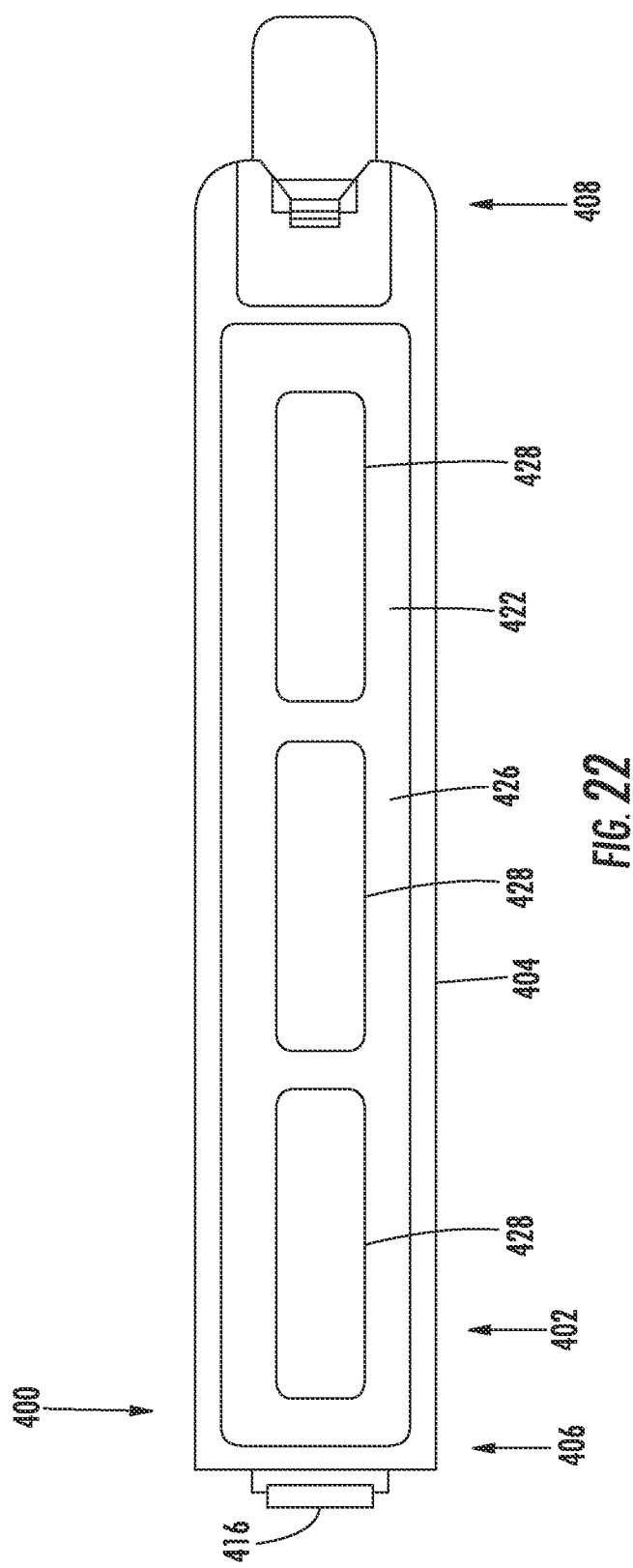
FIG. 22 is a bottom view of the cartridge assembly of FIG. 20.
Figure 23:
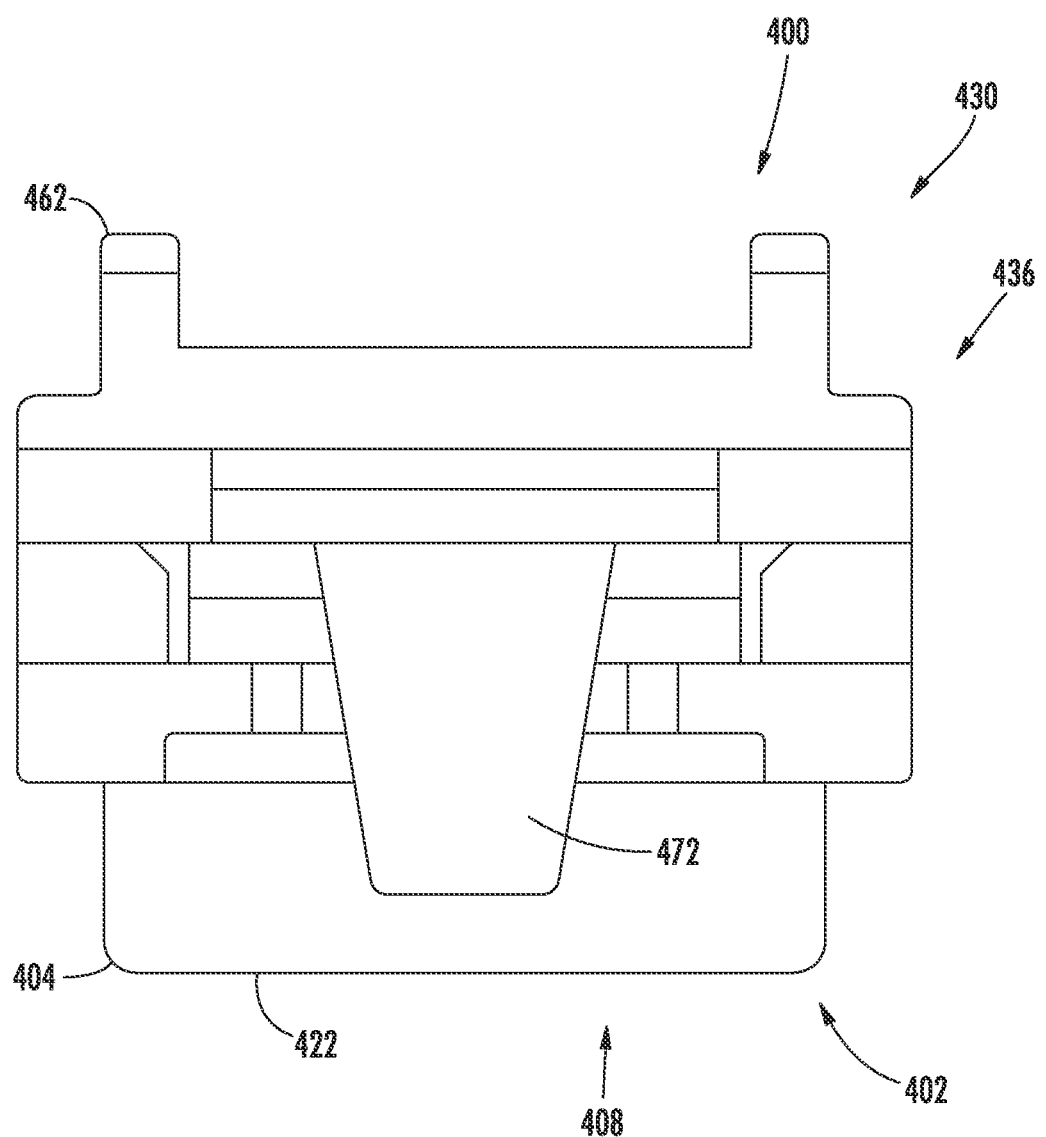
FIG. 23 is a front elevation view of the cartridge assembly of FIG. 20.
Figure 24:
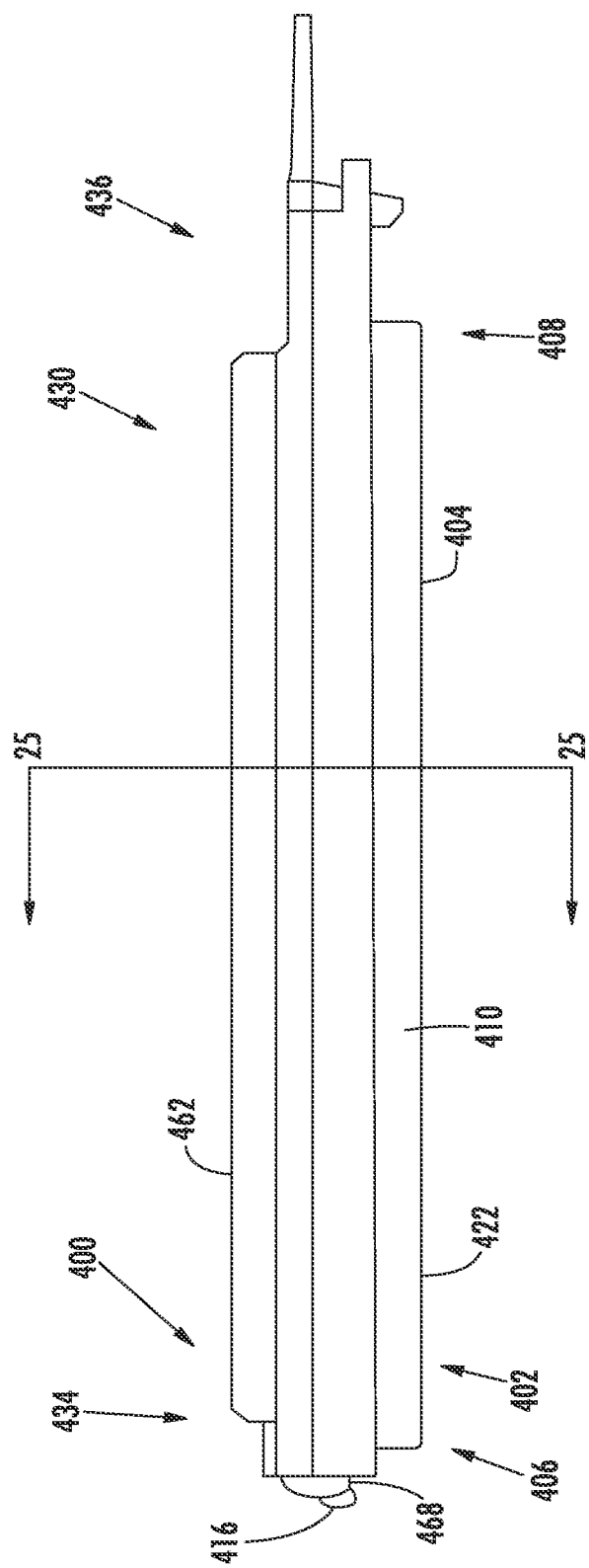
FIG. 24 is a side elevation view of the cartridge assembly of FIG. 20.

In some embodiments, the body 432 forms a hinge element 468 at the first end 434 that cooperates with hinge element 416 allowing movable connection of the base 402 to the lid 430, thereby securing the base 402 to the lid 430 when the cartridge assembly 400 is in an open position (FIG. 19) or closed position (FIG. 20). In some embodiments the body 432 forms a tab 470 that extends outward from the second end 436 and includes a latch 472 depending therefrom forming a protrusion 474 for engaging the notch 420, thereby securing the base 402 to the lid 430 when the cartridge assembly 400 is in a closed position.

The base 402 and lid 430 are manufactured from material, including plastic, that is resistant to corrosion, including corrosion from aqueous and non-aqueous solvents such as formaldehyde.

Figure 25:
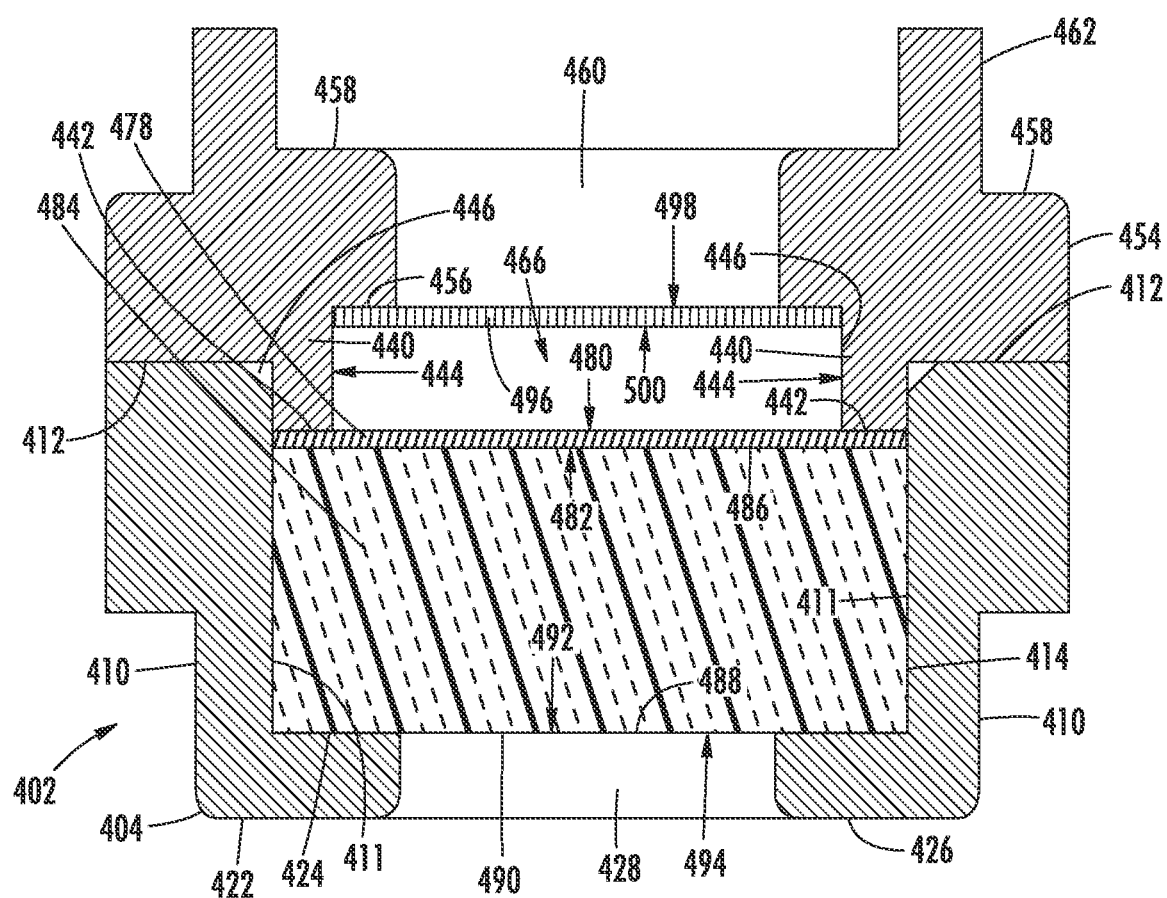
FIG. 25 is a section view taken generally along line 25-25 in FIG. 24.
Figure 26:
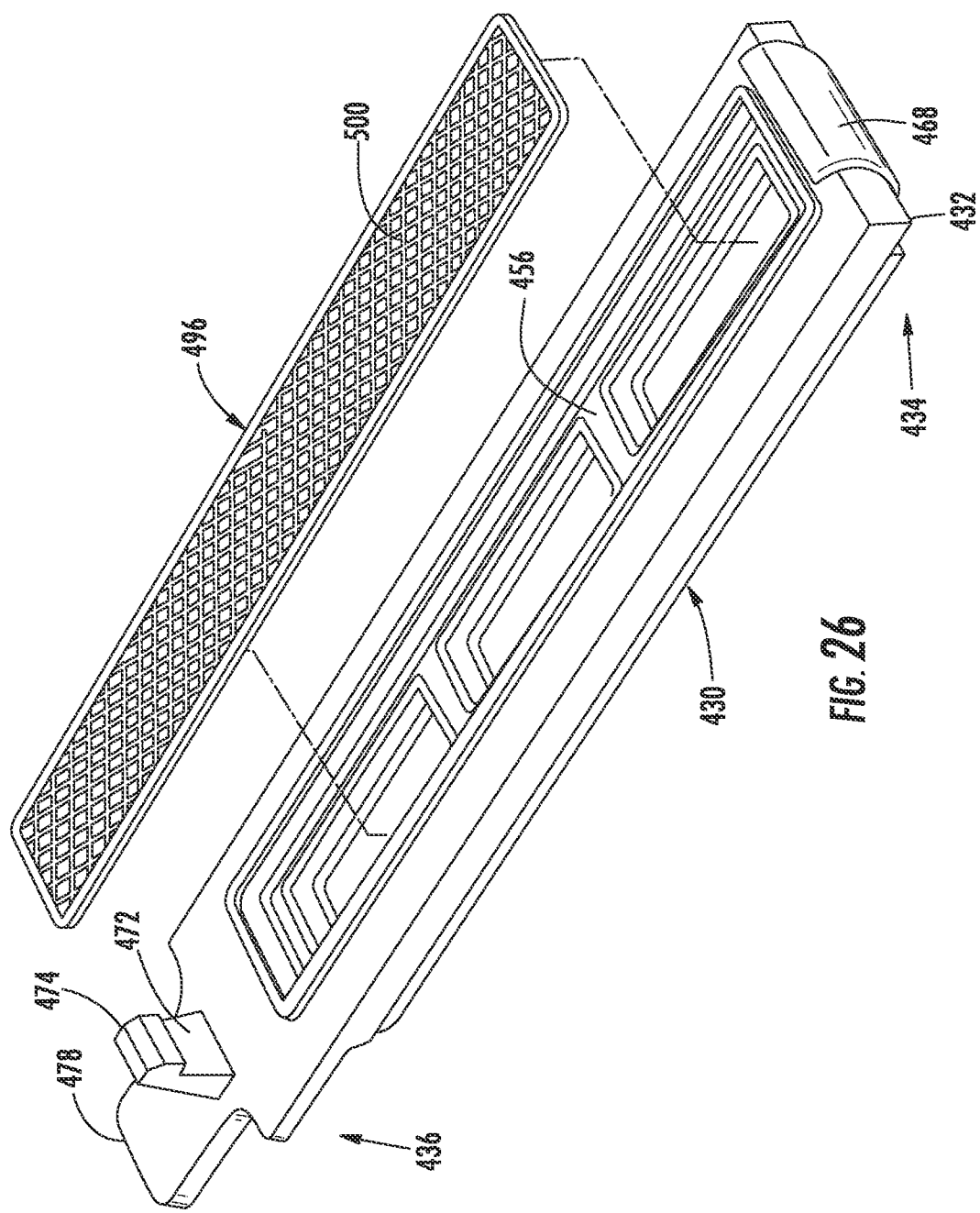
FIG. 26 is an exploded view of a lid of an embodiment of a cartridge assembly.
Figure 27:
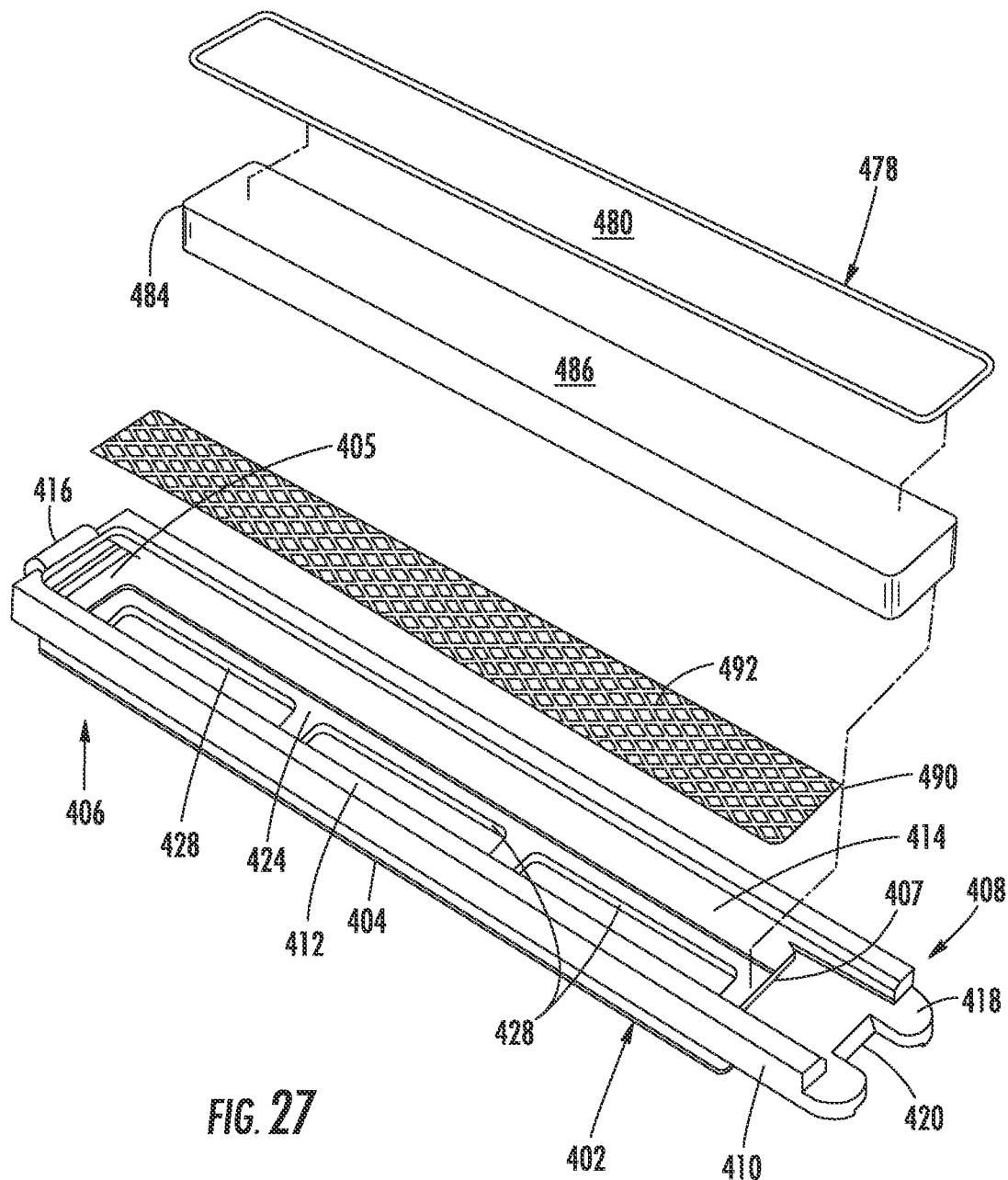
FIG. 27 is an exploded view of a base of an embodiment of a cartridge assembly.
Figure 28:
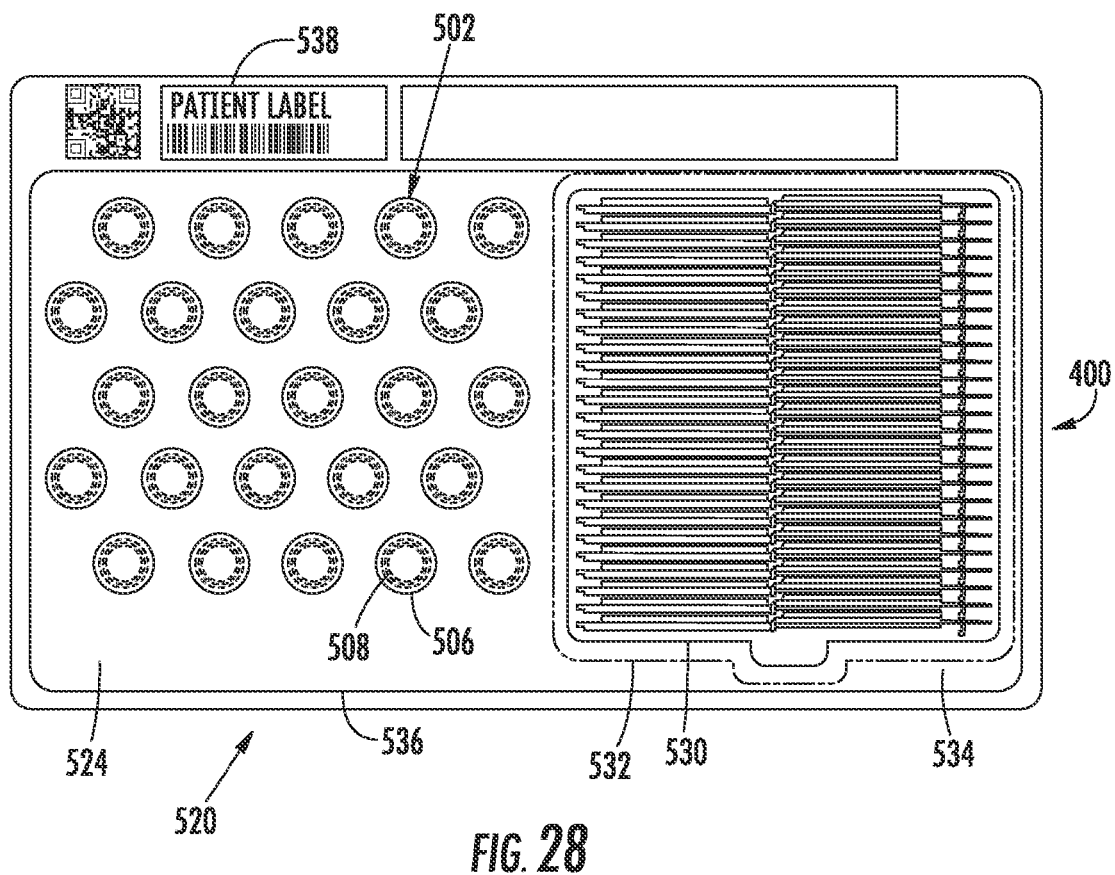
FIG. 28 is a plan view of an embodiment of a tray.
Figure 29:
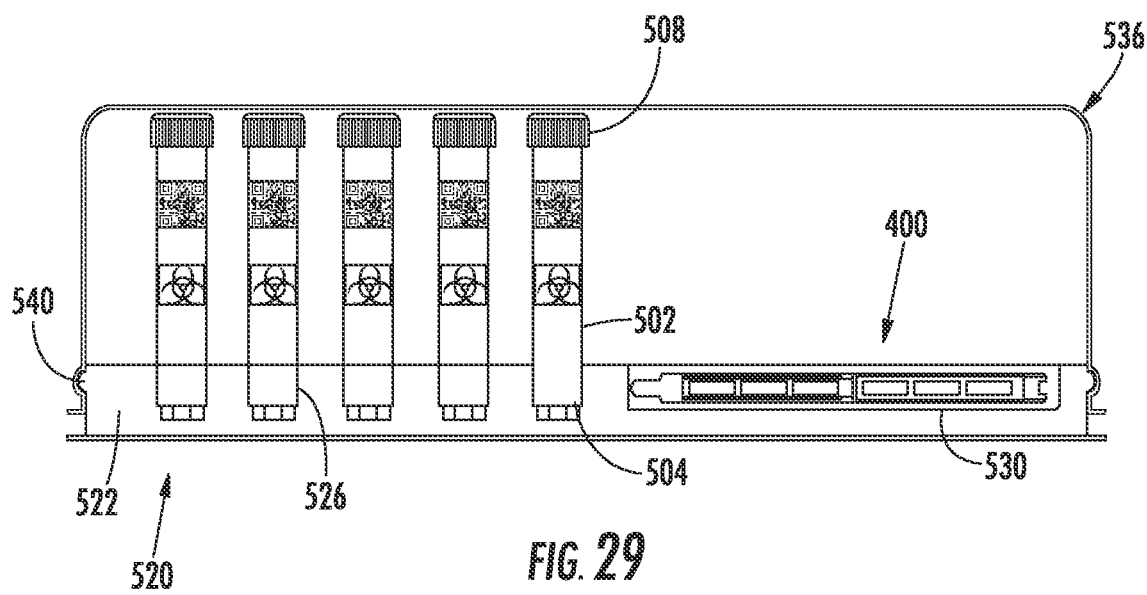
FIG. 29 is a front elevation view of an embodiment of a tray.

Referring to FIGS. 25-27, a fluid transfer element 484, bound by a media 478 and a first membrane 490, is retained within cavity 414. The fluid transfer element 484 comprising a suitable porous material, is retained within cavity 414. The fluid transfer element 484 absorbs a fluid, described further below, allowing the tissue specimen on the media 478 to be constantly immersed in the fluid. The porous material can comprise, for example, an open-cell, closed-cell, large-cell, or small cell foam material. The foam material can comprise, for example, a hydrophilic material, a hydrophobic material, polyurethane ester, polyvinyl acetate, and rubber. The fluid transfer element 484 includes a top surface 486 and a bottom surface 488.

The first membrane 490, comprises a suitable semi-permeable material for selectively admitting fluid into the cartridge assembly 400. The first membrane 490 includes a top surface 492 and a bottom surface 494. The top surface 492 is in contact with bottom surface 488, and the bottom surface 494 is in an opposing relationship with top surface 424 and exposed to openings 428.

The media 478 facilitates handling and examination of the biopsy tissue specimen during examination without a need to remove the specimen from the media 478. The media 478 includes a top surface 480 exposed to the top of the base 402 for receiving the tissue specimen, and a bottom surface 482 in contact with the top surface 486. The media 478 comprises, for example, a single material or an amalgam of materials including, cellulose filter media, plastic filter media, polymer formulations, and biopolymer formulations. The thickness of the media 478 is from about 0.1 mm to about 10 mm. The density of the media 478 includes the same density as paraffin polymers used in routine histology labs to facilitate tissue processing and sectioning through without removal of the biopsy tissue core. The media 478 may be treated to improve adherence of the tissue specimen including chemical coating or infusion, biopolymer coating or infusion, and exposure to high temperature coronal plasma. Markings, such as perforations or lines, on the top surface 480 or incorporated within the media 478, facilitate spacial orientation and location identification of the beginning and end of any lesions identified during the pathological examination, and subsequent segmentation of the media 478 and attached tissue specimen during pathological examination. In some embodiments, the markings are delineated in cm or mm increments providing a guide to the distance between the first end and second end of the tissue specimen.

A second membrane 496 is retained by cavity 466. The second membrane 496 comprises, for example, a suitable semi-permeable material for selectively admitting fluid into the cartridge assembly 400. The second membrane 496 includes a top surface 498 and a bottom surface 500. The top surface 496 is an opposing relationship with bottom surface 456 and exposed to openings 460, and the bottom surface 500 is exposed to the bottom of the lid 430.

The first and second membranes 490, 496 are manufactured from a material, including plastic, that is resistant to corrosion, including corrosion from aqueous and non-aqueous solvents such as formaldehyde.

The aforementioned features of the cartridge assembly 400 aid in a more precise examination of a biopsy tissue specimen excised from a target tissue site. Moreover, the careful orientation, transfer, and placement of a biopsy tissue core specimen from a biopsy needle to the media 478 allows an examining pathologist to accurately identify the biopsy specimen and to identify the anatomic location and orientation of the specimen in relationship to the target tissue.

In use, the cartridge assembly 400 is orientated to an open position (FIG. 19) whereby the lid 430 and base 402 are separated so that the media 478 is accessible. The biopsy tissue specimen is orientated and placed on the media 478 so that tissue located at the second end 120 of the core bed 116 is adjacent the first end 406 of the base 402, and the tissue located at the first end 118 of the core bed 116 is adjacent the second end 408 of the base 402. Any markings made on the tissues by the projections or marking agents may additionally facilitate orientation and identification of the tissue specimen. In some embodiments, the cartridge assembly 400 may be labeled to indicate the proper orientation of the biopsy needle. In some embodiments, the base of the tissue is marked with a pathological compatible ink allowing the pathologist to properly determine the location of any lesions on the specimen, and in turn, lesions in the target tissue. Once the biopsy tissue specimen is in contact with the media 476 the cartridge assembly 400 is orientated to a closed position (FIG. 20) whereby the lid 430 and base 402 are joined, effectively capturing the specimen there between. In the closed position, top surface 424 and bottom surface 450 are in an opposing relationship, and bottom surface 442 and top surface 480 are in an opposing relationship. In some embodiments, the protrusion 474 engages the notch 420 securing the base 402 to the lid 430. The closed cartridge assembly 400 with tissue specimen is then placed in a collection vial 502 containing a fluid, including a preservative, until the cartridge assembly 400 is removed prior to pathological examination. At the time of pathological examination, the cartridge assembly 400 is orientated in an opened position and the media 478 with the tissue specimen is removed for examination.

Referring to FIGS. 28-32, the collection vial 502 has a sidewall forming an upwardly open cylinder extending from a lower closed bottom 504 to an upper opening 506. The vial includes a cap 508 that creates a sealing relationship with the vial 502. In use, a vial 502 is selected having a length, and a diameter greater than the largest cross-sectional dimension and length of the selected closed cartridge assembly 400. The cap 508 is removed and the first end 406 of the closed cartridge assembly 400 containing a tissue specimen is inserted into the vial 502 until it is at the base 504. The vial 502 may include a preservative prior to insertion of the cartridge assembly 400, or a preservative may be added after insertion of the cartridge assembly 400. The cap 508 is replaced and the vial 502 remains sealed until pathological examination. In some embodiments, a label providing is applied to the vial 502 including information associating the specimens as belonging to an individual patient In some embodiments, a plurality of vials 502 and a plurality of cartridge assemblies 400 may be assembled in a collection tray 520 (FIGS. 28-32). The tray 520 includes a vacuum formed base with a plurality of vial wells 526 in an upper surface 524, and an adjacent cartridge assembly well 530. The tray 520 may be manufactured from plastic and plastic copolymers. The vial wells 526 are dimensioned to receive the bottom 504 of a corresponding vial 502 so that the vial 502 is supported in an upright position. The cartridge assembly well 530 is dimensioned to receive a plurality of cartridge assemblies 400 in an open position. The cartridge assemblies 400 may be sterile, and the cartridge assembly well 530 is bound by a sealing surface 534 for receiving a seal 532 for retaining the cartridge assemblies 400 in a sterile environment therein. One or more labels 538 on the tray 520 provide information identifying the specimens in the vials 502 as belonging to an individual patient. The tray 520 includes a vertical sidewall 522 at its base. The sidewall 522 includes a sealing surface 540 for engaging a cover 536, such as in a labyrinth seal arrangement, for retaining the vials 502 in a sterile environment therein and for containing spills. In some embodiments the tray 520, vials 502, and cartridge assemblies 400 are enveloped by a plastic bag 542 and sealed therein for retaining a sterile environment therein and for containing spills.

Common biopsy procedures may require at least twenty biopsy tissue specimens to adequately sample a target tissue. In some embodiments, the collection tray 520 includes twenty five vials 502 and twenty five cartridge assemblies 400. In some embodiments the vials are pre-filled with 10 percent neutral buffered formalin.

In some embodiments, a printer connected to software being used in conjunction with performing the biopsy will print a label adapted for application to the vials 502 for identifying the specimen contained therein. The label may include patient identifying information, including a specimen identification number and associated patient record data. Each vial 502 containing a tissue specimen receives a unique identification number allowing the specimen to be associated with a biopsy site. Providing a unique identification number will greatly minimize specimen labeling mistakes and facilitate incorporation of remarks related to the pathological findings into biopsy mapping software.

Upon pathological examination, the distal end or base of each tissue specimen will be marked with tissue marking dye of a color. Each subsequent length of tissue, from about 10 mm to about 15 mm may be marked with a different color of tissue marking dye. The tissue specimen and the media 478 are sectioned, such as with a dissection blade. The tissue and media 478 segments will be placed into a labeled histopathology cassette for subsequent tissue processing according to standard histopathology practice. For media 478 of higher density than paraffin, the tissue specimens are removed from the media 478 when orientating and embedding the tissue specimens on the histopathology cassette.

It will be appreciated that the components of the cartridge assembly 400 can be used for various other applications. Moreover, the cartridge assembly 400 can be fabricated in various sizes and from a wide range of suitable materials, using various manufacturing and fabrication techniques.

Three-Dimensional Mapping and Focal Therapy System and Method

Embodiments of the disclosed subject matter include systems, methods, and apparatus that are improvements to the field of planning and performing biopsies. Some embodiments of the disclosed subject matter include systems, methods, and apparatus for a three-dimensional imaging system 1102 providing advantages in the imaging and mapping of a target tissue for planning and performing biopsies of the target tissue, and for planning and performing treatments of the target tissue. The three-dimensional imaging and mapping of a target tissues provides a technological benefit of a higher degree of accuracy of sampling tissue specimens and reconstruction of the location and mass of lesions of the target tissue thereby providing for a higher degree of accuracy of the identification of the existing pathology of the target tissue and allowing a more accurate identification of appropriate therapies for patient treatment. The disclosed subject matter can be used with any manner of target tissue types, including human tissues.

FIG. 33 illustrates a patient 1002 positioned for a procedure, specifically a procedure where the target tissue is a prostate gland. The patient 1002 is in a lithotomy position on a procedure table whereby the prostate gland is accessed in a transperineal manner. In the representative embodiment, the biopsy of the prostate is performed with the aid of a grid or template 1018 positioned adjacent the perineum of the patient 1002. An imaging system 1032, such as an ultrasound system 1034 with a transrectal ultrasound (TRUS) probe 1036 is used to provide transverse and sagittal images of the target tissue on a graphical user interface (GUI) 1104. The relative position between the probe 1036 and the template 1018 is known allowing for a correlation between the image produced by the TRUS probe 1036 and the position of the template 1018. The template 1018 is connected to a mount 1026, and the probe 1036 is connected to the mount 1026 by an index mechanism 1028 such as a stepper system. The mount 1026 provides for proper support and positioning of the template 1018 and probe 1036, and the index mechanism 1028 provides for registered movement of the probe 1036 allowing the imaging system 1032 to acquire images of the prostate that are a fixed distance apart.

Once the patient 1002 is positioned to begin the procedure, the system 1102 can be used to acquire images of a target tissue for planning a biopsy procedure, conducting the biopsy procedure and obtaining tissue specimens, correlating pathology results of the tissue specimens to a virtual and ultrasound image of the target tissue, and plan and implement treatments of the target tissue.

Figure 34:
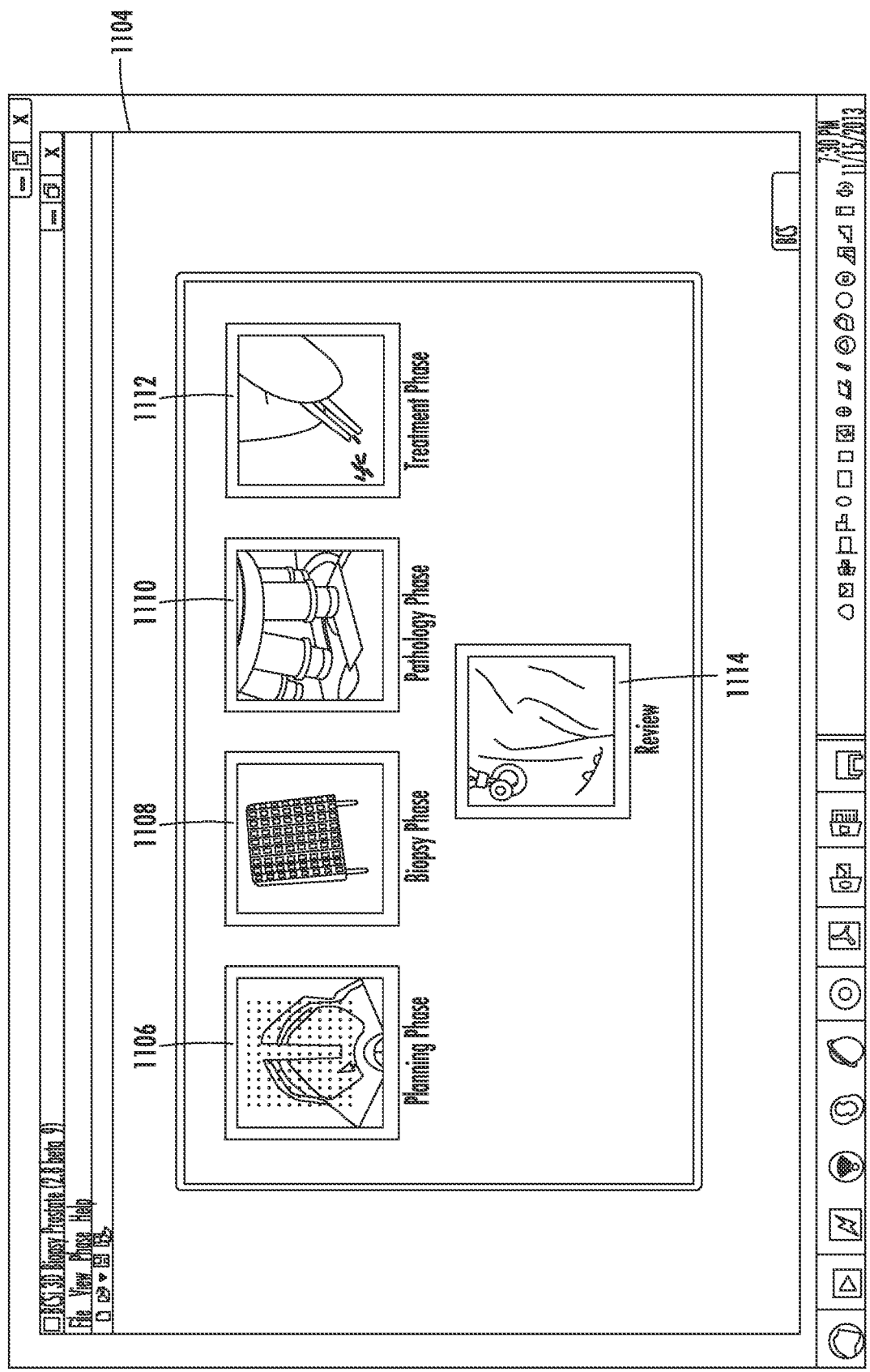
FIG. 34 is an illustration of a graphical user interface according to some embodiments of the disclosed subject matter for selecting a module.

FIG. 34 illustrates an example of a GUI 1104 according to some embodiments of the system 1102. The GUI 1104 displays a list of modules performed by the system 1102 pertaining to the several phases of the system 1102. Specifically, FIG. 34 illustrates five modules: a planning module 1106 for a planning phase, a biopsy module 1108 for a biopsy phase, a pathology module 1110 for a pathology phase, a treatment module 1112 for a treatment phase, and a review module 1114 for a review phase.

Planning Phase

The planning module 1106 allows a user to obtain ultrasound images of the target tissue, align the hardware used to obtain biopsy specimens with the ultrasound images, construct a three-dimensional image of the target tissue, and prepare a plan for obtaining biopsy tissue specimens of the target tissue. The three-dimensional imaging system improves the biopsy procedure by allowing an operator to generate a biopsy site plan from a three-dimensional model of the prostate.

Figure 35:
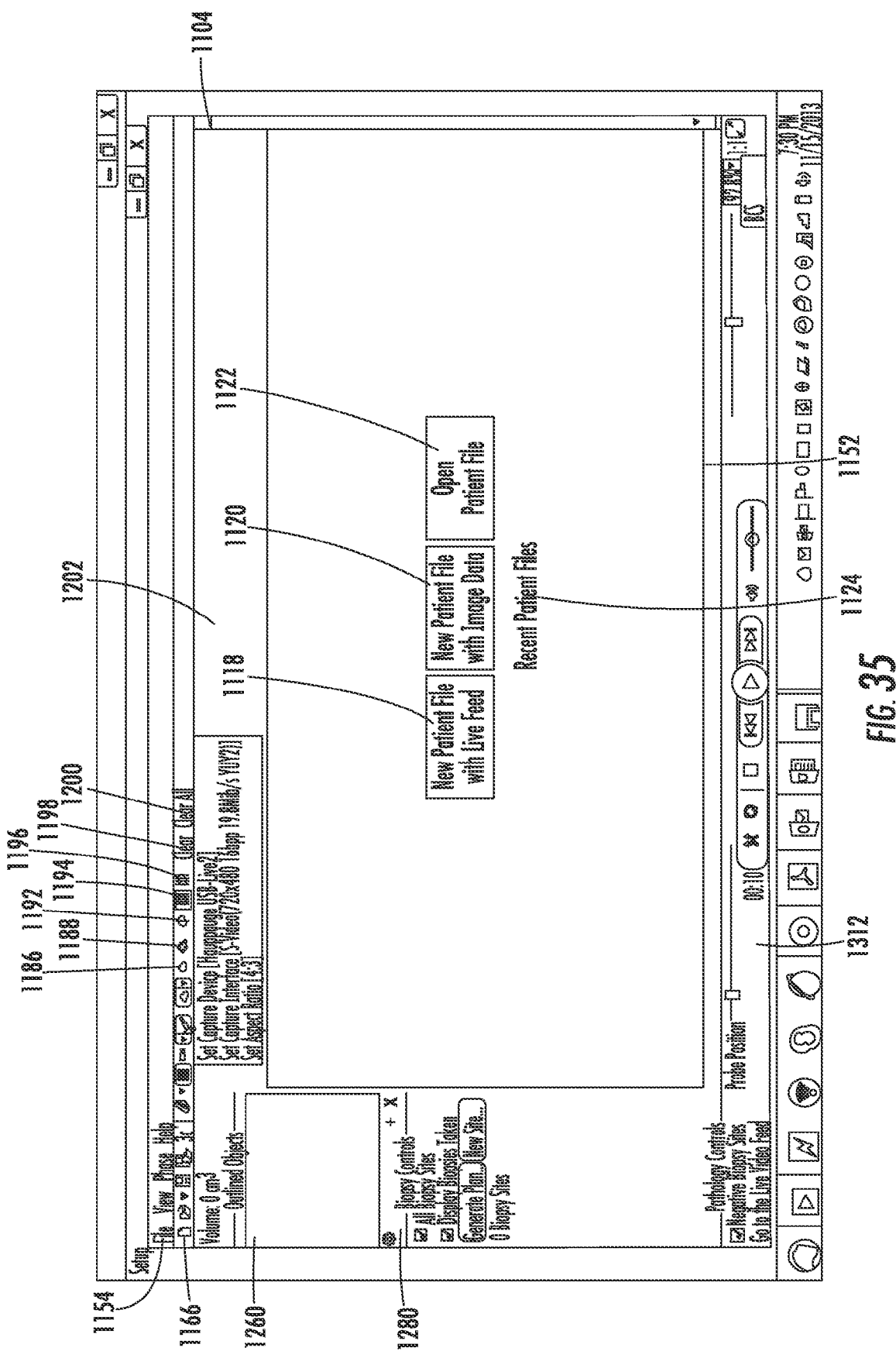
FIG. 35 is an illustration of a graphical user interface according to some embodiments of the disclosed subject matter for creating and accessing patient files.

FIG. 35 illustrates an exemplary embodiment of a graphical user interface used for creating new patient files and for accessing existing patient files. The GUI 1104 includes an image frame 1152: bound at the top by a menu bar 1154, a tool bar 1166, a thumbnail frame 1202; bound at the side by a preview frame 1228, an outline object structure frame 1260, a biopsy control frame 1280, and a pathology control frame 1302; and bound below by an image control frame 1312.

The image frame 1152 displays the interactive icons, and interactive images of the biopsy plan. The interactive icons include creating a new patient file with a real-time image data 1118, a new patient file with existing image data 1120, access to existing patient files 1122, and access to recent patient files 1124. The following example of the functionality of the system 1102 is first shown and described in an embodiment where the user selects creating a new patient file with a real-time image data 1118 in the planning module 1106.

The menu bar 1154 includes menu items that provide access to file, view, phase, and help functionality. The file 1156 menu item opens a new or existing file, adds an existing biopsy plan, imports data files from other imaging modalities and allows export of data files in various formats. The view 1158 menu item creates two-dimensional or three-dimensional views, allows for the addition of toolbars, and allows for adjustment of screen image size. The phase 1160 menu item puts the user in the planning, biopsy, pathology, or treatment phases. The help 1162 menu item includes instructions and software license information.

The tool bar 1166 includes tool buttons that provide software input and output elements. The new file 1168 button creates a new patient study or procedure. The open file 1170 button opens data files for an existing patient study or procedure. The save file 1172 button saves the active patient study or procedure. The save folder 1173 button saves the active patient study or procedure with a new name. The three-dimensional reconstruct 1174 button adds a three-dimensional view of the structures. The toggle probe dropdown button 1176 switches the views in the image frame 1152 between axial to sagittal views. The grid 1178 button brings up the software grid 1344 in the image frame 1152, allowing calibration of the software grid 1344 to the ultrasound grid 1332. The capture device dropdown 1180 button allows a user to select preferences for the capture device, including setting the capture device, setting the capture interface and frame rate, and setting the aspect ratio. In some embodiments the capture device is set as a universal serial bus (USB) image capture device. In some embodiments the capture interface is set as separate video (S-Video) at 720×480 pixel resolution, 16 bits per pixel (bpp), 19.8 mebibyte per second (Mib/s), and picture encoding YUY2. In some embodiments the aspect ratio is set at 4:3. The outline tool 1182 button allows a user to create and edit an outline or contour of a tissue or structure in the image frame 1152. The outline dropdown 1184 button allows a user to set outline details such as turn on or turn off the outline, and allows adjustment of the outline parameters, including intensity, color, size, etc. The fill outline 1186 button fills the entire outline in. The node contour 1188 button shows the outline control points and allows adjustment of the contour edge by adding nodes to the contour edge and pulling or pushing notes across the image. Notes may also be removed from the image with the noted contour 1188 button. The single outline 1192 button shows only the selected outline in the image frame 1152. The adjacent outline 1194 button shows the selected outline and any adjacent outlines in the image frame 1152. The all outlines 1196 button shows all of the saved outlines in the image frame 1152. The clear 1198 button clears the selected outline being constructed in the image frame 1152. The clear all 1200 button clears all outlines constructed in the image frame 1152.

Figure 36:
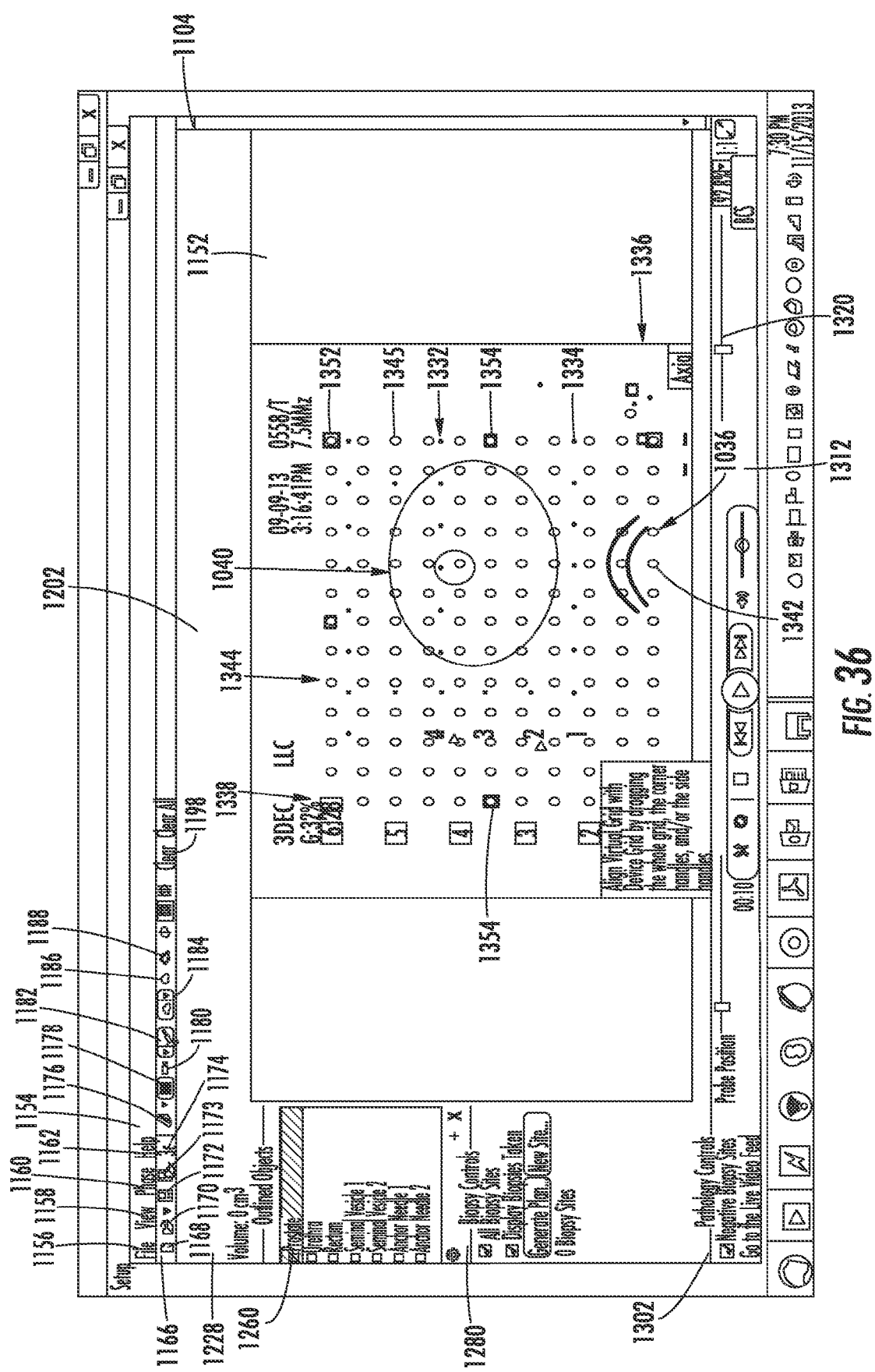
FIGS. 36-40 are illustrations of a graphical user interface according to some embodiments of the disclosed subject matter for aligning a biopsy template grid and an ultrasound grid about an image of the target tissue site.
Figure 37:
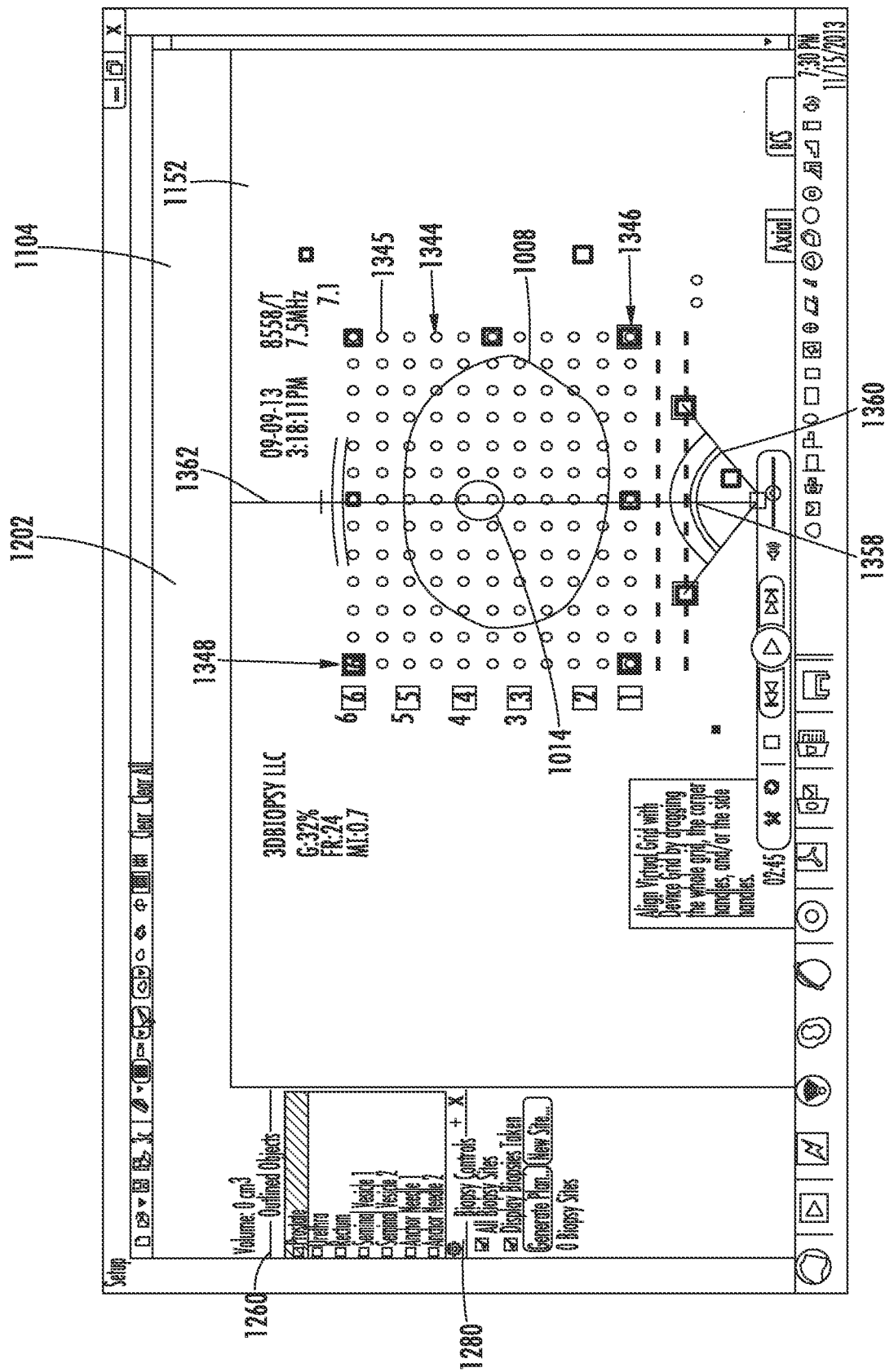
Figure 38:
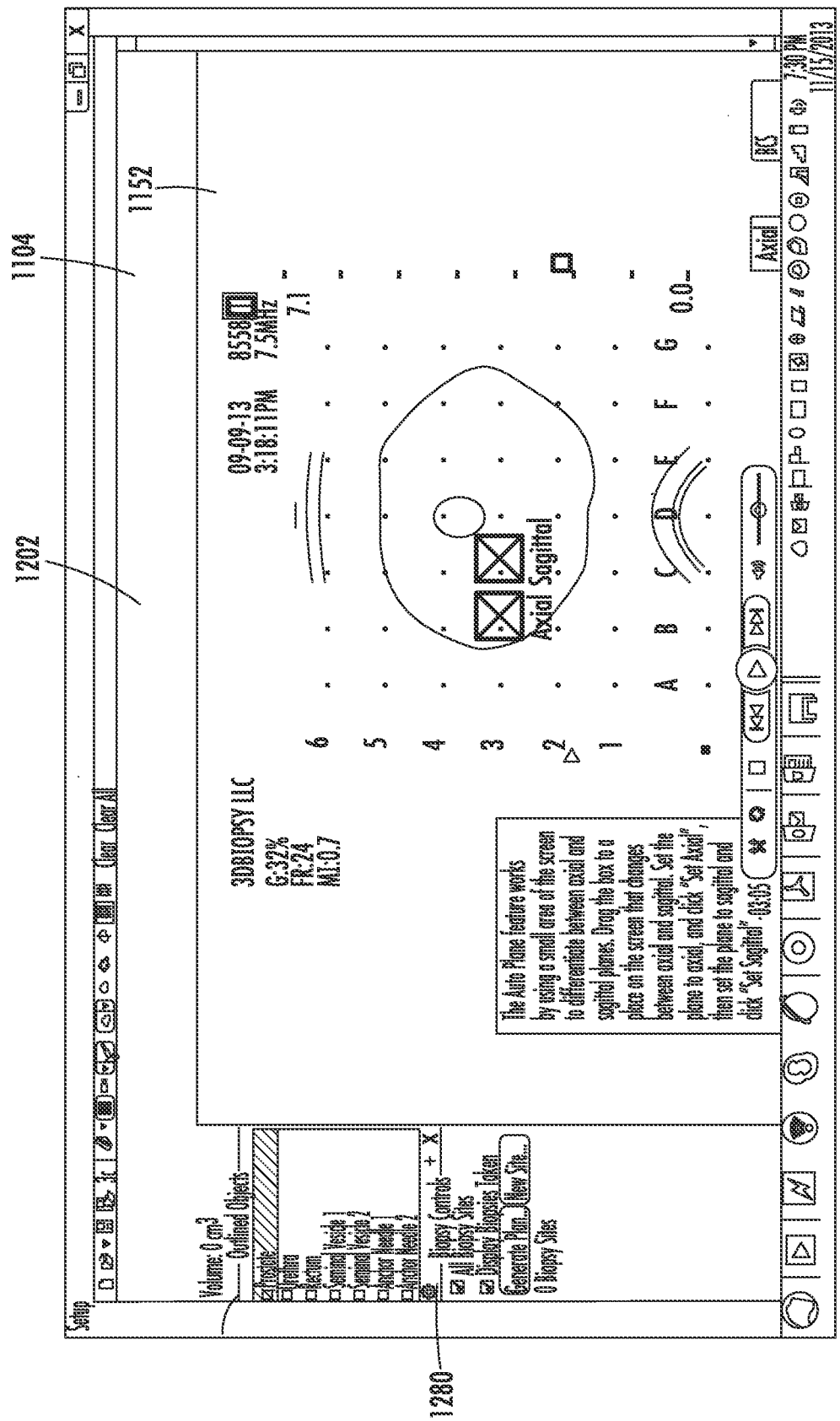

Referring to FIGS. 36-38, a transverse ultrasound image 1040 of the target tissue is generated in the image frame 1152. The image 1040 is an axial image or a transverse cross section of a prostate gland 1008 generated by real-time image data 1118 received from the ultrasound system 1034, namely data generated by a TRUS probe 1036 positioned within the rectum 1004 of a patient 1002.

The system 1102 displays an ultrasound grid 1332 of dots over the image 1040. The ultrasound grid 1332 is generated by the ultrasound system 1034 and consists of a coordinate system 1334 of horizontal rows of spaced dots along an x-axis 1336 and a vertical row of spaced dots along a y-axis 1338 representing the same number, arrangement, and spacing of the apertures 1020 of the template 1018. Thus the apertures 1020 of the template 1018 are represented by the dots of the ultrasound grid 1332. The ultrasound probe 1036 is represented by an arch of a circle at the bottom of the image 1040, and is centered on a horizontal row of spaced index markers 1342 below the bottom row of dots of the x-axis 1336. The index markers 1342 provide a fixed reference point for aligning a software grid 1344, representing a biopsy site plan, generated by the system 1102. In some embodiments, the elements of the ultrasound image 1040 are represented by gradations of white on a black background, and ultrasound grid is represented by white dots.

The software grid 1344 of circles consists of a coordinate system 1345 of horizontal rows of spaced circles along an x-axis 1346 and a vertical row of spaced circles along a y-axis 1348. The software gird 1344, when aligned with the ultrasound gird 1332, allows for coordination between the ultrasound system 1034 and the system 1102. When the coordinate systems 1334 and 1345 are aligned the system 1002 is able to accurately capture the image 1040 and any contours, and accurately represent the features of the three-dimensional prostate image 1472. In some embodiments, the elements of the software grid 1344 are represented by circles, and the color of the circles is determined by the user by changing the display preferences.

Referring to FIG. 37, the scale and location of the software grid 1344 is aligned with the scale and location of the ultrasound grid 1332 so that the top and bottom horizontal rows of dots of the ultrasound grid 1332 x-axis 1336 fall within the center of the corresponding top and bottom horizontal rows of circles of the software gird 1344 x-axis 1346, and the left and right vertical rows of dots of the ultrasound grid 1332 y-axis 1338 fall within the center of the corresponding left and right vertical rows of circles of the software grid 1344 y-axis 1348. The software grid 1344 is repositioned by selecting a corner handle 1352 or side handle 1354, represented by squares, by a cursor controlled by an input device, such as a mouse or stylus, and dragging the coordinate system 1345 across the image 1040. The software gird 1344 is resized by selecting a corner handle 1352 or side handle 1354 and squeezing or expanding the coordinate system 1345 across the image 1040. The sweep angle of the ultrasound probe 1036 and contour of the probe height 1358 are aligned by selecting the boxes at the end of the probe angle 1360 lines and pulling the probe angle 1360 lines to match the sweep angel of the ultrasound probe 1036, and by adjusting the height of the probe view to match the ultrasound image 1040. In some embodiments, the probe angle 1360 and probe height 1358 are represented by green lines. The center of the ultrasound probe 1036, and the center of the image 1040 generated by the ultrasound probe 1036 is represented by a probe centerline 1362.

Figure 39:
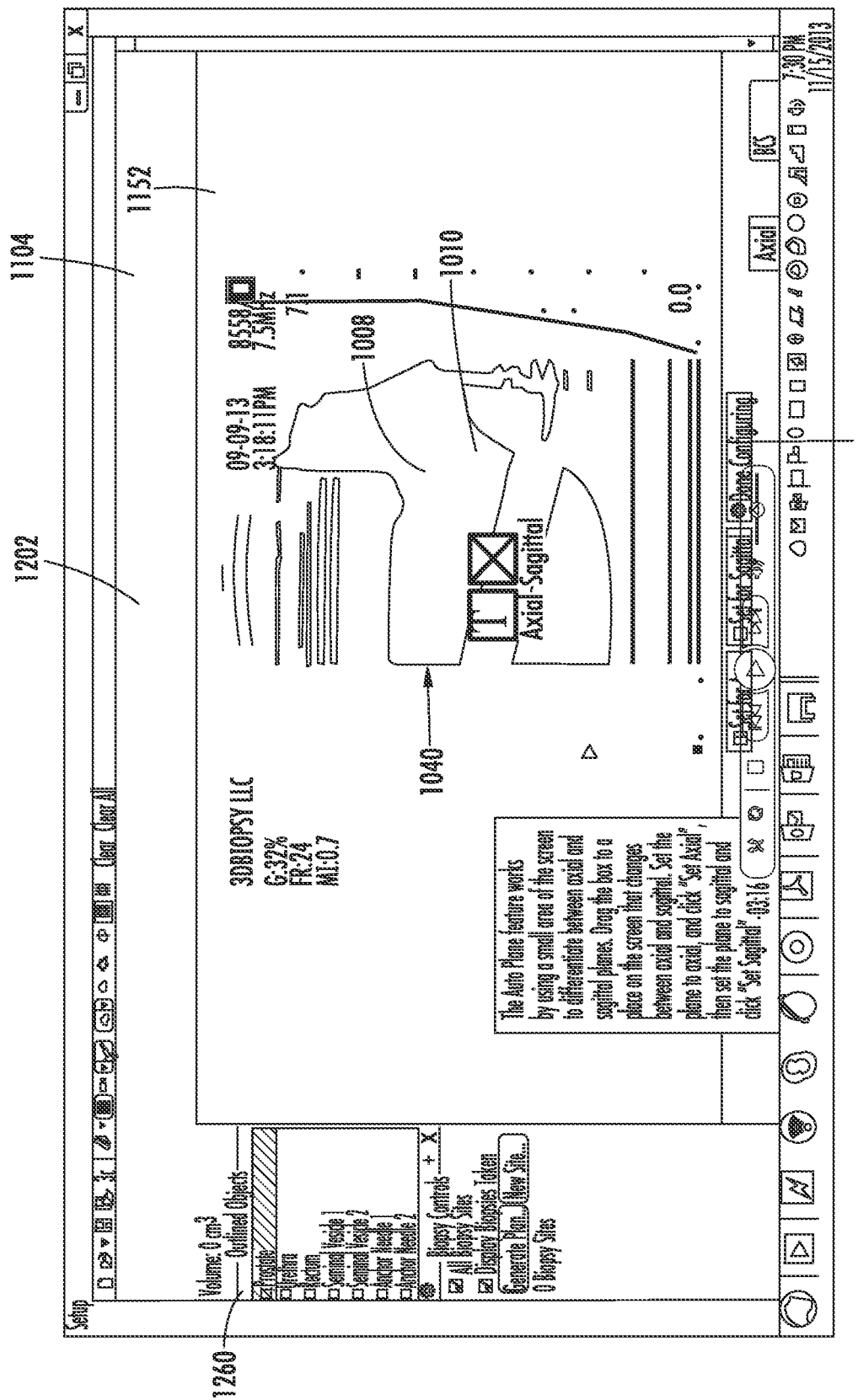

The image 1040 of the target tissue in the image frame 1152 automatically switches between a transverse image and a sagittal or axial image when the data from the ultrasound system 1034 is switched between a transverse image and a sagittal or axial image. This functionality is initialized by selecting the configure auto-plane 1364 tab. Referring to FIG. 38, a flashing rectangular box appears in the image frame 1152, and it is selected by the cursor and moved over the letter "T," representing the transverse view. In FIG. 38, the "T" is in the upper right hand corner of the image frame 1152, and is displayed as "8558/T." Next the view of the target tissue in the image frame 1152 switched from a transverse image to a sagittal image. Next another flashing rectangular box appears in the image frame 1152, and it is selected by the cursor and moved over the letter "S," representing the sagittal view. In FIG. 39, the "S" is in the upper right hand corner of the image frame 1152, and is displayed as "8558/S." Next the user selects the done configuring 1134 button.

Figure 40:
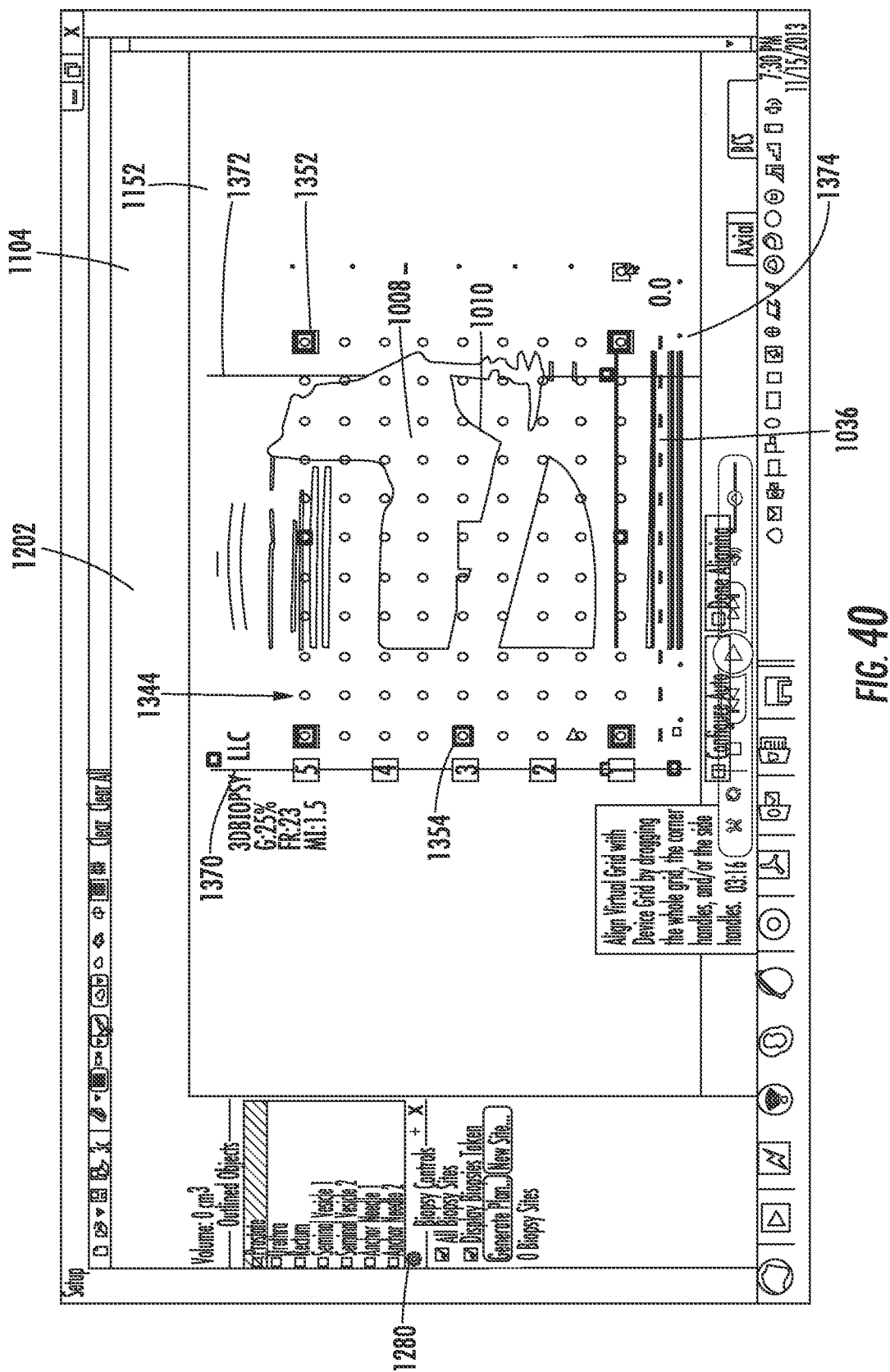

Referring to FIG. 40, a sagittal image or a longitudinal cross section of the prostate gland 1008 from the base 1012 to apex 1010 is shown in the image frame 1152. As above, the software grid 1344 is displayed over the ultrasound image 1040 of the prostate 1008, and the scale and location of the software grid 1344 needs to be adjusted. The software grid 1344 is repositioned by selecting a corner handle 1352 or side handle 1354, represented by squares, by a cursor controlled by an input device, such as a mouse or stylus, and dragging the coordinate system 1345 across the image 1040 The software gird 1344 is resized by selecting a corner handle 1352 or side handle 1354 and squeezing or expanding the coordinate system 1345 across the image 1040. The software grid 1344 is further positioned by aligning the probe height 1374 with the image of the ultrasound probe 1036 in the image 1040. In some embodiments, the probe height 1374 is represented by a green lines. The scale of the software grid 1344 in the sagittal view is also determined by the location of the base 1012 and apex 1010 of the prostate 1008. In this view, a vertical base alignment 1370 line is projected adjacent the left edge of the software grid 1344 and a vertical apex alignment 1372 line is projected adjacent the right edge of the software gird 1344. The base alignment 1370 line is moved to align with the base 1012 of the prostate 1008 and the apex alignment 1372 is moved to align with the apex 1010 of the prostate 1008.

When grids 1332 and 1344 are aligned, and probe height 1358 and probe angle 1360 are set in the transverse view, and grid 1344, probe height 1374, and base and apex alignment 1370, 1372 are set, the virtual grid image adjustments are complete for setting up the system 1102 for use with the imaging system 1032 for the particular patient 1002. The above settings are stored by the system 1102 and the above steps do not need to be repeated for subsequent patients if the system 1102 is used with the same imaging system 1032.

Contouring

Figure 41:
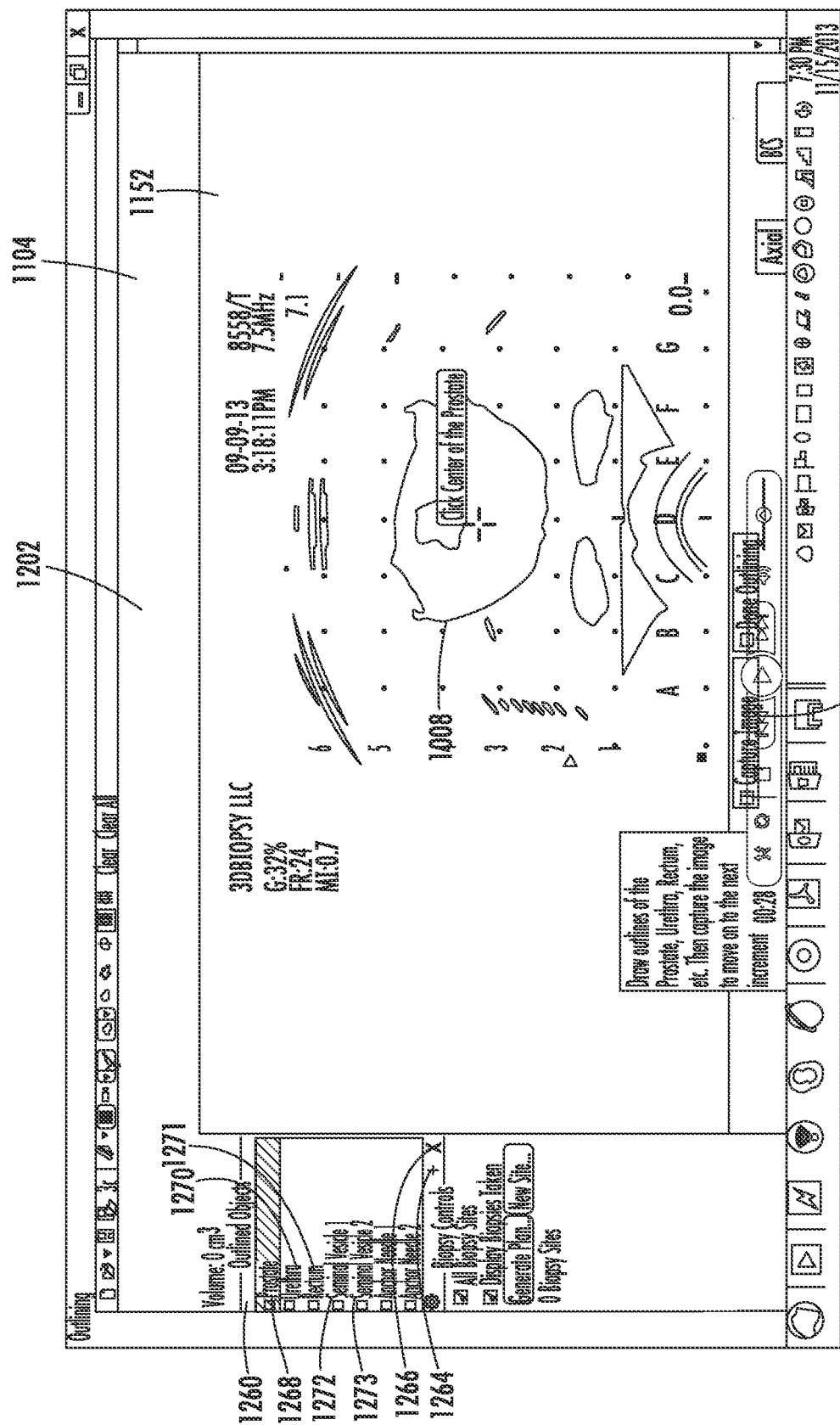
FIGS. 41-49 are illustrations of a graphical user interface according to some embodiments of the disclosed subject matter for contouring structures of the tissue site and ultra sound hardware.

After the system 1102 is aligned, identification and line contouring of the structures of the target tissue and surrounding structures are performed. The system 1102 is used to construct a three-dimensional model of the target tissue using a plurality of line contours of tissue structural elements appearing in each transverse ultrasound image 1040 of the target tissue. Referring to FIG. 41, elements, such as structures and organs, are named and given a line color using the outline object frame 1260. Selecting the add object 1264 button allows a user to input an element name and select a line color. Selecting the delete object 1266 button removes an element. In an embodiment, the structures of the prostate are identified, including the prostate 1268 as a red line, the urethra 1270 as a green line, the rectum 1271 as a blue line, a first seminal vesicle 1272 as an orange line, a second seminal vesicle 1273 and an orange line, a first anchor needle 1274 as a yellow line, and a second anchor needle 1276 as a yellow line. The above text and line colors can be adjusted by selecting an element and selecting the settings 1262 button. Any number of elements can be included and any number of colors assigned.

Figure 42:
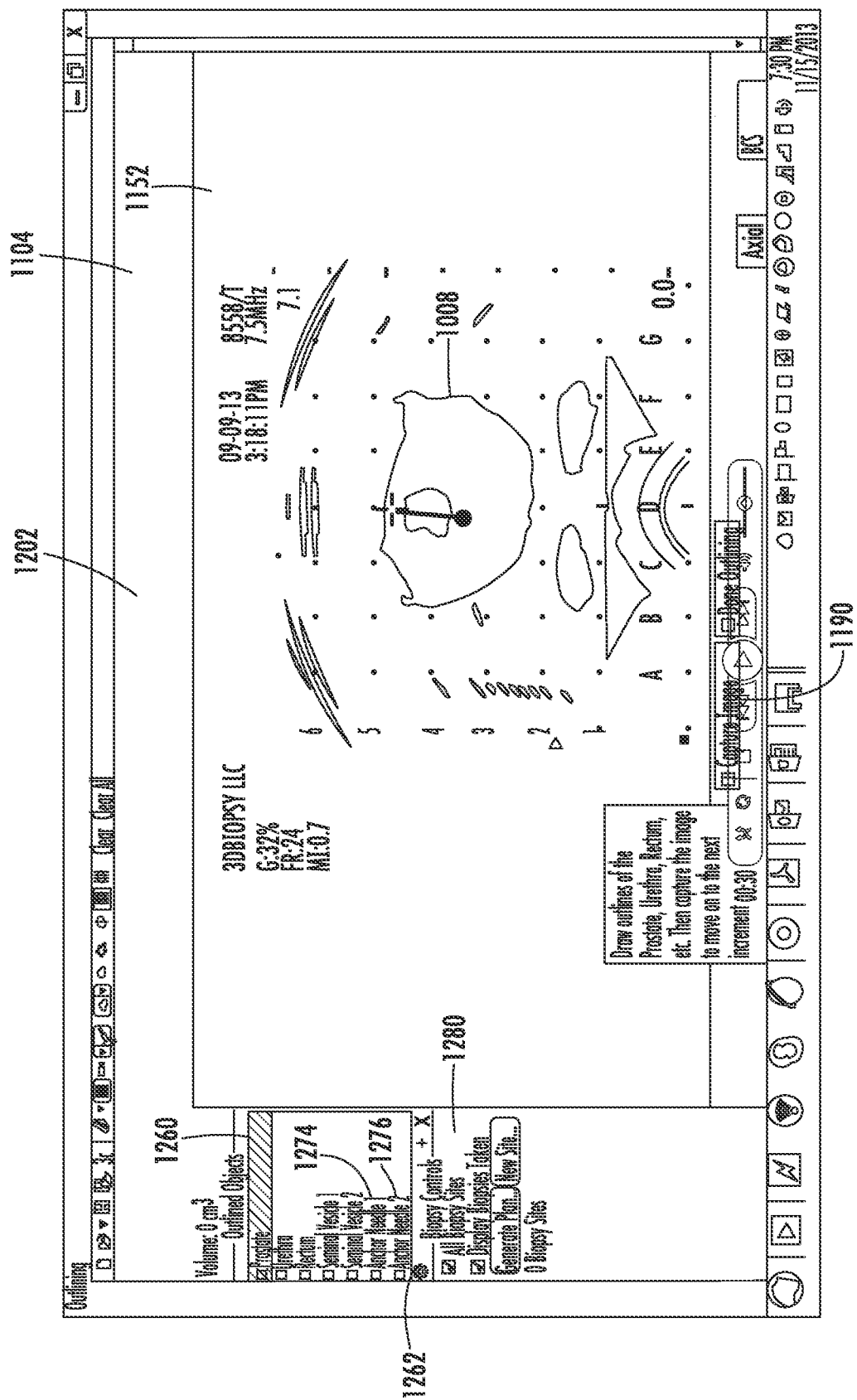
Figure 43:
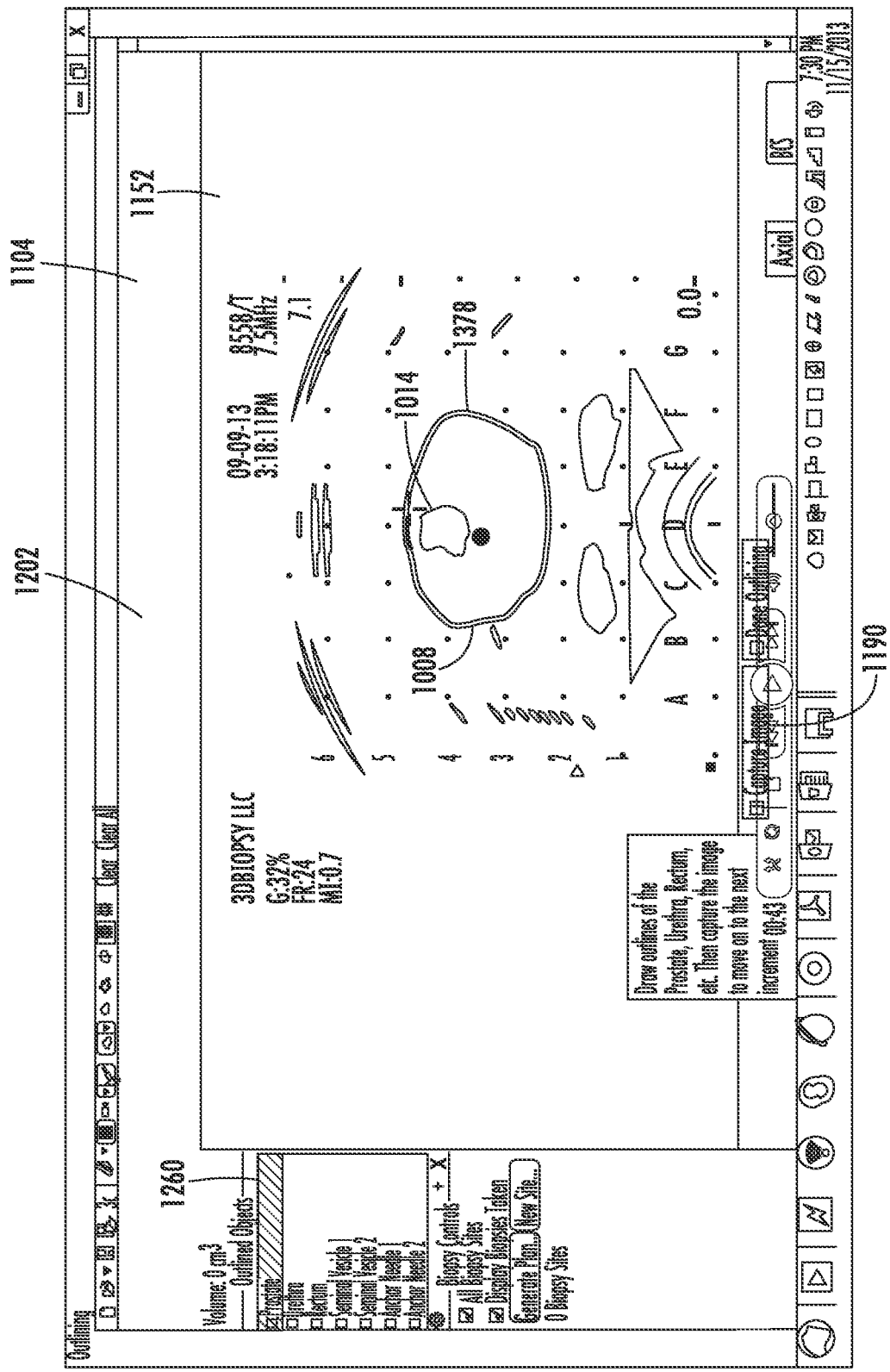

Various contour tools may be used to create a contour line of an element represented by the image 1040. The tool bar 1166 includes an outline tool 1184 button for initiating a contour line, a sweep contour 1188 button for creating a continuous contour line with the cursor, and a node contour 1190 button for creating a contour with the cursor moving to individual nodes at the edge of the element. To begin constructing a first contour image, the ultrasound probe 1036 is advanced inward until it is at a first position adjacent the base 1012 of the prostate 1008 whereby a first transverse image 1040 is displayed in the image frame 1152. In some embodiments, the first element selected for contouring from the list in the outline object frame 1260 is the prostate 1268. Upon selecting the prostate 1268 outline object the system 1102 prompts the user to identify a first point on the first transverse image 1040 as the center of the prostate by selecting the location on the image frame 1152 with the cursor (FIG. 41). A dot is then displayed on the first transverse image 1040 at the first point and the user drags a line from the first point to a second point at an outer edge of the prostate 1008 shown on the image 1040 to initiate outlining the element (FIG. 42). The user then traces the edge of the prostate 1008 shown on the image 1040, stopping at the second point, creating a prostate contour line 1378 (FIG. 43). The edge of the contour can be adjusted by selecting the node contour 1190 button and selecting a point on the contour line 1378 and moving the cursor. The image 1040 and the overlaid contour can be enlarged to aid fine tuning of the contour line 1378 by moving the cursor along the zoom 1320 bar within the image control pane 1312. The entire contour can be deleted by selecting the clear 1198 button and the contour begun again.

In some embodiments, the second element selected for contouring is the urethra 1014. Upon selecting the urethra 1270 from the outline object frame 1260 the user then traces the inner edge of the urethra 1014 shown on the first transverse image 1040 creating a urethra contour line 1380. In some embodiments, the contour of the urethra 1014 can be selected as a circle and sized and positioned accordingly. In some embodiments, the third element selected for contouring is the rectum 1004. Upon selecting the rectum 1271 from the outline object frame 1260 the user then traces the portion of the rectum 1004 shown on the first transverse image 1040 creating a rectum contour line 1382.

Figure 44:
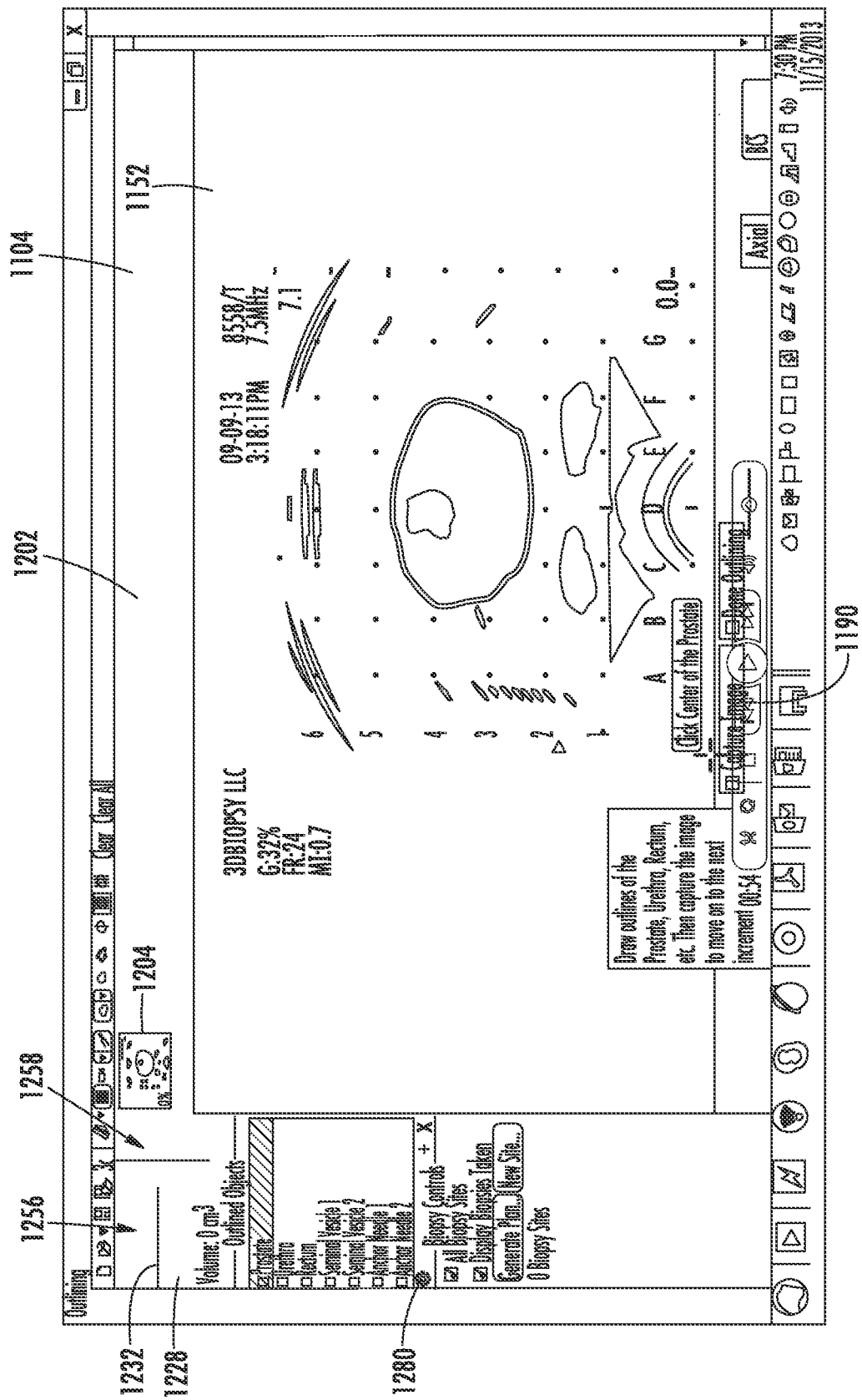
Figure 45:
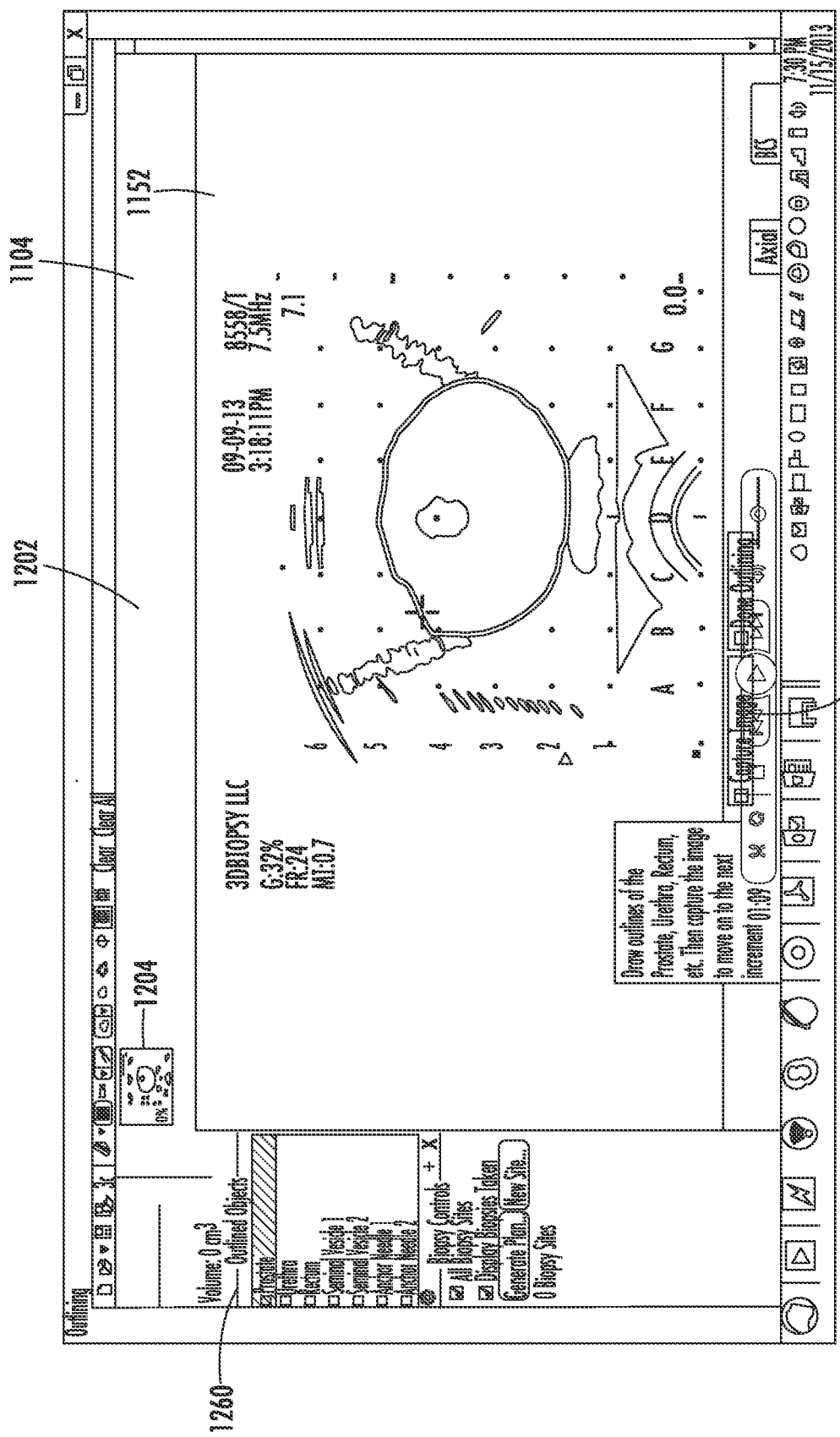

The contour lines of the elements of the first transverse image are saved as a first captured image 1204 by the system 1102 by selecting the capture image 1190 button in the lower left portion of the image frame 1152. The first captured image 1204 appears at the left in the thumbnail frame 1202 and is referenced by the number 0 (FIG. 44). The first captured image 1204 is also shown as a first slice 1232 of a three-dimensional image 1472 in the preview pane 1228. The three-dimensional image 1472 is shown as two images, a plan image 1256 of the prostate 1008 with the base 1012 shown at the top, and a side elevation image 1258 of the prostate 1008 with the base 1012 shown at the left. The edges of the contour may be adjusted as described above (FIG. 45).

Figure 46:
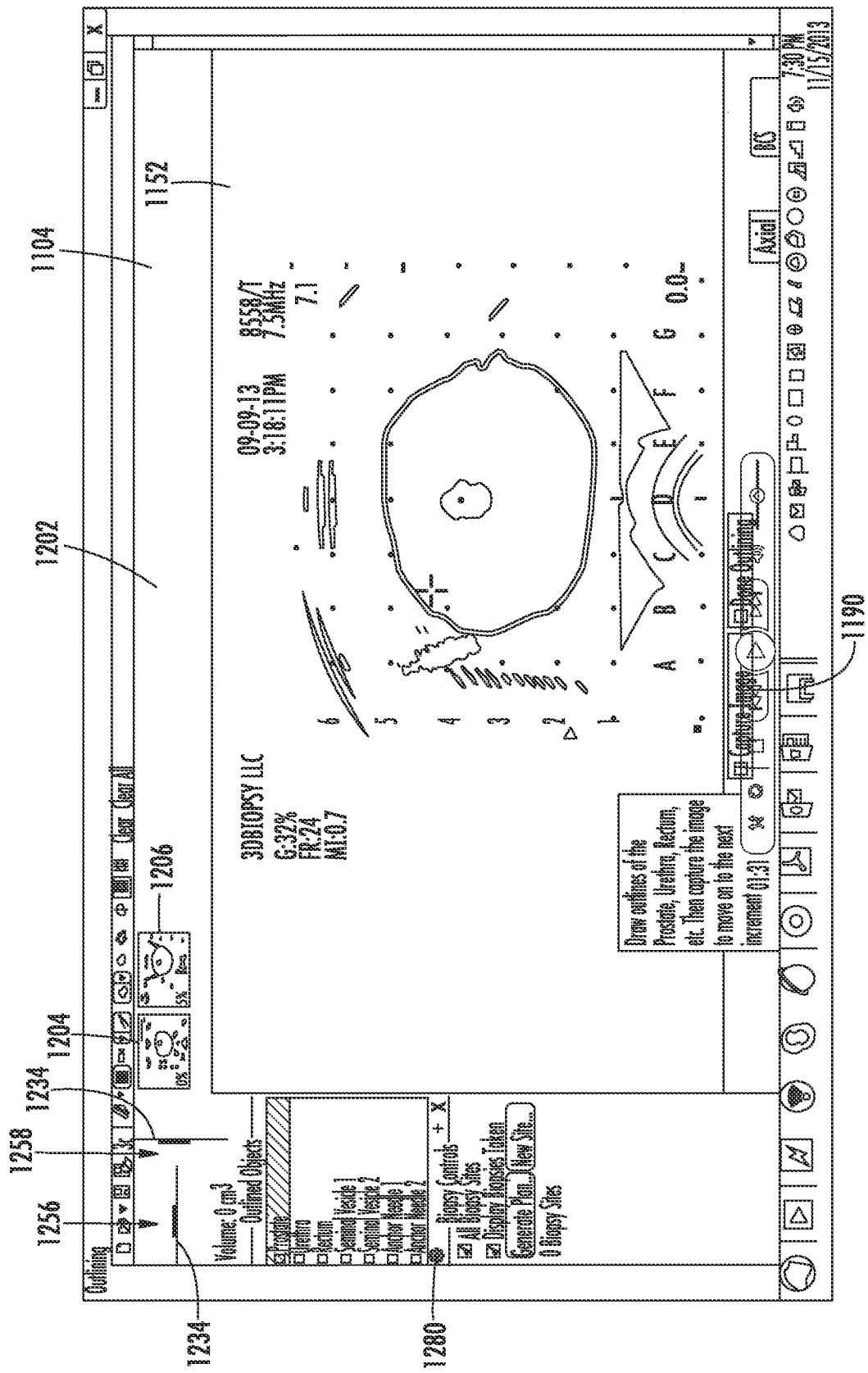
Figure 47:
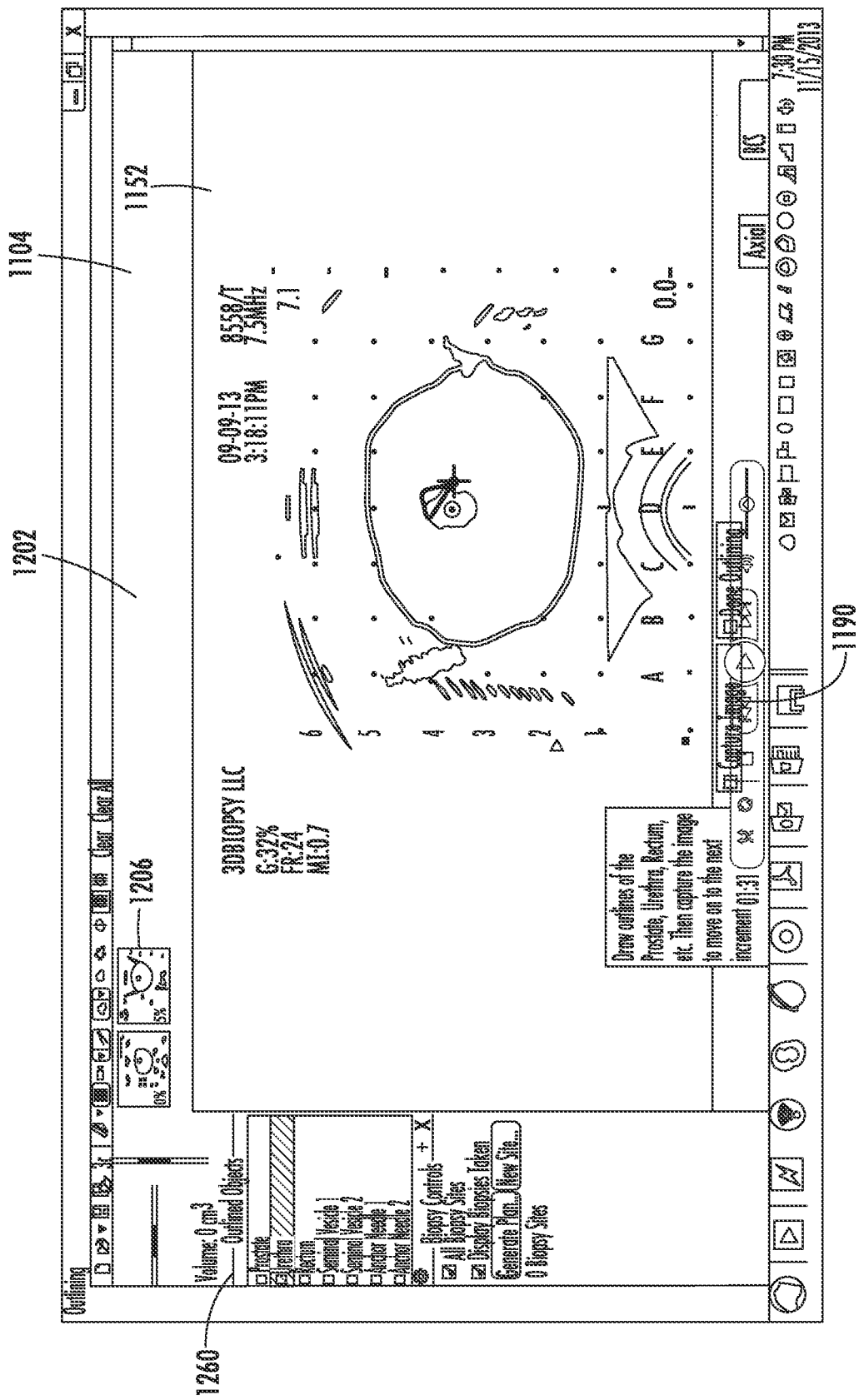

The ultrasound probe 1036 is then moved out of the rectum 1004 one unit distance toward the apex of the prostate to show a second transverse image 1040 is displayed in the image frame 1152 (FIG. 46). The unit distance is determined by the index mechanism 1028. In some embodiments, one unit distances is about 5 mm. In some embodiments, the index mechanism 1028 is mechanically actuated and the system 1102 moves the probe 1036 after capturing of each contour. The unit distance separating each transverse image 1040 may be programmed into the system 1102. The elements of the second transverse image 1040 are contoured and modified as above (FIG. 47), and the contours of the elements of the second transverse image 1040 are saved as a second captured image 1206 by the system 1102 by selecting the capture image 1190 button. The second captured image 1206 appears to the right of the first captured image 1204 in the thumbnail frame 1202 and is referenced by the number 5 representing the distance the second captured image 1206 is spaced from the first captured image 1204. The second captured image 1206 is shown as a second slice 1234 of the three-dimensional image 1472 in the preview pane 1228. The second slice 1234 is positioned below the first slice 1232 in the plan image 1256, and to the right of the first slice 1232 in the elevation image 1258.

Figure 48:
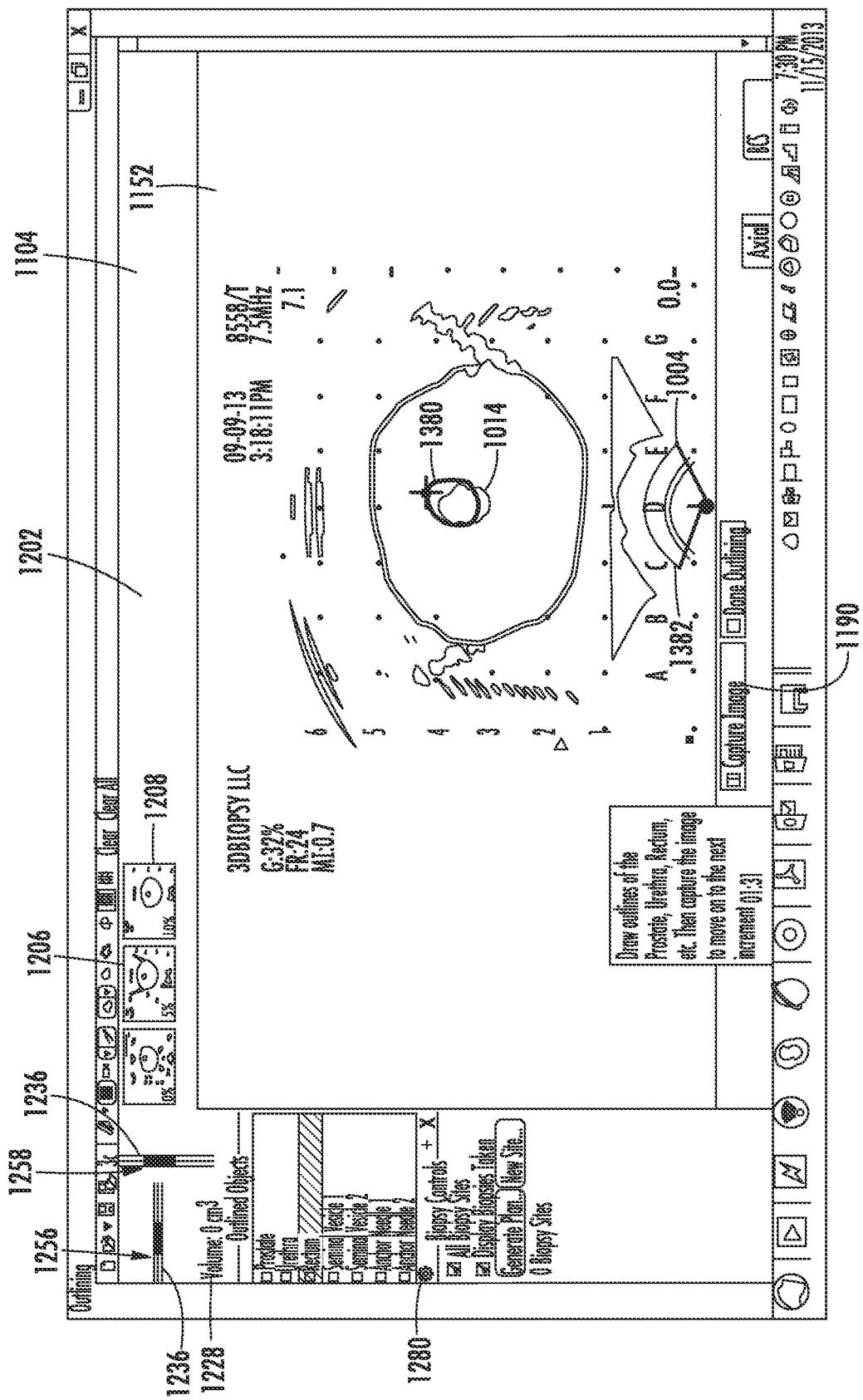

The ultrasound probe 1036 is then advanced one unit distance out of the rectum 1004, as described above, to show a third transverse image 1040 in the image fame 1152 (FIG. 48). The elements of the third transverse image 1040 are contoured and modified as above, and the contours of the elements of the third transverse image 1040 are saved as a third captured image 1208 by the system 1102 by selecting the capture image 1190 button. The third captured image 1208 appears to the right of the second captured image 1206 in the thumbnail frame 1202 and is referenced by the number 10 representing the distance the third captured image 1208 is spaced from the first captured image 1204. The third captured image 1208 is shown as a third slice 1236 of the three-dimensional image 1472 in the preview pane 1228. The third slice 1236 is positioned below the second slice 1234 in the plan image 1256, and to the right of the second slice 1234 in the elevation image 1258.

Figure 49:
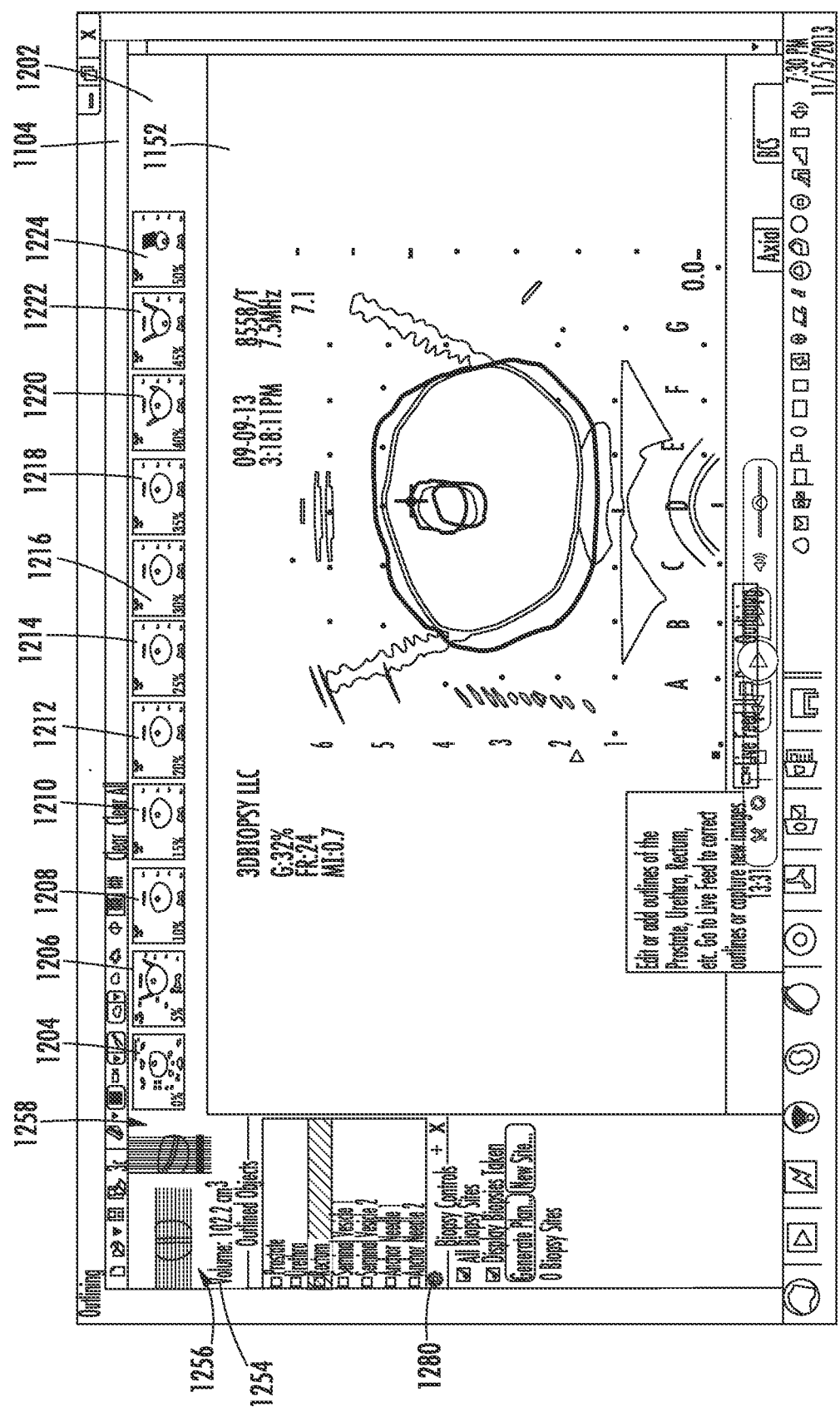

Additional captured images are generated and saved to the system 1102 as described above by advancing the ultrasound probe 1036 one unit, contouring elements on the transverse image 1040, and creating captured images of the contours of the image elements. Accordingly, a fourth, fifth, sixth, seventh, eighth, ninth, tenth, and eleventh contoured image 1210, 1212, 1214, 1216, 1218, 1220, 1222, and 1224 are created and used to create a fourth, fifth, sixth, seventh, eighth, ninth, tenth, and eleventh slice, respectively, with the eleventh contoured image 1224 at an eleventh position at the apex 1010 of the prostate 1008 (FIG. 49). The aforementioned contoured images are arranged in order adjacent to each other in the thumbnail frame 1202, plan image 1256, and elevation image 1258 as described above.

In some embodiments, capturing two or more images completes capture of a sufficient number of images and slices to render the three-dimensional plan image 1256 and three-dimensional elevation image 1258. In some embodiments, the margin of the tissue structures are filled in between each slice by automatically interpolating the proper contour.

Selection of any image in the thumbnail frame 1202 outlines the image in a box, highlights the corresponding slice in the plan image 1256 and elevation image 1258, and displays the captured image in the image frame 1152 allowing a user to check the contours and make any modifications to the contours desired. When the user is done capturing images and editing the contours of the captured images the contouring is completed by selecting the done contouring 1384 button at the bottom of the image frame 1152. The system 1102 calculates the target tissue volume 1254, here the volume of the prostate 1008, and displays the value below the images 1256, 1258. In some embodiments, the volume value is represented in a metric volume, including cubic centimeters.

Three-Dimensional Model

Figure 50:
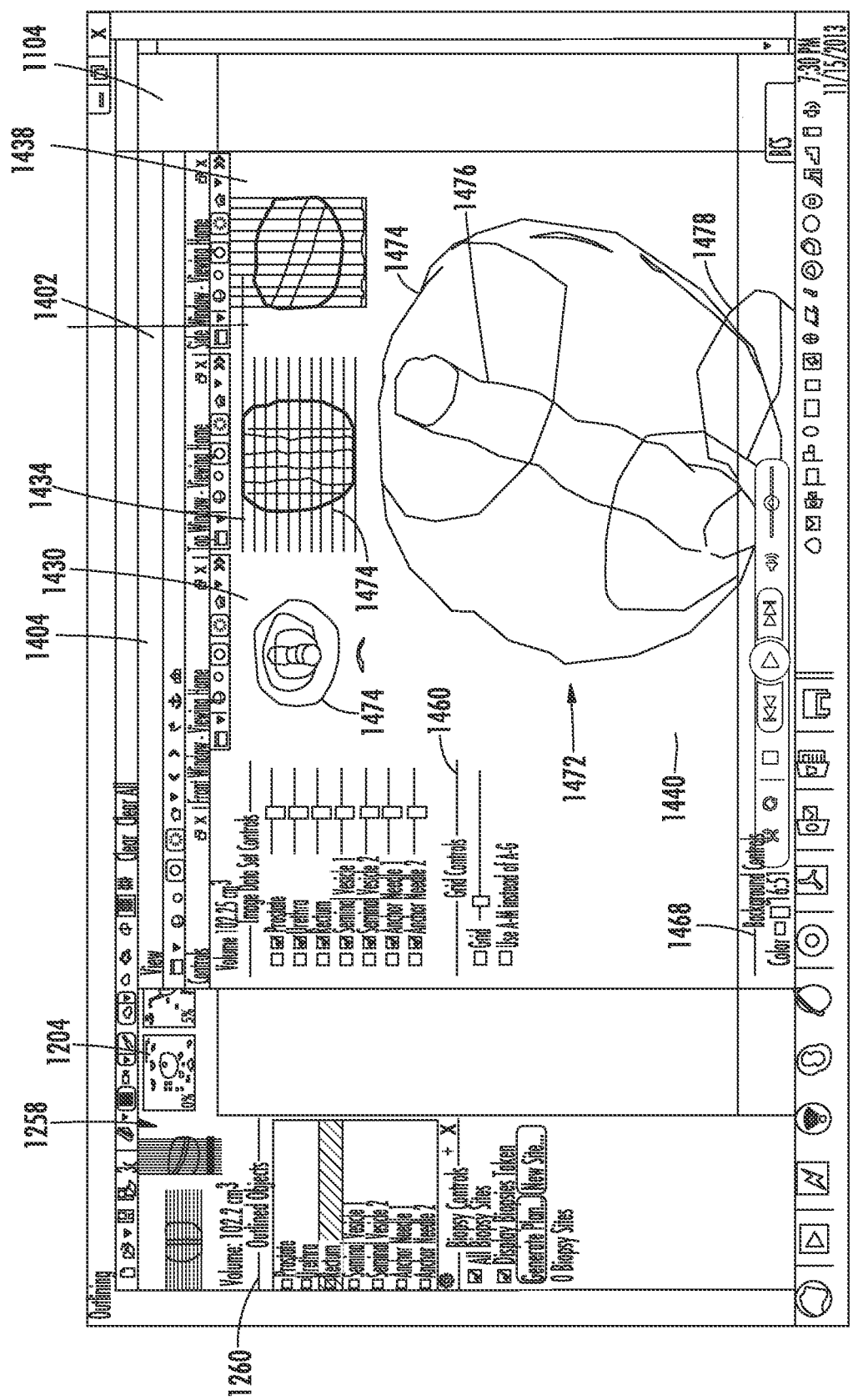
FIGS. 50-52 are illustrations of a graphical user interface according to some embodiments of the disclosed subject matter for viewing the three-dimensional images created from the contour images generated during contouring.
Figure 51:
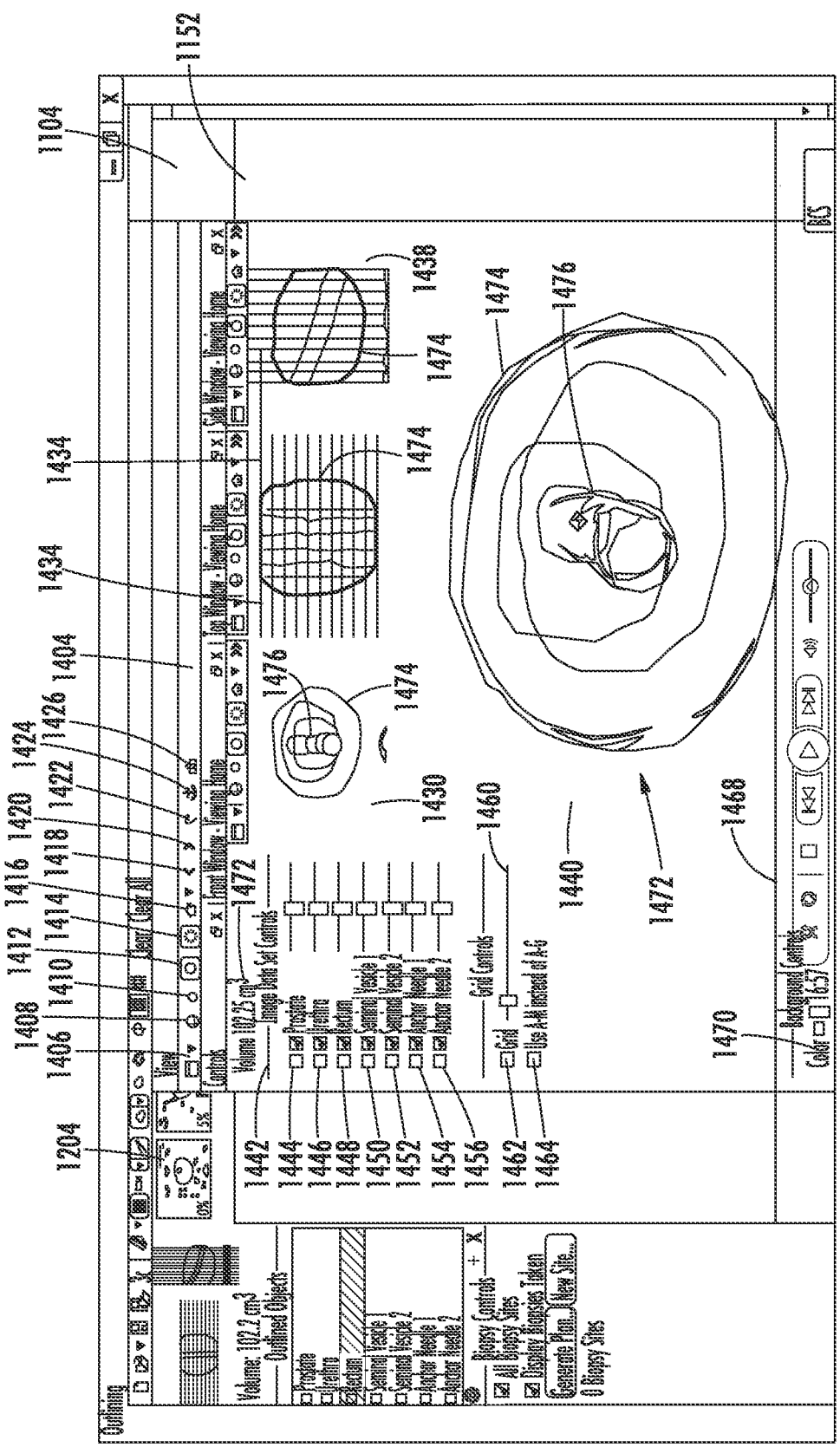
Figure 52:
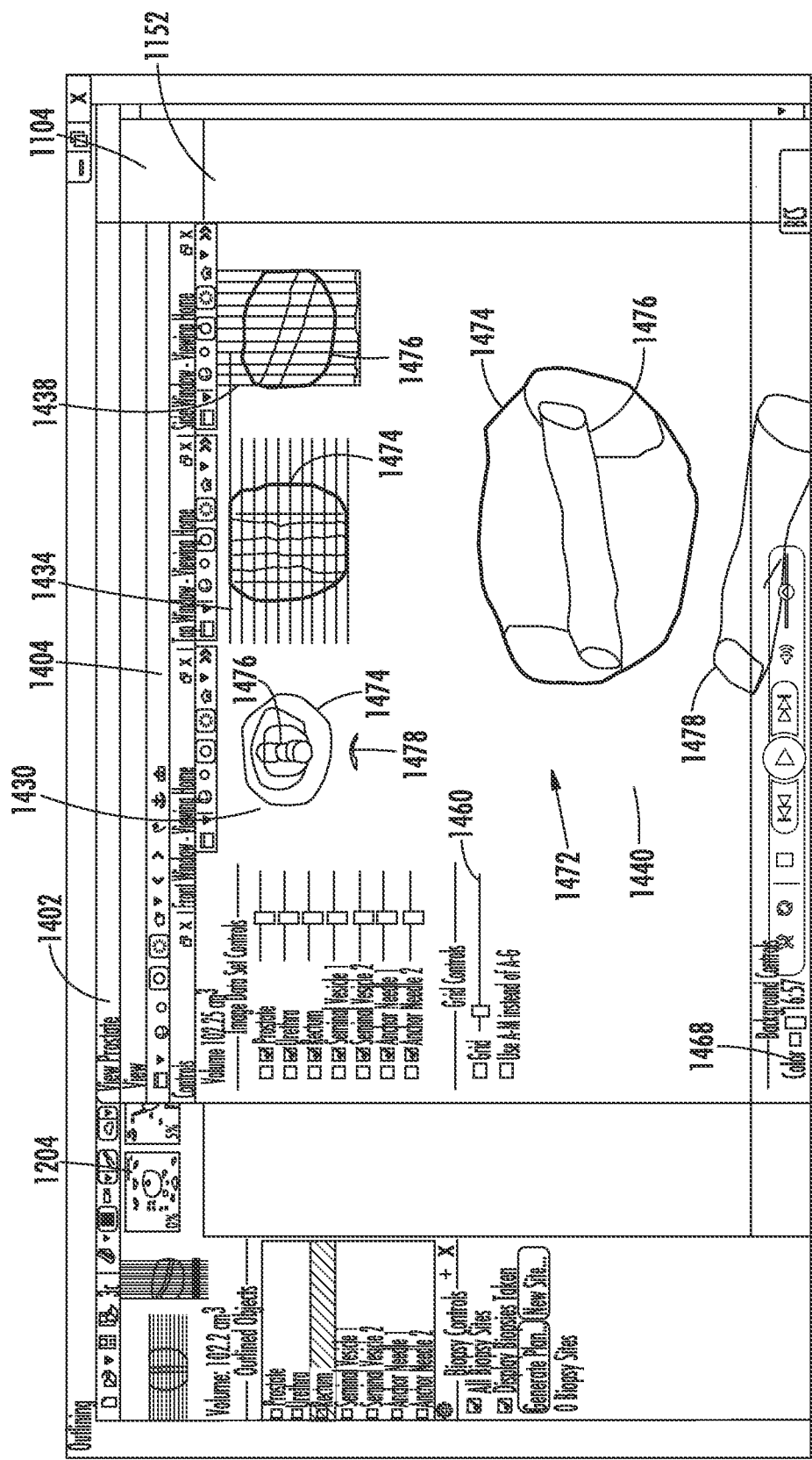

The tool bar 1166 includes a three-dimensional reconstruction 1174 button that presents the three-dimensional image of the target tissue generated from the contour images in a three-dimensional image graphical user interface (3DGUI) 1402. Referring to FIGS. 50-52, three-dimensional images of the prostate are rendered in the 3DGUI 1402 frame from the plurality of contour images generated above, including an isometric, three-dimensional image of the prostate 1472 rendered in an image frame 1440. The image frame 1440 is: bound at the top by a tool bar 1404, and a front view window 1430, a top view window 1434, and an elevation view window 1438; and bound at the side by an image control frame 1442, and a grid control frame 1460, and a background control frame 1468.

The image frame 1440 displays an interactive three-dimensional image of the prostate 1472 and related structures. The image of the prostate 1472 includes lines and shading. The intensity of the lines and shading can be manipulated by increasing or decreasing the tones of the colors associated with the contour elements. The prostate model and related structures can be studied by the viewer, and the model may be rotated in any direction by selecting a point on the image and moving the cursor/pointing device.

The tool bar 1404 includes tool buttons that add windows showing three-dimensional images of a virtual prostate from different vantage points, constructed of the outer contour of the tissue structures as a wire frame. The file drop down 1406 button offers a section of three views, a front view, a top view, and a side view. The wire frame 1408 button converts the three-dimensional prostate image 4172 into a wire frame contour image. The shading 1410 button and the shading button 1412 control the color intensity of the image. The shading controls 1414 button controls the contrast of the three-dimensional prostate image 1472. The home drop down 1416 button sets the images in one of the front view window 1430, top view window 1434, and elevation view window 1438. The back 1418 button returns to the previous image. The forward 1420 button moves to the next image. The rotate 1422 button switches the image perspective. The anchor 1424 button sets anchor points on the image. The camera 1426 button captures the scene and save it to the file.

The front view window 1430 includes the same buttons as found on the tool bar 1404 and displays an image of the front of the prostate 1472. The top view window 1434 includes the same buttons as found on the tool bar 1404 and displays an image of the top of the prostate 1472. The elevation view window 1438 includes the same buttons as found on the tool bar 1404 and displays an image of the side of the prostate 1472. Selection of any image in the thumbnail frame 1202 is shown as a highlighted slice in the top view window 1434 and elevation view window 1438. The corresponding contour line or lines are highlighted on the prostate 1472 image.

The image control frame 1442 allows the intensity of the color of the various tissues and elements created in the object frame 1260 displayed in the windows to be adjusted. In this embodiment, the structure of the prostate 1444 is represented in red, the urethra 1446 is represented in green, the rectum 1448 is represented in blue, the first seminal vesicle 1450 is represented in orange, the second seminal vesicle 1452 is represented in orange, the first anchor needle 1454 is represented in yellow, and the second anchor needle 1456 is represented in yellow. Slider controls adjacent the labels above may be moved from left to right to vary the intensity of the color. As above, the system 1102 calculates the volume of the prostate 1472, and displays the value above the image control frame 1442.

The grid control frame 1460 controls a three-dimension grid. A grid 1462 checkbox turns a grid overlying the prostate 1472, represented by a gridlines displayed as a three-dimensional graph, on or off. A slider control next to the grid 1462 checkbox may be moved from left to right to vary the intensity of the of the grid lines. A "Use A-M instead of A-G" 464 checkbox turns on a probe box displaying the ultrasound probe, and a slider control next to the checkbox may be moved from left to right to vary the intensity of the image of the ultrasound probe.

The background control frame 1468 allows the color 1470 of the image frame 1440 to be white, black, or any variation in between by moving the slider control adjacent the color 1470 label from left to right, respectively. The size of the prostate image 1472 in the image frame 1440 can be changed from small to large by moving the image size slider control from left to right respectively.

Referring to FIG. 51, the prostate 1472 is shown with the apex of the prostate in the foreground, and the base of the prostate in the background. The prostate is represented by a prostate margin 1474, shown in some embodiments as a red, translucent, hollow, spheroid, with an opening at each end. The urethra is represented by a urethra margin 1476, shown in some embodiments as a green, translucent, hollow, tube, with an opening at each end. The prostate margin 1474 reflects the outer margin of the prostate tissue. The urethra margin 1476 reflects both the interior margin of the prostate tissue and the outer margin of the urethra as it passes through the prostate tissue. Therefore, the volume of the prostate 1472 is calculated by the system 1102 by calculating the volume of the tissue between the prostate margin 1474 and the urethra margin 1476. Referring to FIG. 52, the prostate 1472 is shown with apex of the prostate at the left, the base of the prostate at the right, and the rectum represented by a rectum margin 1478, shown in some embodiments as a blue, translucent, hollow, tube with an opening at each end.

Three-Dimensional Image Alignment

Figure 53:
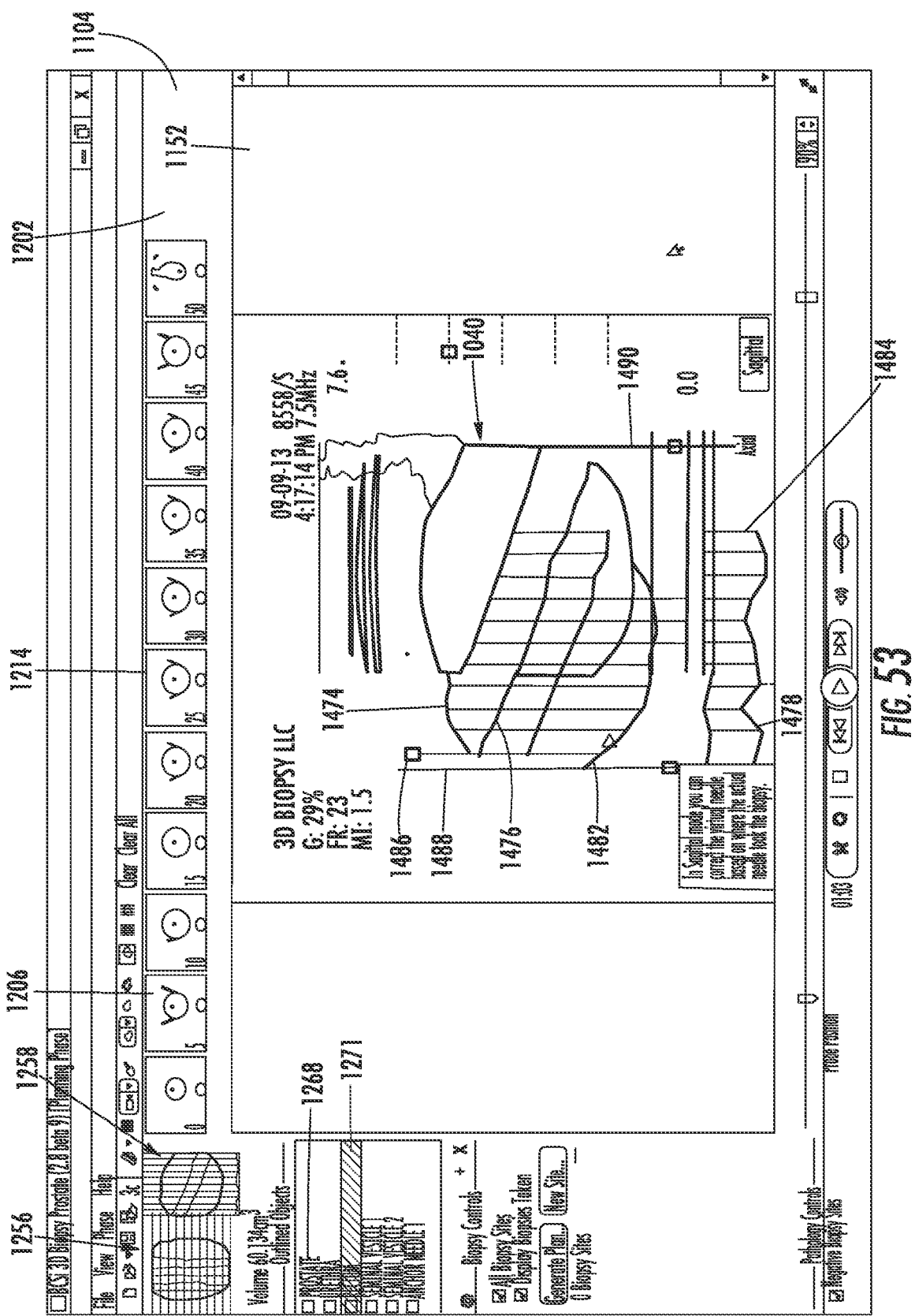
FIGS. 53-56 are illustrations of a graphical user interface according to some embodiments of the disclosed subject matter for aligning the three-dimensional image to the ultrasound image of the target tissue site.
Figure 54:
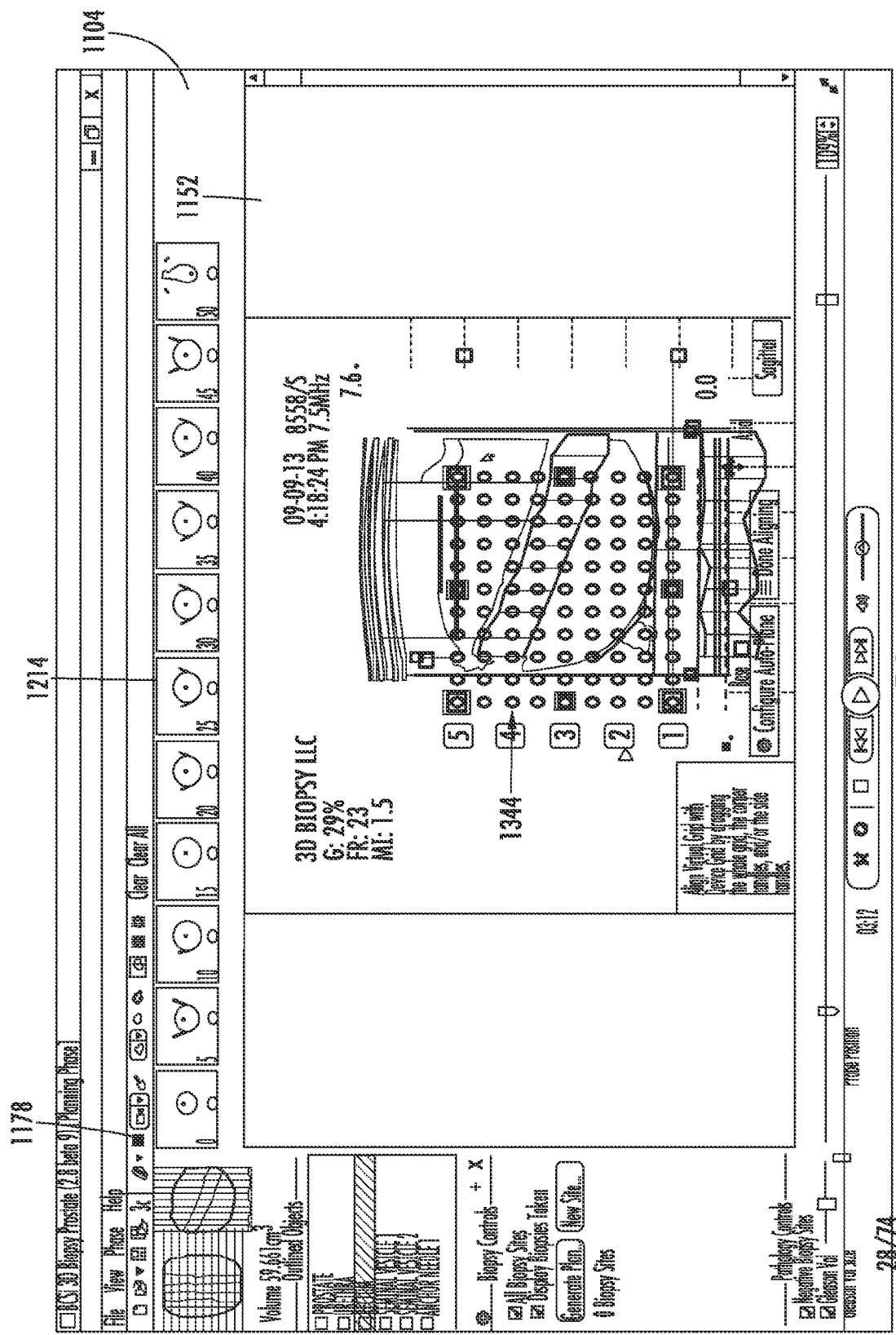
Figure 55:
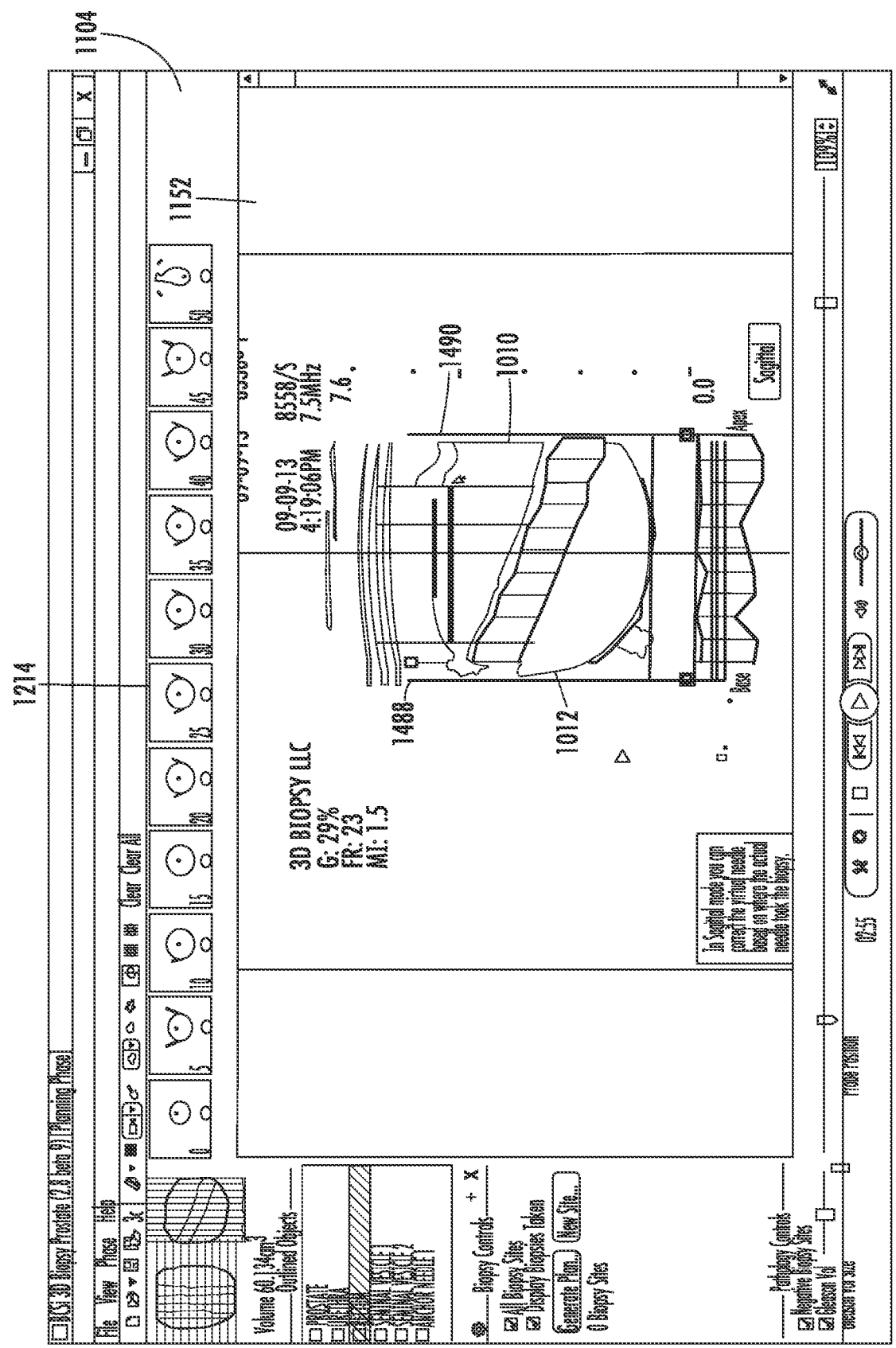

After the three-dimensional prostate image 1472 is generated, the alignment of the image 1472 may need to be realigned with the ultrasound image 1040 of the prostate 1008 before biopsy planning can begin. Referring to FIG. 53, the sagittal image 1040 or a longitudinal cross section of the prostate 1008 from the base 1012 to the apex 1010 is shown in the image frame 1152 with a sagittal image or longitudinal cross section image 1482 of the three-dimensional prostate image 1472 overlaying the image of the prostate 1008. The cross section image 1482 includes vertical lines representing the slices generated above. Referring to FIG. 54, selecting the grid 1178 button brings up the software grid 1344. The user then aligns the prostate margin 1474, urethra margin 1476, and rectum margin 1478 of the cross section image 1482 with the corresponding tissue structures of the image 1040 in the image frame 1152. The scale of the cross section 1482 may be adjusted along a horizontal axis 1484, and may be adjusted along a vertical axis 1486. The location of the base 1012 and apex 1010 of the prostate 1008 needs to be determined so the base alignment 1488 line and apex alignment 1490 line can be aligned to the base and apex of the prostate in the ultrasound image 1040. A vertical base alignment 1488 line is project adjacent the left edge of the cross section 1482 and a vertical apex alignment 1490 line is projected adjacent he right edge of the cross section 1482. Referring to FIG. 55, the base alignment 1488 line is moved to align it with the base 1012 of the prostate 1008 by selecting the grab box at the bottom of the line, and the apex alignment 1490 is moved to align with the apex 1010 of the prostate 1008 by selecting the grab box at the bottom of the line. Once the features of the cross section 1482 are aligned with the features in the image frame 1152.

Figure 56:
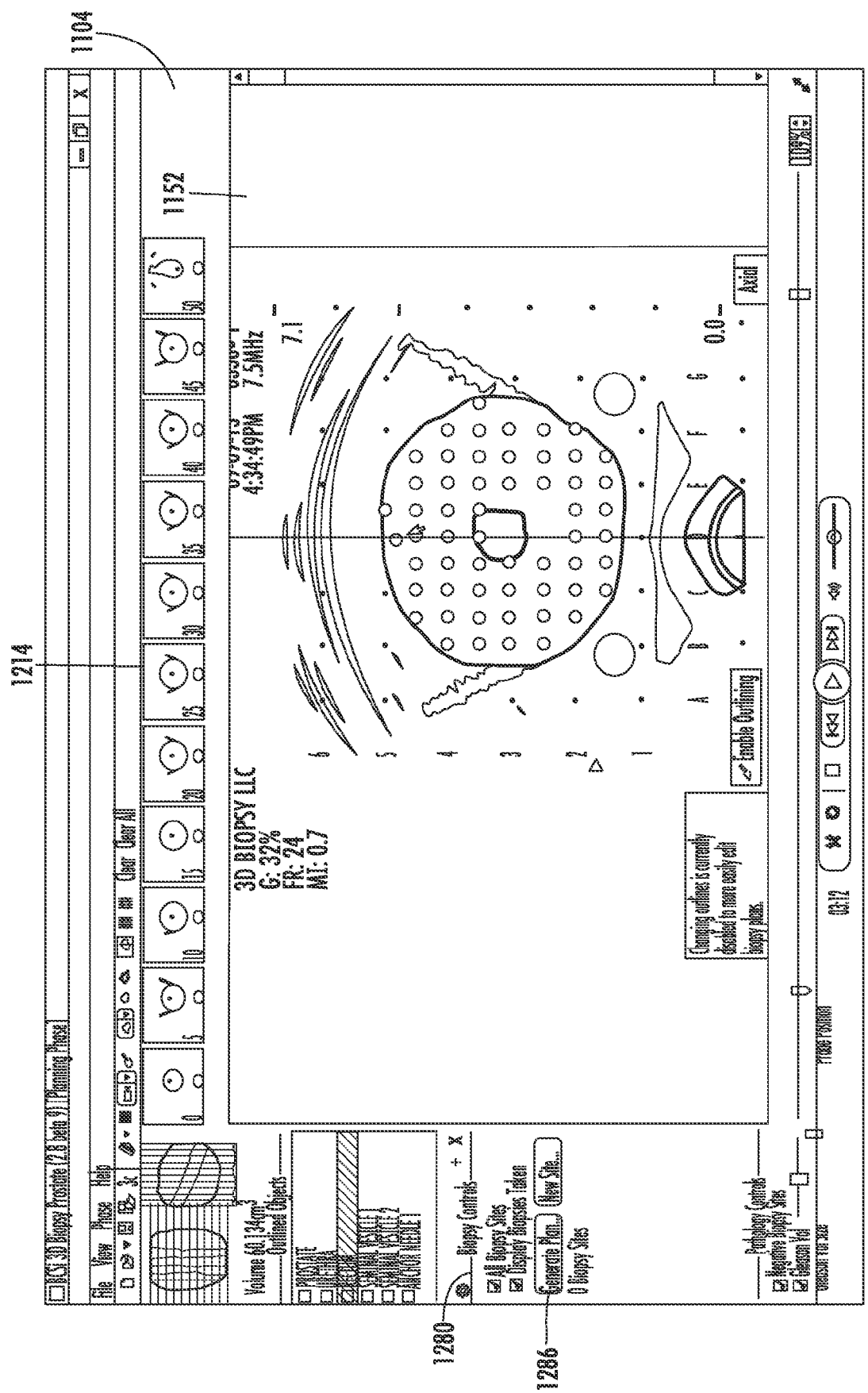
Figure 57:
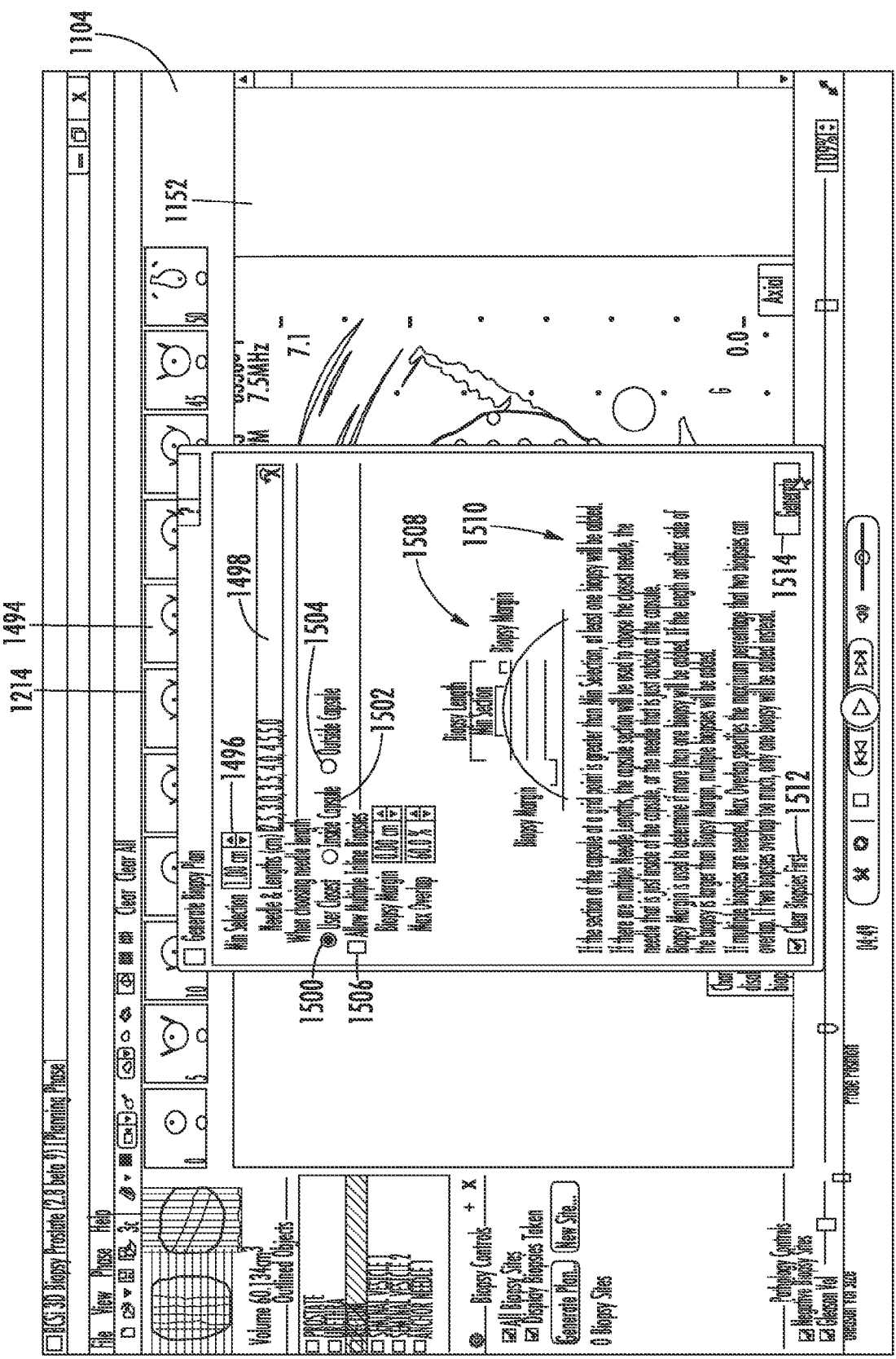
FIGS. 57-60 are illustrations of a graphical user interface according to some embodiments of the disclosed subject matter for planning a biopsy procedure of the target tissue site.

Referring to FIG. 56, the biopsy planning phase continues by generating a biopsy site plan. A biopsy site plan is generated using the biopsy control frame 1280 in the GUI 1104. Selecting the generate plan 1286 button brings up a biopsy plan graphical user interface (BPGUI) 1494 frame. Referring to FIG. 57, the BPGUI 1494 enables a user to specify the parameters of the biopsy plan. By way of example, the BPGUI 1494 shows a biopsy plan for the prostate 1008. The minimum section 1496 text box allows a user to specify the minimum length of the tissue specimen to be taken. In some embodiments the minimum length is 1.00 cm. The value displayed in the minimum section 1496 text box may be adjusted by 0.01 cm increments by selecting the up arrow adjacent the text box to increase the value, and the value may be decreased by selecting the down arrow adjacent the text box. In this example, the length of the minimum section determines how close to the prostate capsule or contoured perimeter of the gland a biopsy will be taken. The closer to the edge of the prostate 1008 the lower the minimum section 1496 value should be. In turn, the closer to the edge of the prostate 1008 biopsies are taken the greater the number of total biopsies of the prostate 1088 will be taken. The needle lengths 1498 text box allows a user to specify the length of the biopsy tissue specimen removed. The system 1102 calculates the specific length necessary depending upon the location of the biopsy in prostate 1008. The designated tissue specimen length is rounded to the nearest 0.1 cm. The next selection determines if the entire tissue specimen length will be inside the capsule, if a small amount of the biopsy core will be outside the capsule, or if the biopsy core is to be as close to the capsule as possible. Selecting the use closest 1500 radio button causes the system 1102 to designate needle lengths that are as close to the capsule as possible. Selecting the inside capsule 1502 radio button causes the system 1102 to select needle lengths that are always inside the capsule. Selecting the outside capsule 1504 radio button causes the system 1102 to select needle lengths that may end up outside of the capsule, and would require the use of more biopsy needles, require the biopsy of longer core bed lengths, or both. The next selection allows the use of biopsy needles having a core bed length that is less than the longest core length required to be taken. Selecting the allow multiple inline biopsies 1506 box allows a user to use standard biopsy needles having a fixed core length from about 17 mm to about 20 mm. A biopsy schematic 1508 below the selections provides an interpretation of the selections, and a written instructions 1510 portion below the biopsy schematic 1508 provides an explanation of the selections above. Selecting a clear biopsies first 1512 box in the bottom left of the BPGUI 1494 clears each biopsy site from view on the image frame 1152 after the biopsy is taken. Selecting the generate 1514 button in the bottom right corner of the BPGUI 1494 generates the biopsy plan.

Figure 58:
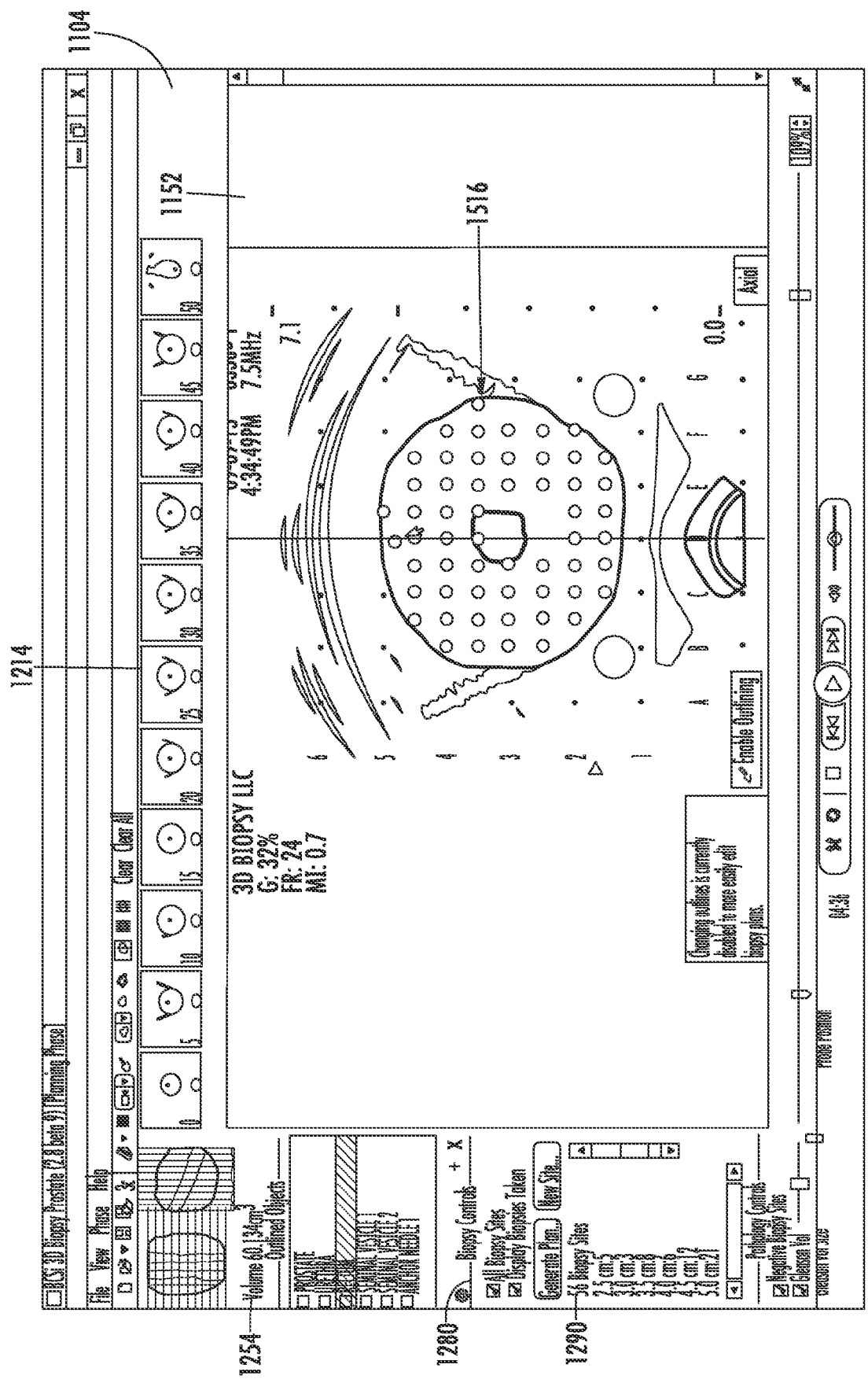

Referring to FIG. 58, the biopsy plan is shown over the sixth contour image 1214 or sixth slice located at about the mid-point of the prostate 1008. The biopsy plan is represented by an array of dots 1516 indicating the intended biopsy needle positions. The biopsy control frame 1280 indicates the number of biopsy sites 1290 represented by the array of dots 1516. In the example shown in FIG. 58, 56 biopsy sites are shown, as well as the length of the core, and the number of biopsy needles with a given core length needed to complete the biopsy plan. The number of biopsy sites and the various core lengths and number of needles are determined by the system 1102 by the length specified by the minimum section 1496, the needle lengths 1498, the capsule radio button selected, and whether allow multiple inline biopsies 1505 is selected. For example, because in the example shown in FIG. 57 the selections were a minimum section 1496 of 2.0 cm, needle lengths 1498 of 2.5 cm, 3.0 cm, 4.0 cm, 4.5 cm, and 5.0 cm, and use closest 1500, the biopsy plan 1286 generated a plan requiring 5 biopsy needles with a core length of 2.5 cm, 3 biopsy needles with a core length of 3.0 cm, 8 biopsy needles with a core length of 3.5 cm, 6 biopsy needles with a core length of 4.0 cm, 12 biopsy needles with a core length of 4.5 cm, and 21 biopsy needles with a core length of 5.0 cm are needed. In some embodiments, the system 1102 will calculate and display the probability of encountering a lesion of a particular size within the prostate 1008 using a given biopsy plan and an array of biopsy needle positions.

Figure 59:
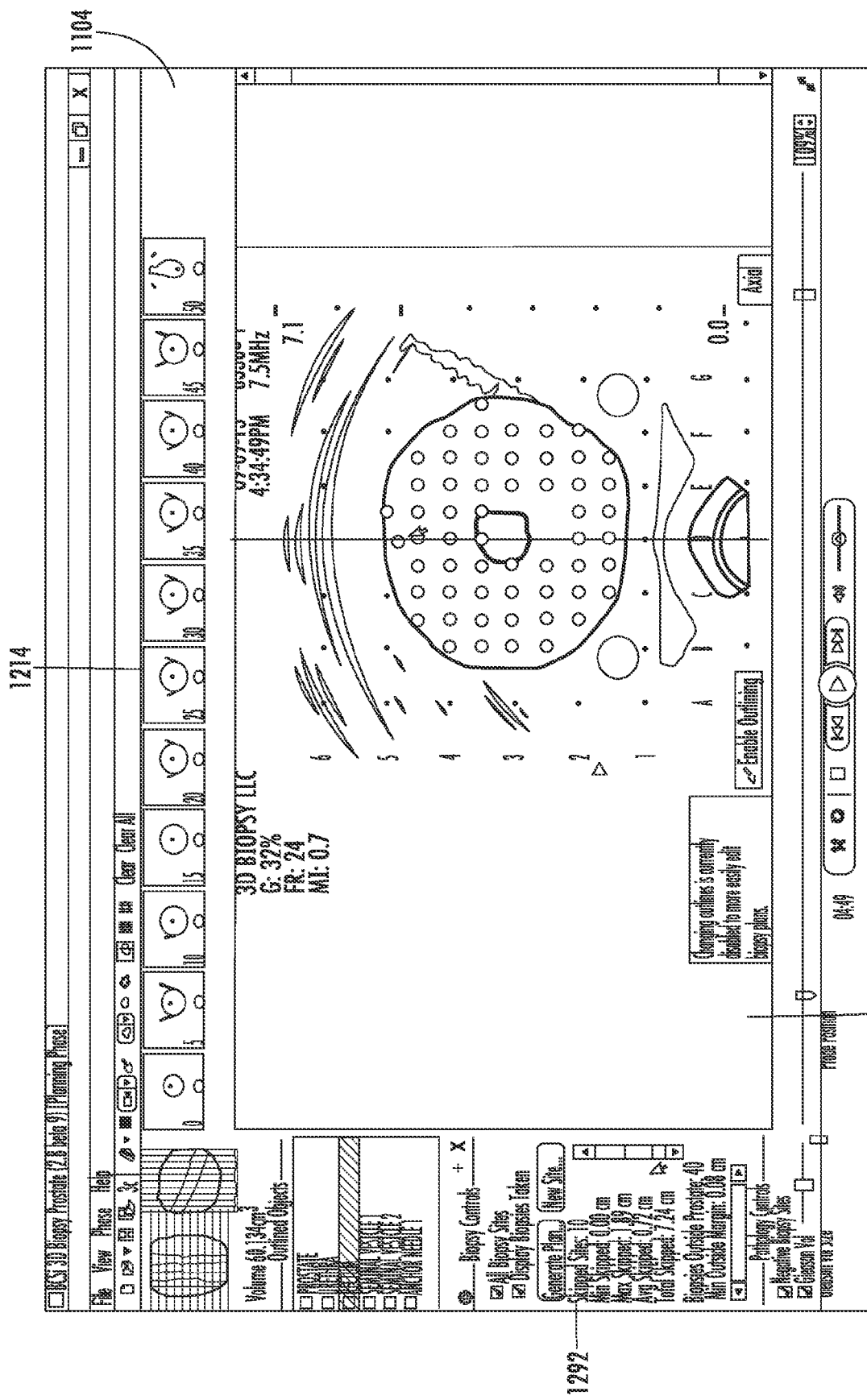
Figure 60:
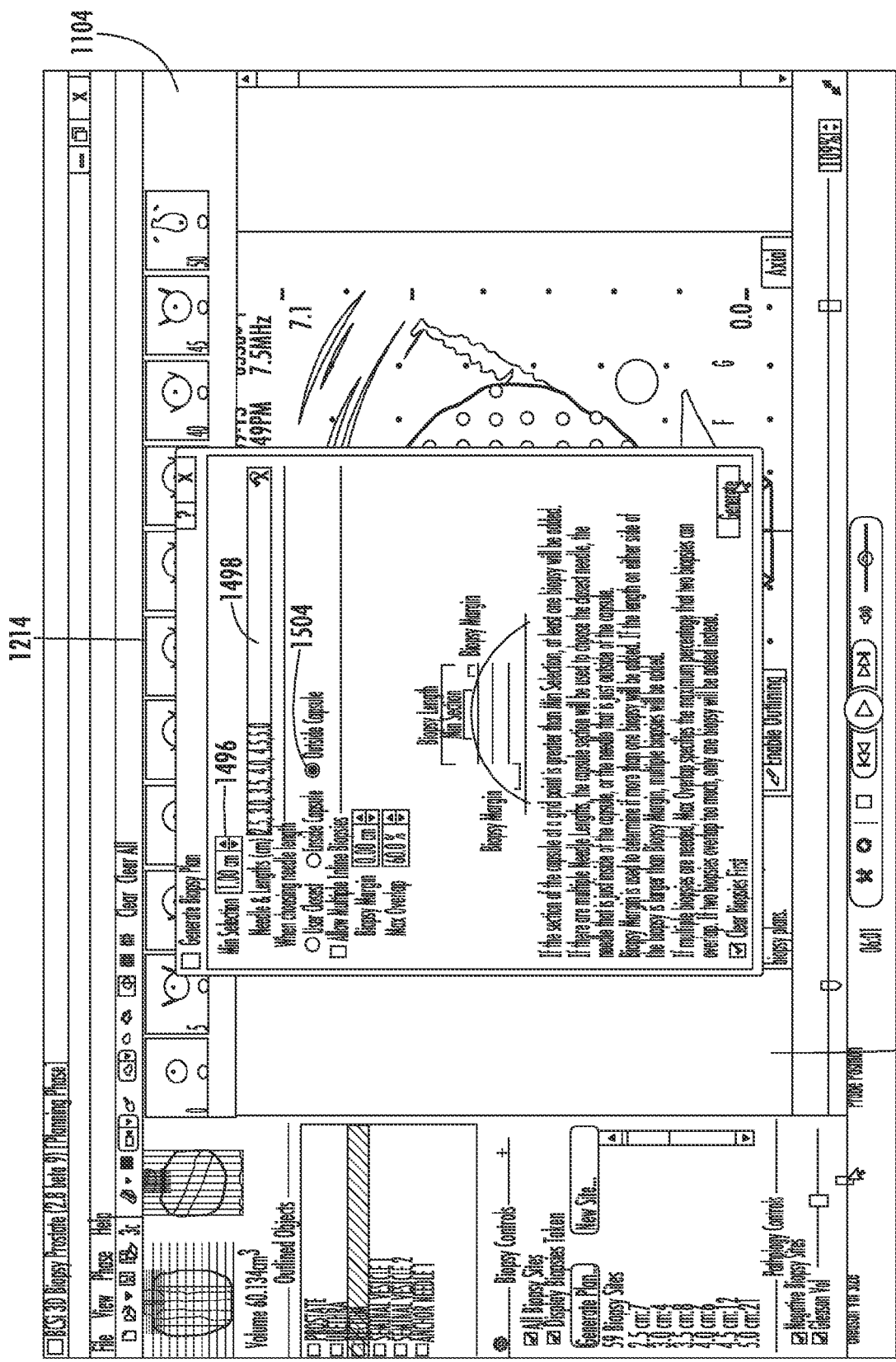

Referring to FIG. 59, scrolling down below the biopsy sites 1290 displays the skipped sites 1292 and the total tissue volume skipped. For example, 10 sites were skipped totaling 7.24 cm$^3$. The number of skipped sites is calculated based on the input criteria. For example, if the minimum section 1496 is increased, then less of the prostate is available for biopsy. The skipped sites 1292 information allows a user to evaluate the biopsy plan and make changes to the biopsy plan to increase the amount of tissue included in the biopsy plan. The user can refer to the probability calculation above to determine if any changes to the biopsy plan improve the biopsy plan. For example, the higher the probability of encountering a lesion of the tissue of a certain size is an improvement in the biopsy plan. Referring to FIG. 60, a minimum section 1496 of 1.0 cm, needle lengths 1498 of 2.5 cm, 3.0 cm, 4.0 cm, 4.5 cm, and 5.0 cm, and outside capsule 1504 was selected, and the biopsy plan 1286 generated a plan requiring 7 biopsy needles with a core length of 2.5 cm, 4 biopsy needles with a core length of 3.0 cm, 8 biopsy needles with a core length of 3.5 cm, 6 biopsy needles with a core length of 4.0 cm, 12 biopsy needles with a core length of 4.5 cm, and 21 biopsy needles with a core length of 5.0 cm are needed, totaling 59 biopsy sites. As a result, the number of skipped sites 1292 decreased from 10 to 7, and the total tissue volume skipped dropped from 7.24 cm$^3$ to 1.79 cm$^3$.

Figure 61:
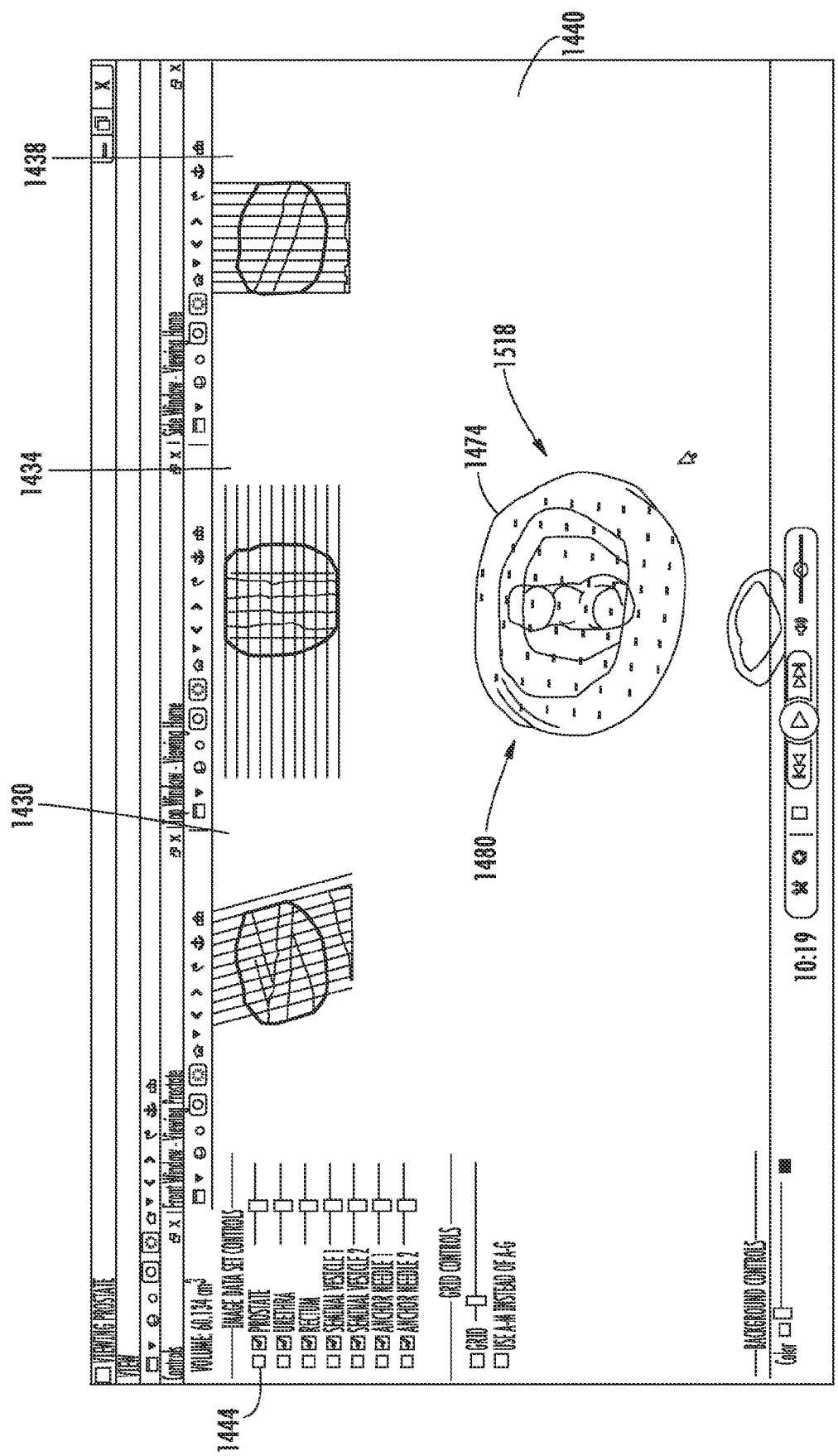
FIGS. 61-64 are illustrations of a graphical user interface according to some embodiments of the disclosed subject matter for viewing the paths of the biopsy needles.
Figure 62:
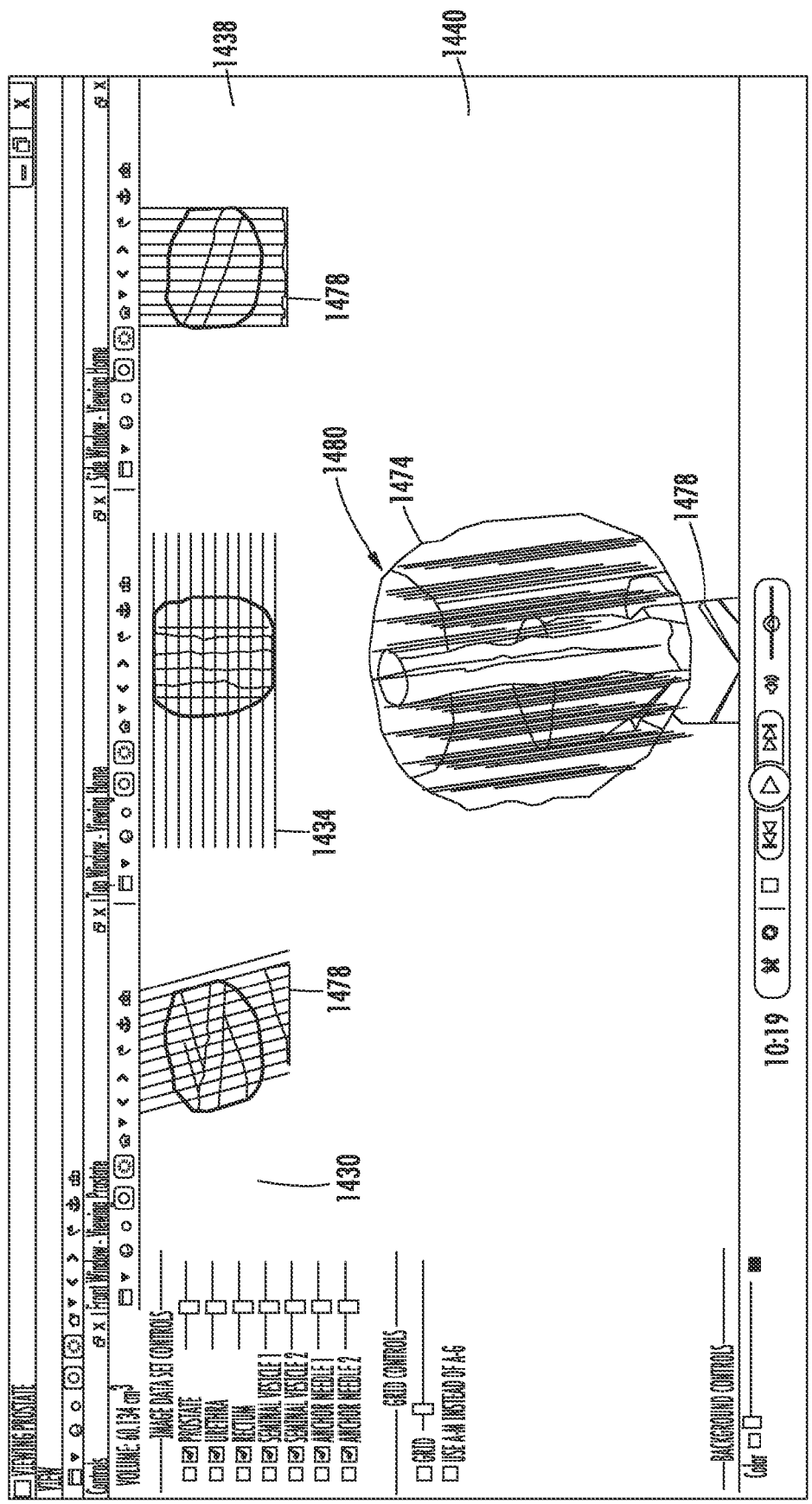
Figure 63:
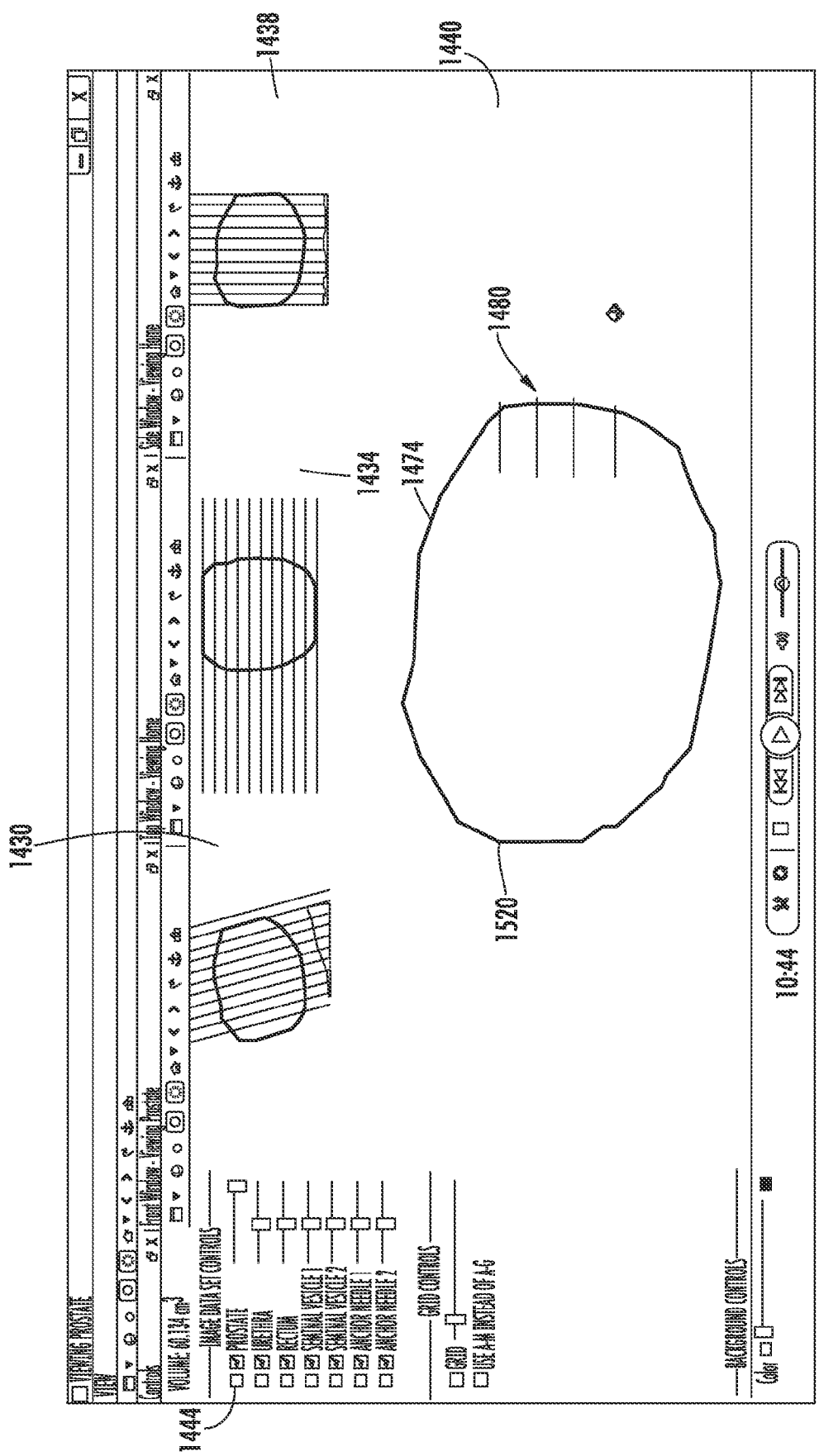
Figure 64:
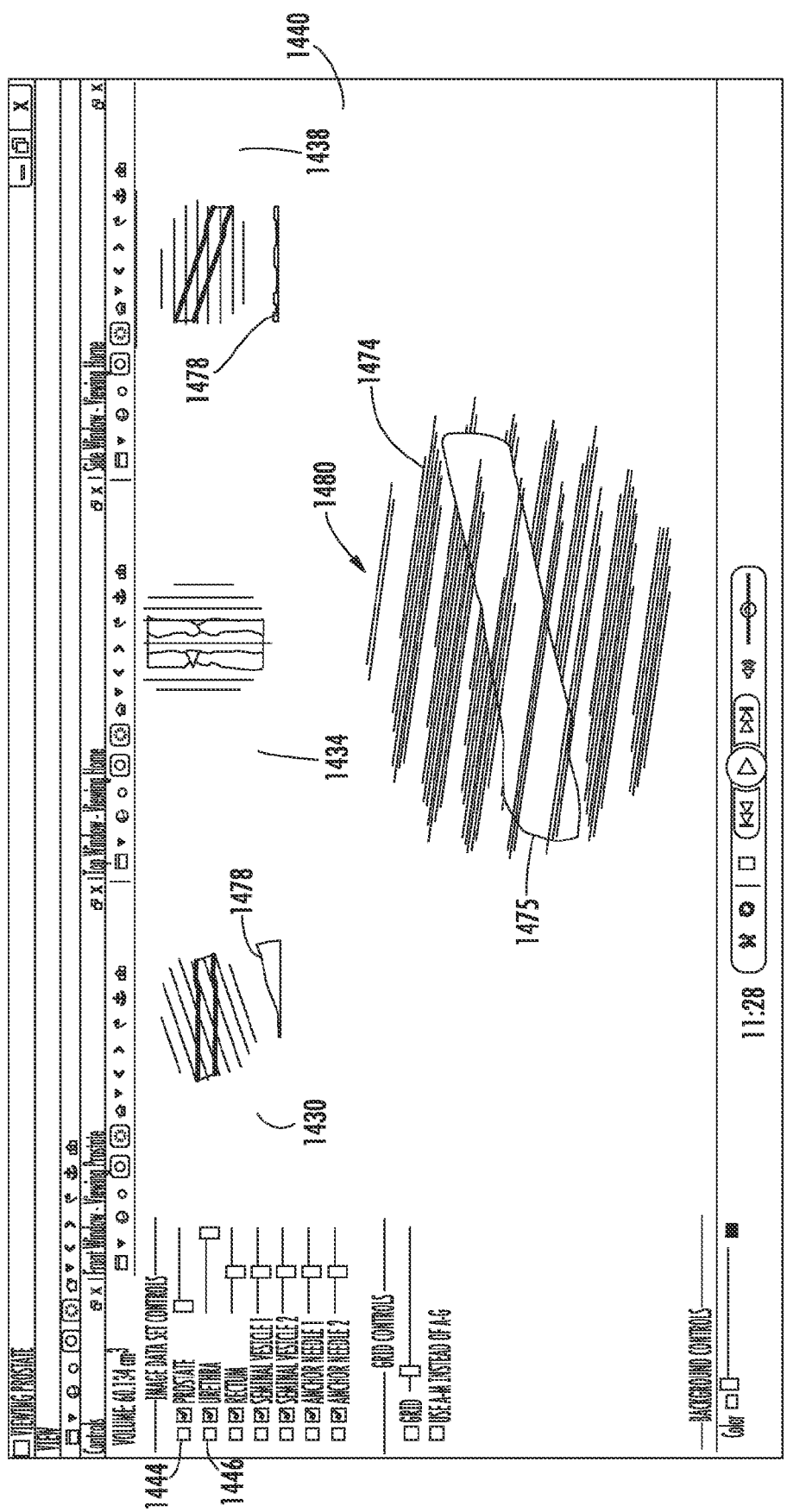
Figure 65:
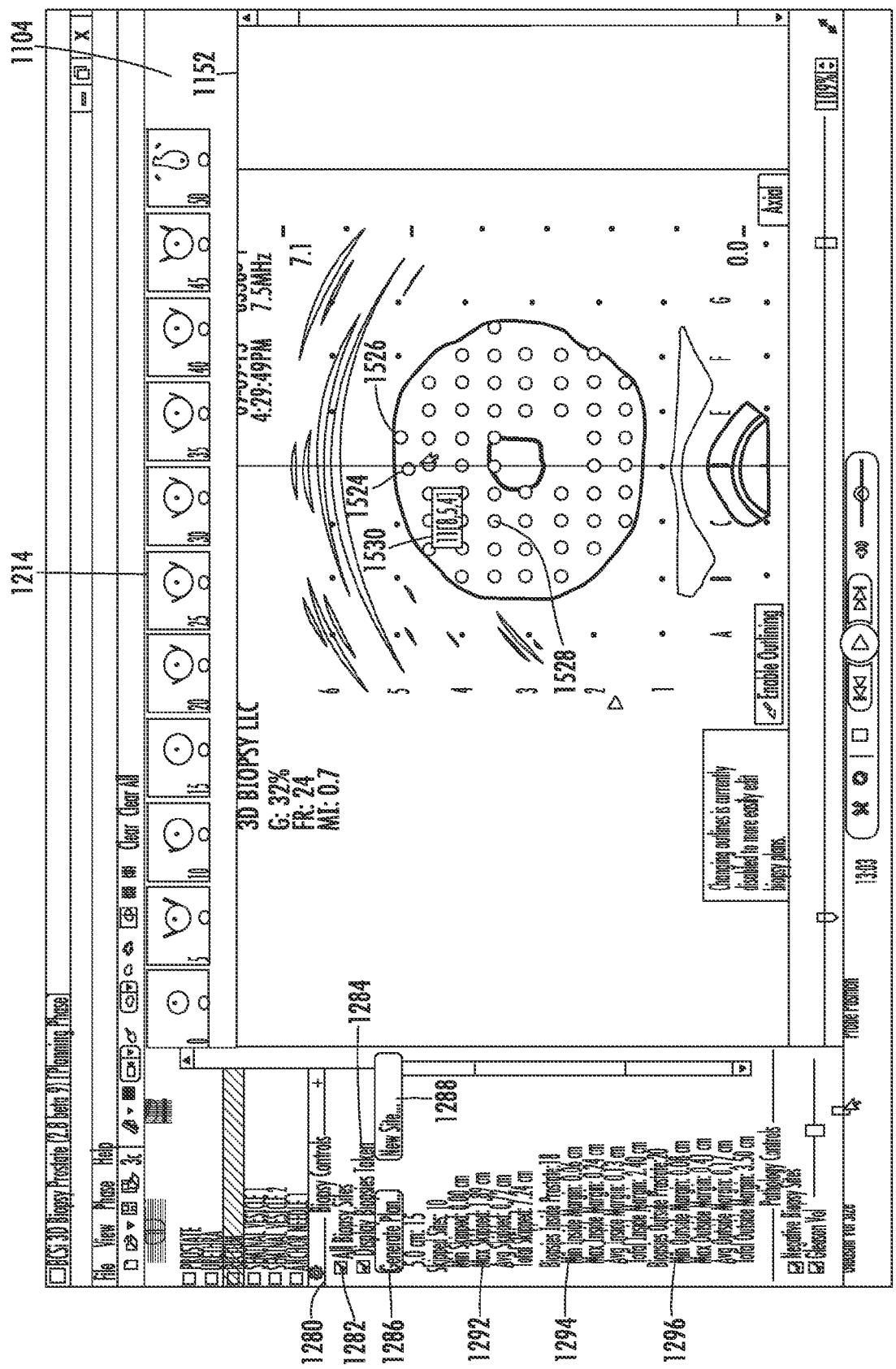
FIGS. 65-71 are illustrations of a graphical user interface according to some embodiments of the disclosed subject matter for viewing information about the individual biopsy sites.

After generating a biopsy plan and making adjustments to the variables as necessary, a user can view the orientation of the biopsy needles 1480 in the three-dimensional prostate image 1472. Returning to the 3DGUI 1402 frame (FIGS. 61-64), three-dimensional images of the prostate with needle 1480 paths determined by the biopsy plan are rendered in the 3DGUI 1402 frame from the plurality of contour images generated above, including a rotatable, isometric, three-dimensional image of the prostate with needles image 1518 rendered in the image frame 1440. Accordingly, the front view window 1430 displays an image of the front of the prostate with needles image 1518, the top view window 1434 displays an image of the top of the prostate with needles image 1518, and the elevation view window 1438 displays an image of the side of the prostate with needles image 1518. In FIG. 61, the prostate with needles image 1518 is viewed with the apex in the foreground and the base in the background. In FIG. 62, the prostate with needles image 1518 is viewed from above the prostate with the rectum below, and the path of biopsy needles that pass through the prostate above the urethra. The prostate with needles image 1518 can be rotated in three dimensions about a central axis using a cursor to view the biopsy plan from all angles. In FIG. 63, the slider control for the prostate 1444 has been moved from the middle of the slider to the right of the slider to increase the intensity of the color of the prostate margin 1474 causing it to become opaque, providing contrast for the portions of the needles 1480 of the plan that extend outside of the prostate margin 1474, represented by straight lines 1520. In FIG. 64, the slider control for the prostate 1444 has been moved to the left of the slider to decrease the intensity of the color of the prostate margin 1474 causing it to become transparent, and the slider control for the urethra 1446 has been moved from the middle of the slider to the right of the slier to increase the intensity of the color for the urethra margin 1475 causing it to become opaque, allowing a user to evaluate the positions of the needles 1480 around the urethra and make any adjustments to the biopsy plan based on the relationship between the needles 1480 and the urethra.

The three-dimensional representation of the prostate with needle image 1518 provides an operator with visualizations, and the ability to perform calculations, not otherwise attainable.

Biopsy Phase

Upon completion of the planning phase, biopsies may be taken in conjunction with the system 1102. A user returns to the biopsy plan in the image frame 1440. In the image frame 1440, the plurality of biopsy sites are represented by dots 1516. The biopsy sites of the biopsy plan are orientated so that biopsy site number 1 1524 is the most anterior and left site, with biopsy site number 2 1526 to the right of biopsy site number 1 1524. Biopsy site number 11 1528 is shown with a callout box 1530. When a user places a cursor over a biopsy site a callout box is displayed showing the biopsy site number and coordinates. The biopsy site number and coordinates represent the position on the software grid 1344 which corresponds to the same location on the coordinate system 1022 on the template 1018, allowing a user to biopsy needle into the correct aperture 1020 of the template 1018 so the needle enters the prostate as viewed on the ultrasound image 1040. The callout box 1530 for biopsy site number 11 shows the site is number "11," and the coordinates are "B.5,4," referring to coordinate position "B.5" on the x-axis of the coordinate system 1022, and coordinate position "4" on the y-axis of the coordinate system 1022.

Figure 66:
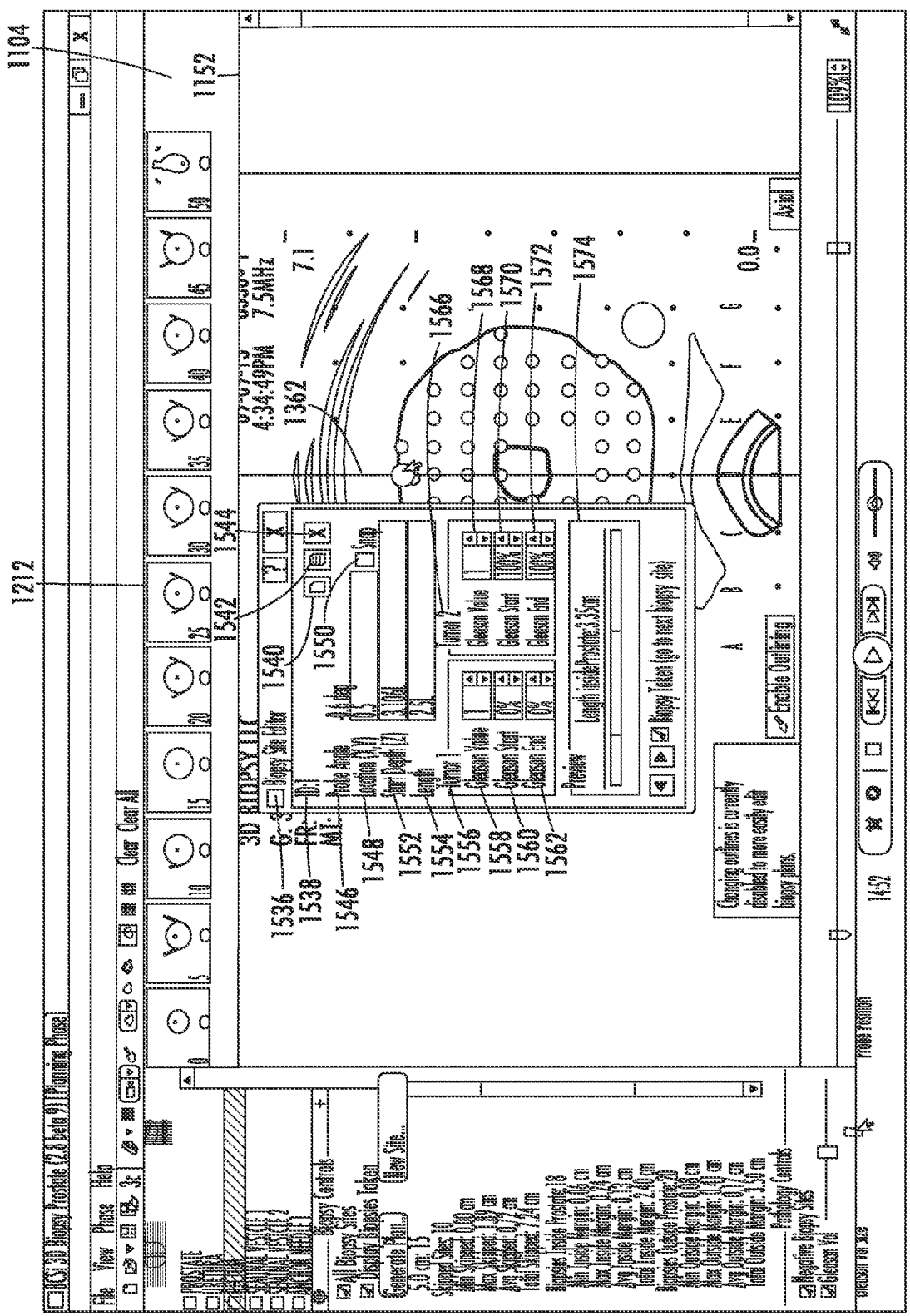

Selecting a biopsy site with the cursor opens a biopsy site editing graphical user interface (BSEGUI) 1536 frame. Referring to FIG. 66, a BSEGUI 1536 for biopsy site number 1 1524 is shown in line with the probe centerline 1362. The BSEGUI 1536 displays a biopsy site label 1538 corresponding to the biopsy site selected, here, a "1" for biopsy site number 1 1524. The new page button 1540 is for adding a new biopsy site to the biopsy plan. The copy button 1542 is for copying an existing site to the biopsy plan. The close button 1544 is for closing the biopsy site window. The probe angle 1546 is shown indicating the position of the biopsy site that deviated from the location 1548, wherein a probe angle 1546 of "0" indicates no deviation. In FIG. 66, the biopsy site location 1548 is at the "D" position so the probe angle 1546 is "0." If the biopsy site is to the left of the midline location 1548 "D" the probe angle 1546 would be represented by a negative number and conversely if it was to the right of the midline location 1548 "D" the probe angle 1546 would be a positive number. The probe angle 1546 represents how far to rotate the ultrasound probe 1036 (discussed below) so the intended biopsy needle is in the field of view of the probe 1036 when imaging is switched from axial to sagittal view. In some embodiments, a guide line represented by a probe centerline 1362 is shown on the image frame 1152 allowing the user to rotate the ultrasound probe 1036 so the probe centerline 1362 is in the "0" position or passing through the "D" position. The coordinate location 1548 of the biopsy site corresponds to the coordinate system 1022 on the template 1018 indicating the location of the aperture 1020 along the x-axis and the y-axis where the user will insert the biopsy needle assembly to take the biopsy tissue specimen. Here the coordinate location 1548 is "D, 5." The snap 1550 box is for locking the position of the biopsy needle presenting the needle from being moved. The start depth 1552 of the biopsy site corresponds to the depth within the prostate that the biopsy specimen will be taken calculated by the system 1102. The length 1554 is the required length of the core bed of the biopsy needle calculated by the system 1102 to take a biopsy tissue specimen at the selected biopsy site.

Figure 67:
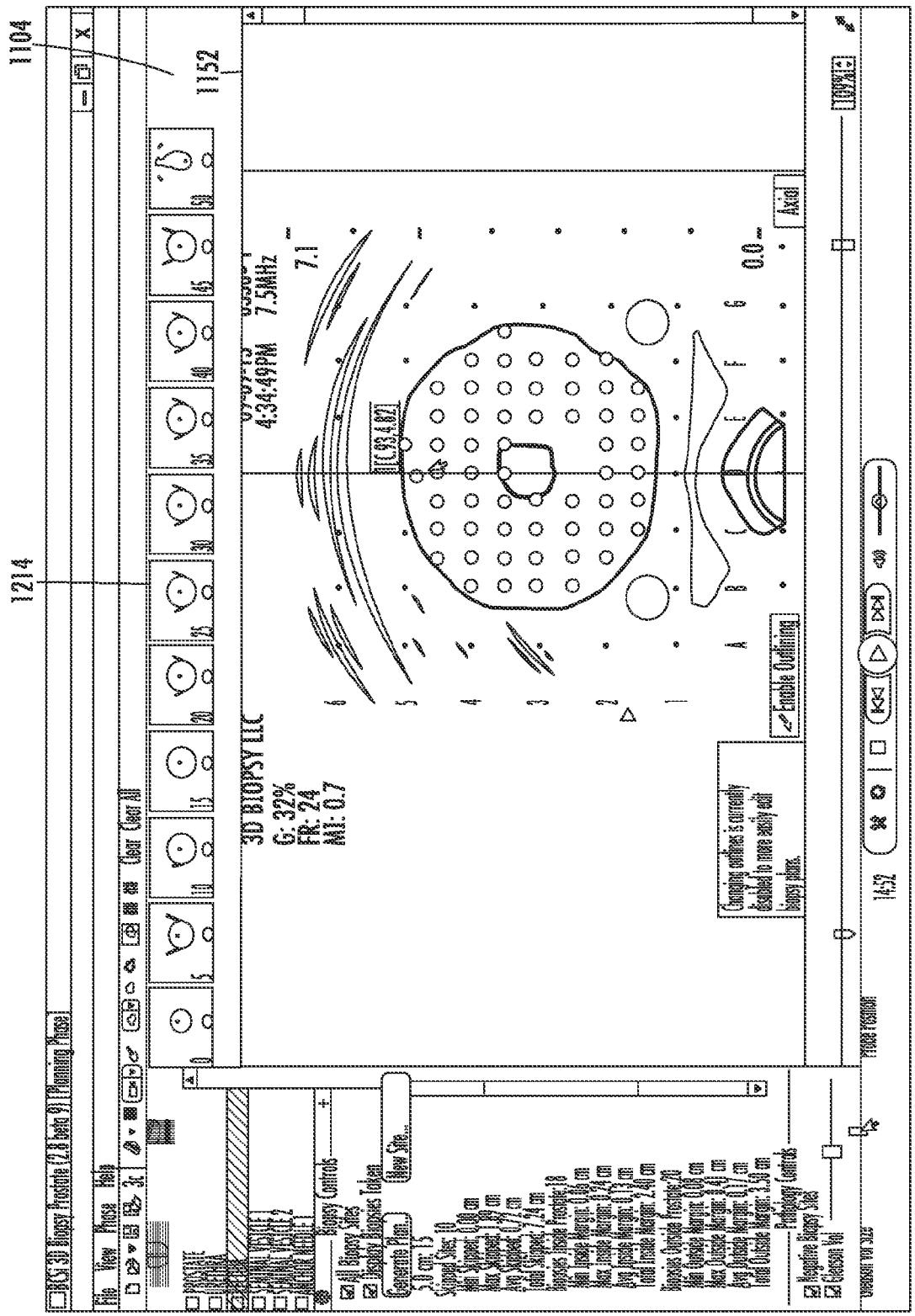

To take the first biopsy a user selects a biopsy needle assembly having a biopsy needle with a core bed length specified by the length 1554. In some embodiments, the user may select the needle assembly 100 above wherein the inner component 102 core bed 116 length between the first end 118 and second end 120 is equal to or greater than length 1554. In an embodiment, the actuator assembly 200 is used with the needle assembly 100 to excise a biopsy specimen specified by the length 1554 by setting the length of travel of the inner component 102. The user advances a biopsy needle assembly through the aperture 1020 corresponding to the biopsy site label 1538. Referring to FIG. 67, when a biopsy needle is inserted through the designated aperture in the template 1018 it may enter the prostate 1008 at a slightly different location than indicated on the BSEGUI 1536. This may be caused by the location of the apertures 1020 of template 1018 when it is placed against the perineum not being perfectly aligned to the ultrasound grid 1332. In addition, as the biopsy needle assembly enters the prostate 1008 from the perineum, it moves the gland away from its position within the patient's 1002 body thereby what was, for example, coordinate location "D, 5" may now be essentially coordinate location "C .93, 4.92", meaning the actual coordinate of the biopsy needle indented for "D, 5" is 0.07 cm to the left of D at position 0.08 cm below 5.

Figure 68:
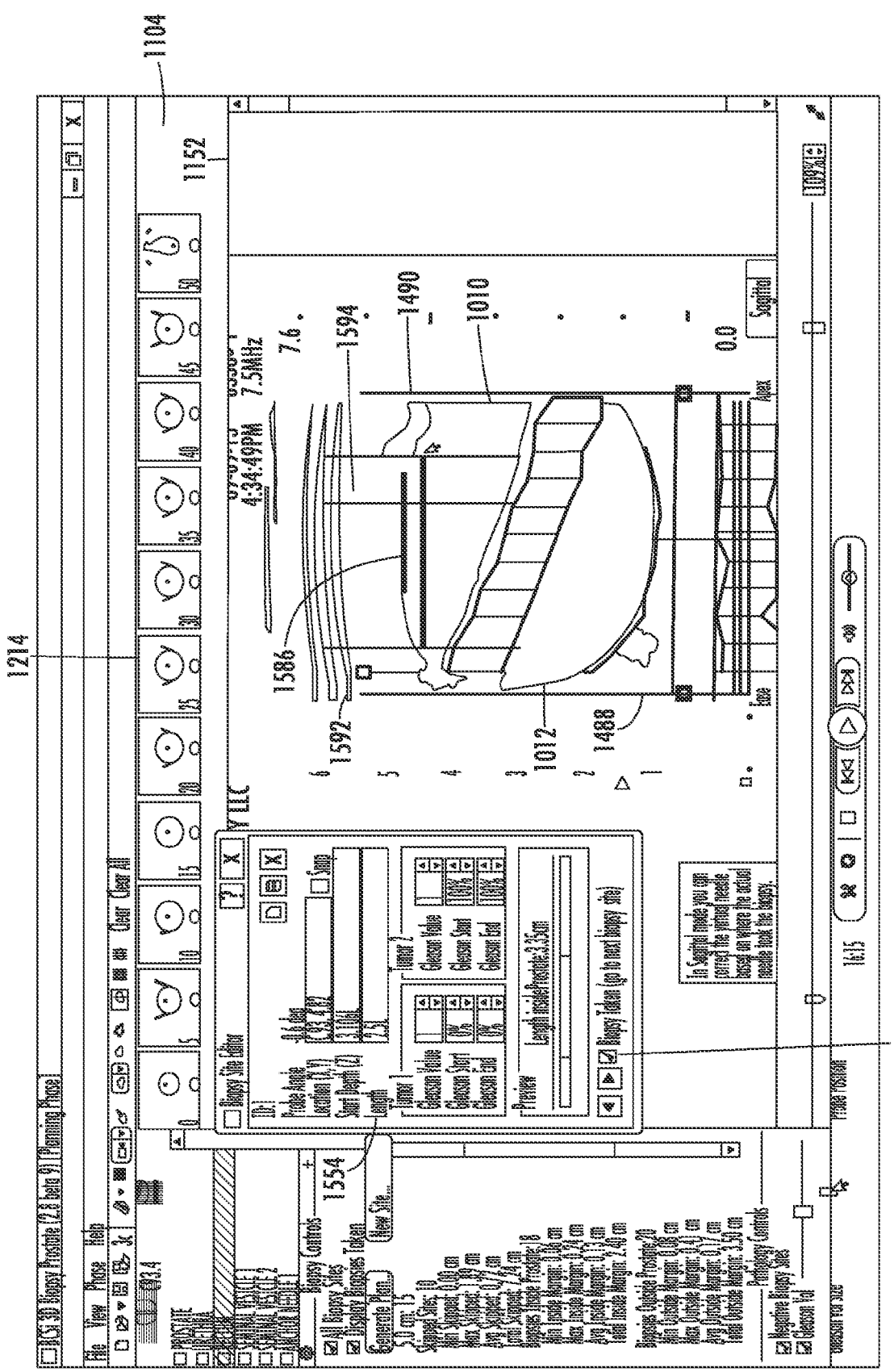

As the user advances the biopsy needle assembly toward the prostate 1008 the view in the image frame 1152 is changed to a sagittal image or a longitudinal cross section of the prostate 1008 from the base 1012 to the apex 1010 is shown in the image frame 1152, and a sagittal image or longitudinal cross section 1482 of the three-dimensional prostate image 1472 overlays the image 1040 of the prostate 1008 (FIG. 68). The length 1554 and location of the biopsy is shown on the ultrasound image 1040 as a virtual biopsy specimen 1586. The virtual biopsy site specimen 1586 extends between a first end adjacent the base 1012 of the prostate 1008, a second end adjacent the apex 1010 of the prostate 1008, and includes a cross sectional width. In some embodiments, the virtual biopsy specimen 1586 is represented as a yellow line having a height representing the cross sectional width, and extends between a vertical first end line 1592 representing the first end and a vertical second end line 1594 representing the second end. The user may then examine the cross section and evaluate the intended biopsy site. When the biopsy needle is viewed on the ultrasound image 1040, and it is not perfectly superimposed with the virtual biopsy specimen 1586, the user selects the site and moves a yellow dot that is superimposed on the inserted biopsy needle. The new location 1548 of "C.93, 4.92" now represents the true position of the biopsy needle in the three-dimensional prostate image 1472. The user can decided if the new location is acceptable and whether any changes need to be made to the biopsy sites of the surrounding needles.

Figure 69:
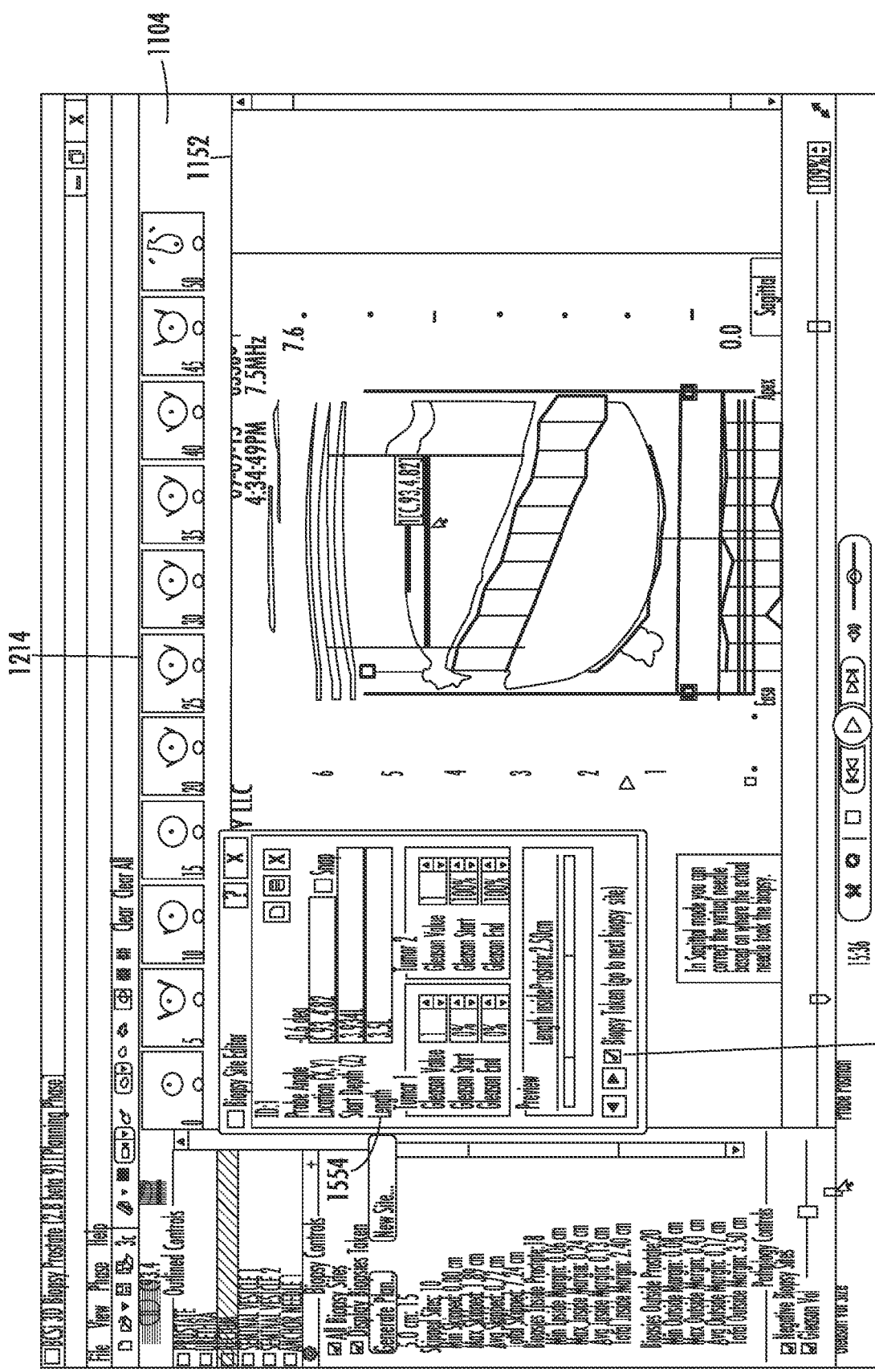

Referring to FIG. 68, an assessment of biopsy site number 1 1524 indicates the suggested length 1554 of 2.5 cm for the biopsy specimen is of insufficient length to extend between the margin of the prostate 1008 from a first point adjacent the apex 1010 and a second point adjacent the base 1012. The user may change the recommended length of the biopsy core to a revised length of the biopsy core. Referring to FIG. 69, the biopsy core length was changed from a recommended length of 2.5 cm to a revised length of 3.5 in the BSEGUI 1536 by changing the length 1554 from 2.5 to 3.5. The length selected will depend on the appearance of the virtual biopsy specimen 1586 on the ultrasound image 1040. Adjusting the length of the biopsy core taken allows the biopsy core to sample tissue from the full length of the prostate 1008 at that site. In addition to adjusting the length of the biopsy specimen, the vertical location or height of the virtual biopsy specimen 1586 can be adjusted on the ultrasound image 1040 by selecting the virtual biopsy specimen 1586 and moving it up or down along the y-axis, and the horizontal location of the virtual biopsy specimen 1586 can be adjusted as well by moving it right or left along the z-axis. Repositioning of the virtual biopsy specimen 1586 ensures the that the ultrasound image of the biopsy needle and the virtual biopsy specimen 1586 are superimposed ensuring the virtual biopsy specimen 1586 accurately reflects the position of the biopsy removed from the prostate.

Figure 70:
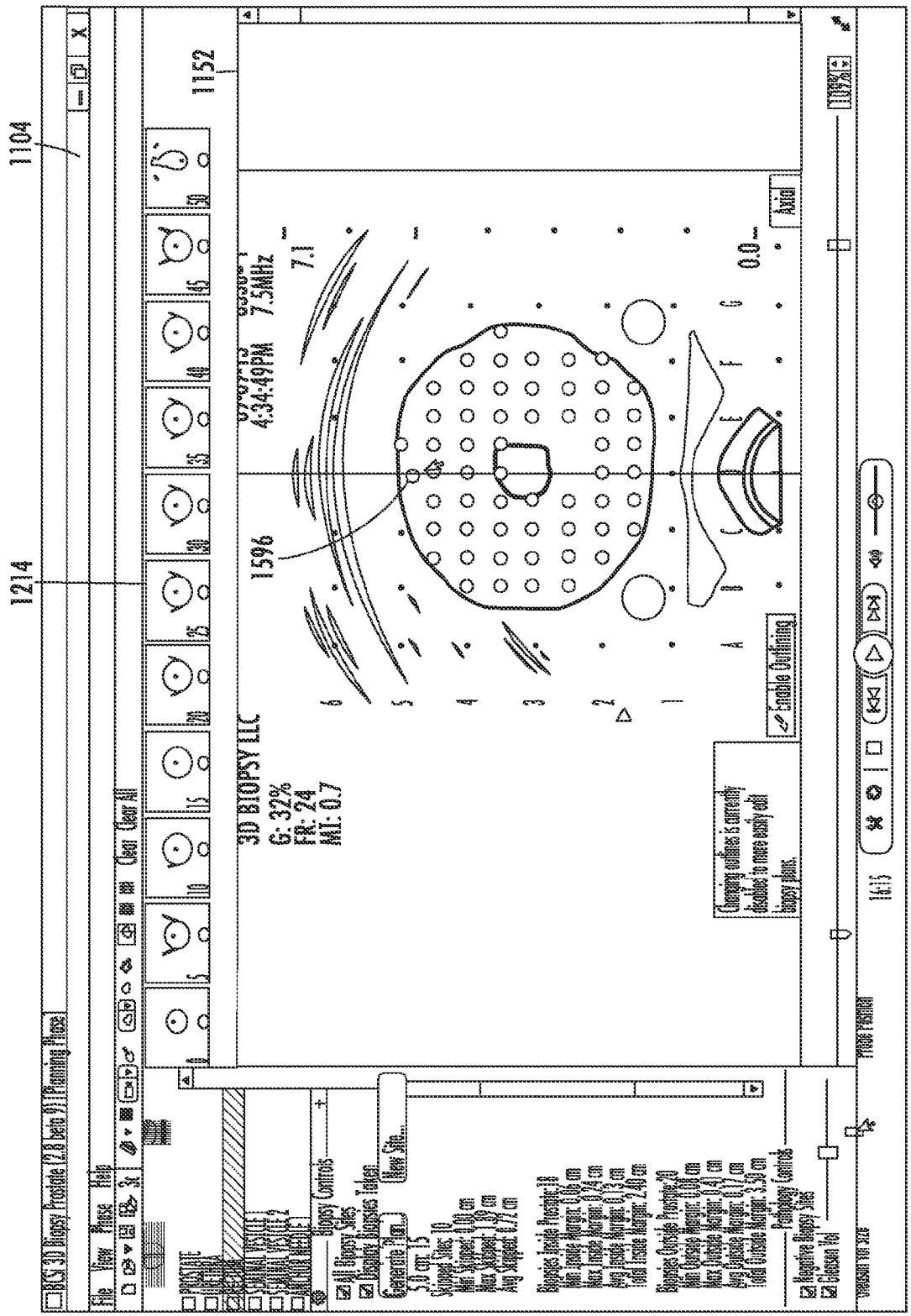

Because the length 1554 was changed, in some embodiments, use of the needle assembly 100 allows the user to adjust the length of travel of the inner component 102 to excise a biopsy core corresponding to the revised length, regardless of whether the needle assembly 100 is in the patient 1002 or not. The biopsy tissue specimen is taken and the tissue specimen is removed from the prostate 1008 for pathological examination. The user selects the biopsy taken 1582 box and the biopsy site dot turns to a red dot 1596 in the image frame 1152 (FIG. 70).

In some embodiments, the system 1102 prints a label using a printer connected to the computer after selecting the biopsy taken 1582 box. The label includes information identifying the patient, including the patient's name, the patient's identifying number, a medical record number, date of birth, and other identifying information designated by the user, including the biopsy site number. The label is applied to the biopsy specimen container for the corresponding biopsy tissue specimen. In some embodiments, the label is applied to a collection vial 502 containing a cartridge assembly 400 enclosing the corresponding biopsy tissue specimen.

To take each subsequent biopsy to complete the biopsy procedure the user follows the steps above for identifying a biopsy site, selecting a needle, inserting the needle into the appropriate aperture 1018, adjusting the biopsy site values, excising the biopsy specimen, and depositing the specimen in a cartridge assembly and labeled collection vial.

Figure 71:
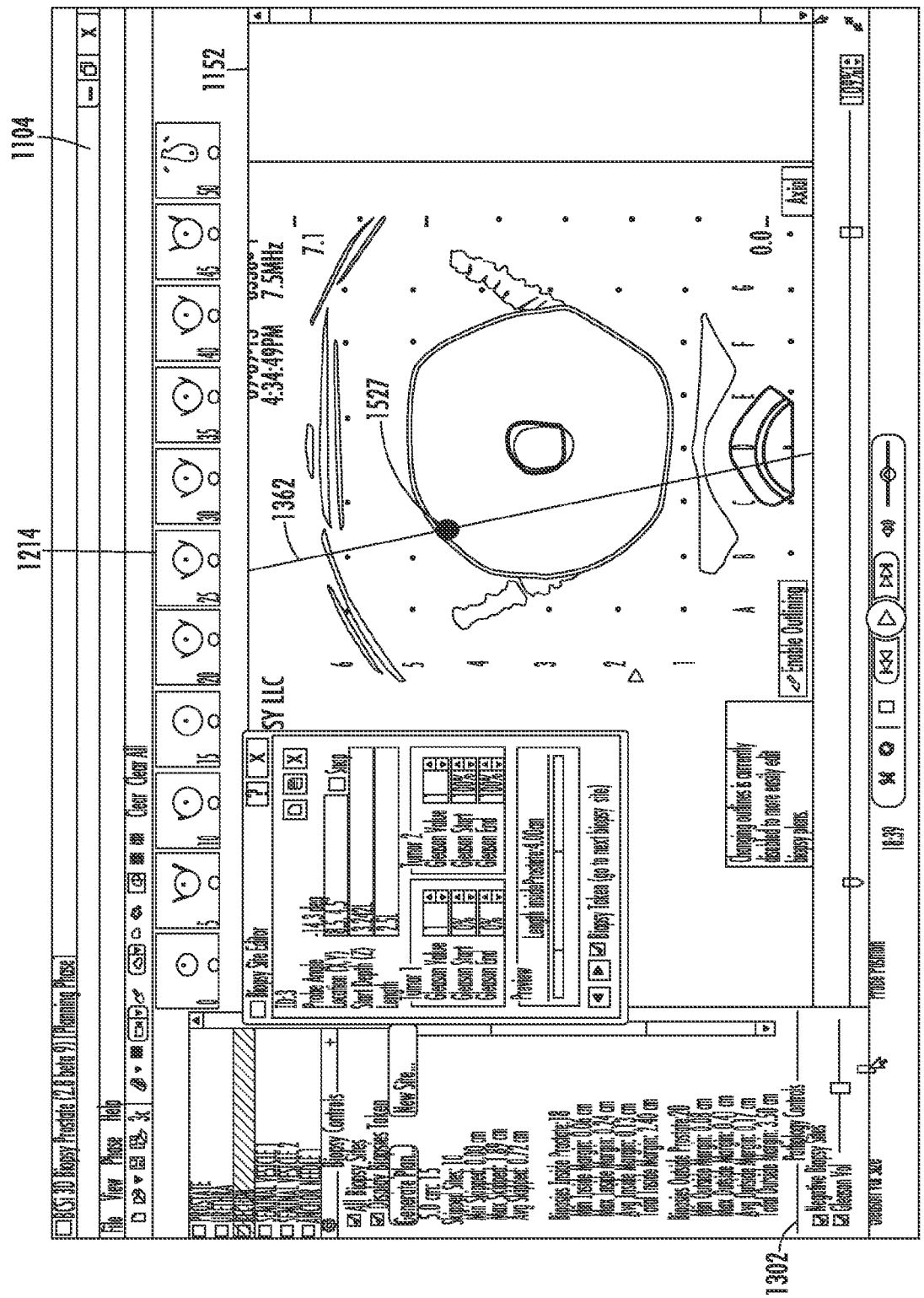

As the biopsy procedures progresses, adjustments to the position of the probe centerline 1362 may need to be performed to keep the virtual image aligned with the ultrasound image of the prostate 1008. Referring to FIG. 71, biopsy site number "3" 1527 has been selected as indicated by the biopsy site label 1538 in the BSEGUI 1536. Biopsy site number "3" 1527 is located lateral to the midline of the image. In order to keep the virtual image aligned to the ultrasound image the ultrasound probe 1036 will need to be rotated to the left aligning the probe centerline 1362 with biopsy site number "3" 1527. The user may then switch the view to sagittal and the virtual representation of the needle will now be represented in the proper location respective to the virtual image of the prostate 1008.

Upon completion of the biopsy phase the patient is discharged from the healthcare facility and returns for treatment using the system 1102 after completion of the pathology phase.

Pathology Phase

After the biopsy phase is complete the biopsy specimens are evaluated in a pathology phase and the results are recorded by the system 1102 in the pathology module 1110. Upon examination of a tissue specimen by a medical professional, including a pathologist, test results and remarks regarding the biopsy tissue specimen can by entered for each biopsy tissue specimen using the pathology module 1110. In an embodiment, markings made on the biopsy specimens from projections in the core bed 116 aid the medical professional in proper identification and orientation of the biopsy specimen and biopsy site. When lesions, such as cancerous tumors, are identified in a biopsy specimen the pathologist can report the Gleason score, and the locations, size, and regions of the tissue specimen presenting lesions.

Figure 72:
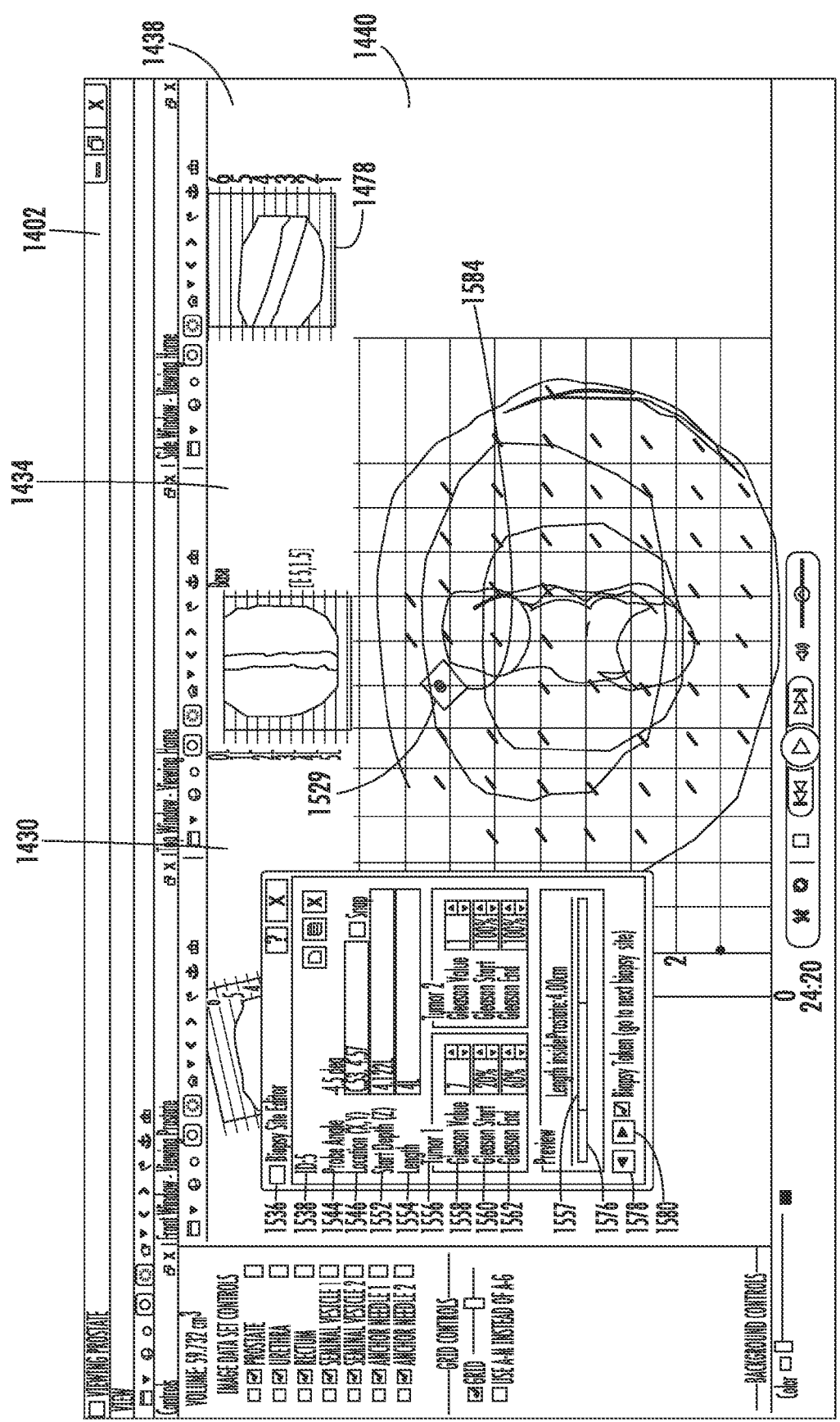
FIGS. 72-73 are illustrations of a graphical user interface according to some embodiments of the disclosed subject matter for viewing pathological information about the biopsy sites.

To enter pathology remarks for a specimen, a user selects a biopsy site on the image frame 1152 bringing up the BSEGUI 1536. Referring to FIG. 72, the BSEGUI 1536 for biopsy site "5" 1529 is shown. Returning to FIG. 66, remarks for a first pathology remark are entered in a first tumor frame 1556, and remarks for a second pathology remark, if necessary, are entered in a second tumor frame 1566. For a first tumor, a Gleason value 1558, a Gleason start 1560, and a Gleason end 1562 may be entered. For a second tumor, a Gleason value 1568, a Gleason start 1570, and a Gleason end 1572 may be entered. A preview frame 1574 includes a virtual image of the biopsy core, with the base of the core at the left, and the apex of the core at the right, with any regions of the biopsy specimen associated with the pathology remarks. The Gleason value 1558, 1568 ranges from about 1, representing the lowest grade to about 10, representing the highest grade. The Gleason start 1560, 1570 is the distance a given remark begins from the base, and the Gleason end 1562, 1572 is the distance the given remark ends from the base. In some embodiments, the Gleason start 1560, 1570 and the Gleason end 1562, 1572 are represented by numerical positions beginning from the base (left end) of the core, such as a Gleason start of 3 mm from the base of the core and a Gleason end of 10 mm from the base of the core. Accordingly, a tumor extending between the 3 mm from the base to 10 mm from the base would be a tumor of 7 mm in length.

Returning to FIG. 72, for biopsy site "5" 1529, the first tumor frame 1556 shows a Gleason value of 7, a Gleason start 1560 of 20%, and a Gleason end 1562 of 60%. Tumor "1" 1557 is shown as a segment of the virtual image, and shown as a three-dimensional tumor 1584 on the three-dimensional prostate image 1472. In some embodiments, tumor "1" 1557 is represented as a red segment. The biopsy length 1576 represents the length 1554 calculated above. The left arrow button 1578 allows the user to move to the previously numbered biopsy site, and the right arrow button 1580 allows the user to move to the subsequently numbered biopsy site.

After the tumor information has been entered for a biopsy site, the volume of the tumor 1584 can be adjusted using the pathology control frame 1302. The volume of the tumor 1584 would be adjusted by the pathologist to account for the location of surrounding biopsy sites that do not indicate the presence of tissue lesions thereby allowing the pathologist to set a maximum volume of prostate tissue at risk of containing a tumor when planning a treatment in the treatment phase.

Figure 73:
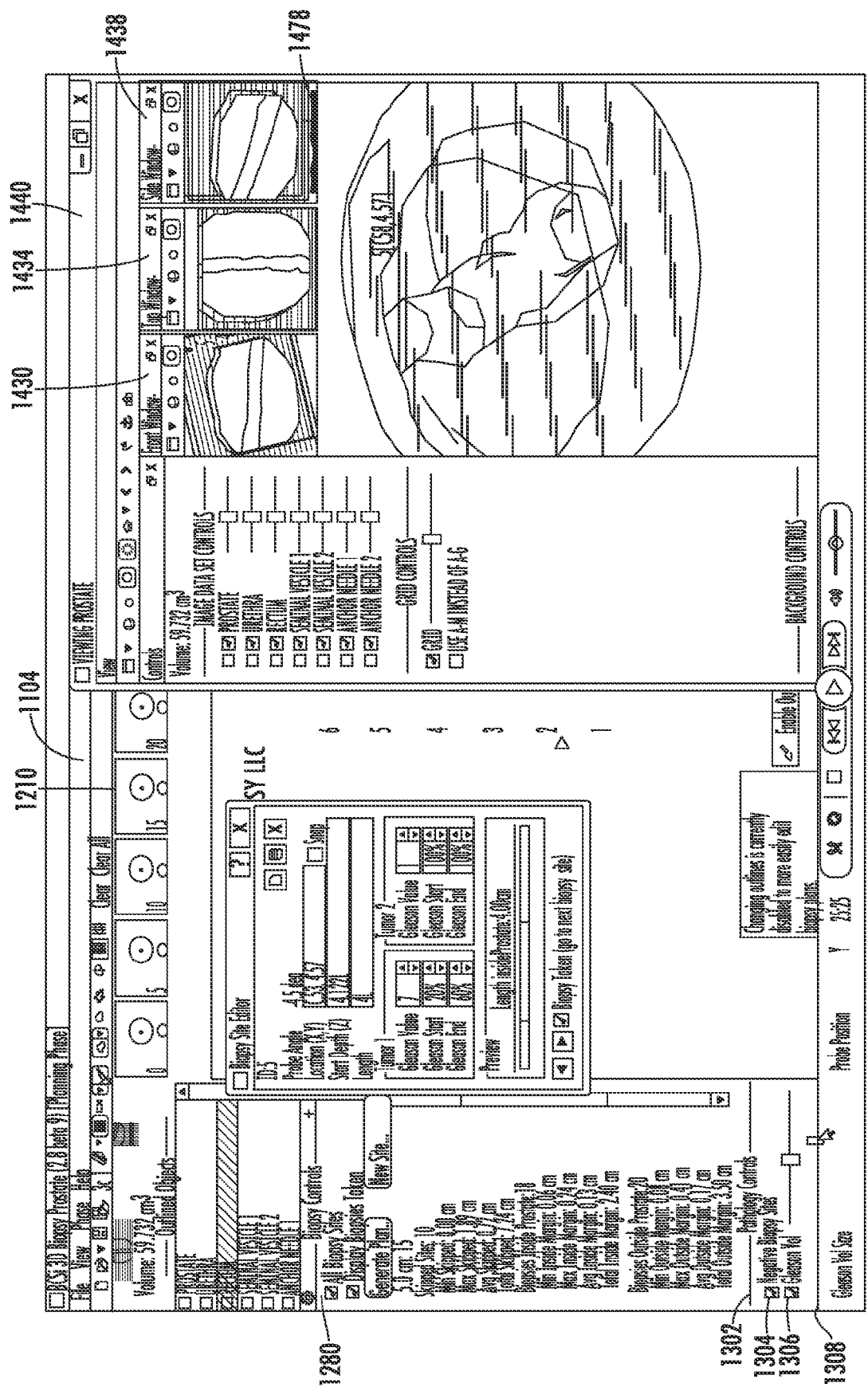

Referring to FIG. 73, the pathology control frame 1302 appears below the biopsy control frame 1280. The pathology control frame 1302 allows a user to select whether to show negative biopsy sites 1304 to reflect the portion of the biopsy specimen not designated as a tumor, adjust the Gleason volume 1306 using a slider, and the Gleason volume size 1308 using a slider.

Treatment Phase

After the pathology phase is complete a treatment plan is set up for the patient. Treatments can be administered to the patient using the treatment module 1112 of the system 1102. To begin the treatment phase, the patient 1002 is again positioned for a procedure as shown and described above with the imaging system 1032, TRUS probe 1036, and template 1018 prepared for use.

Figure 74:
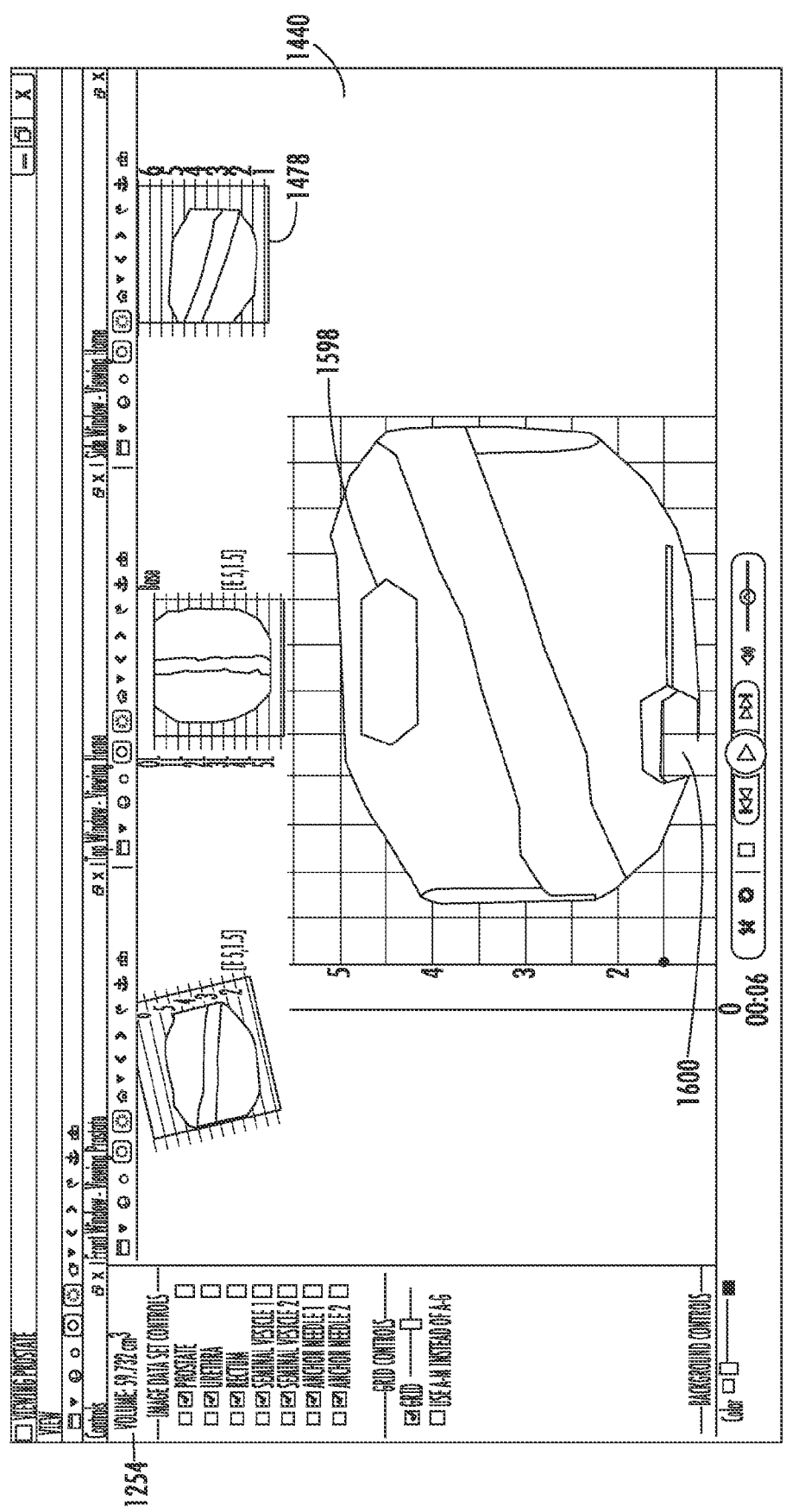
FIG. 74 is an illustration of a graphical user interface according to some embodiments of the disclosed subject matter for viewing the lesions in the three-dimensional images.

Referring to FIG. 74, the three-dimensional reconstruction 1174 is shown in the image frame 1440 with virtual representations of any lesions 1598, 1560 superimposed thereon. Any mismatching of the margins of the gland are corrected with the contour tools. The base and apex of the three-dimensional reconstruction 1174 of the prostate and associated structures are aligned on the ultrasound mage 1040 as described in the biopsy phase above (FIGS. 68-69). The three-dimensional reconstruction 1174 now displays the tissue structures and the extent of the lesions in the prostate. Thus, the treating urologist is able to visualize the lesions on the ultrasound image 1040 and insert ablative sources through a cannula such as the outer component 152 above, or the ablative source can be inserted into the lesions through the rectum. Alternatively, the positive biopsy plan can be exported to DICOM, or other images, which can be uploaded into another treatment planning system, for example IMRT, or Proton Therapy, and any focal ablation can be delivered in that manner.

In some embodiments, images acquired from other imaging systems 1032 can be uploaded into the system 1102 allowing a user to perform targeted biopsies and/or treatments. Such images include radiographic images, including magnetic resonance imaging, nuclear magnetic resonance imaging, and magnetic resonance tomography, and X-ray computed tomography images, including positron emission tomography, single-photon emission computed tomography, computed axial tomography, and computer-assisted tomography. In such an embodiment, lesions of interest are marked by the radiologist allowing the urologist to perform the image acquisition and then merge the images and three-dimensional reconstruction images at the time of the procedure. The user then has the option of performing biopsy or treatment on the marked lesions and additional biopsies or treatment in different regions of the prostate as warranted.

The biopsy phase and the treatment phase can be performed sequentially if the pathology phase and identification of tumors can be made within a short time after removing the biopsy tissue, thereby allowing the phases to be completed at one treatment visit and under one anesthesia.

It will be appreciated that the components of the system 1102 can be used for various other applications. Moreover, the system 1102 can be fabricated in various sizes and from a wide range of suitable materials, using various manufacturing and fabrication techniques.

It is to be understood that while certain aspects of the disclosed subject matter have been shown and described, the disclosed subject matter is not limited thereto and encompasses various other embodiments and aspects.

Figure 75:
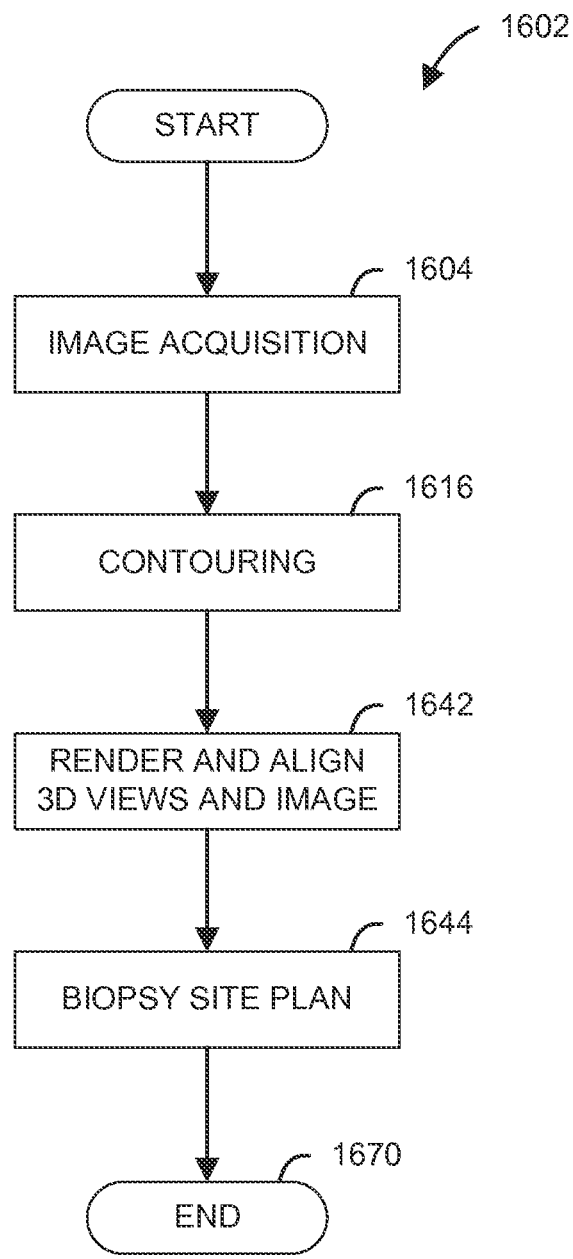
FIG. 75 is a diagram of a process of planning a biopsy procedure according to some embodiments of the disclosed subject matter.
Figure 76:
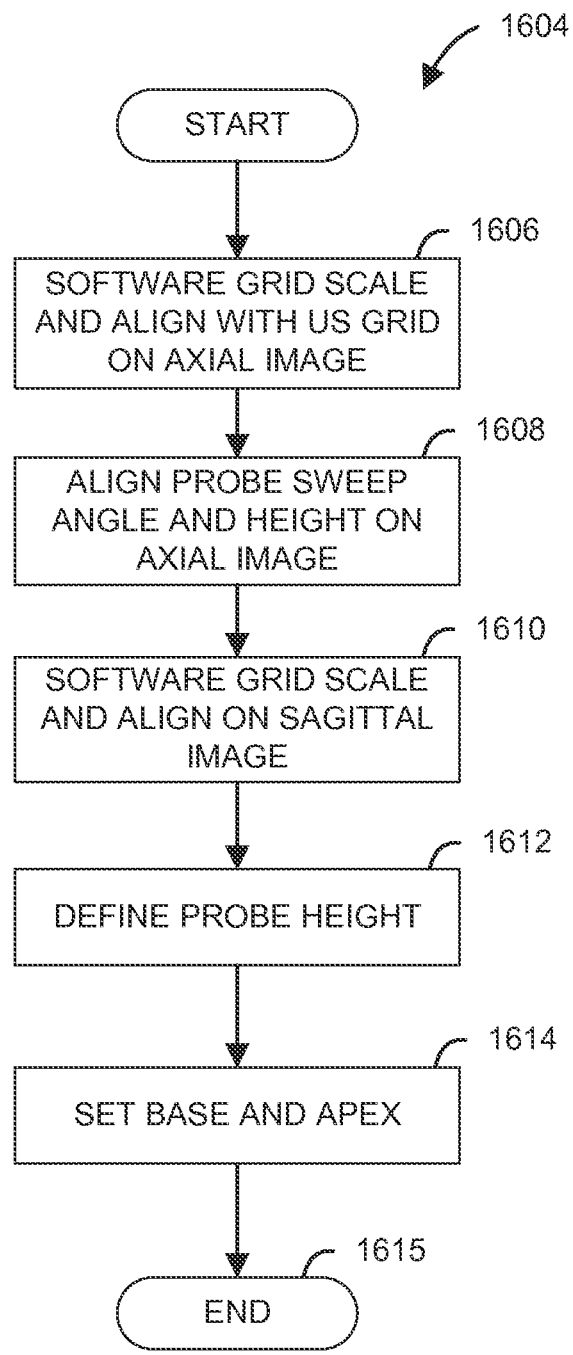
FIG. 76 is a diagram of a process of image acquisition according to some embodiments of the disclosed subject matter.

FIG. 75 depicts and exemplary embodiment of the process 1602 of planning a biopsy procedure according to some embodiments of the disclosed subject matter. An image is acquired at step 1604. FIG. 76 depicts an exemplary embodiment of the image acquisition process 1604. The software grid and scale are aligned with the ultrasound gird on an axial view of the image at step 1606. The ultrasound probe sweep angle and height are aligned with the axial view of the image at step 1608. The software grid and scale are aligned with a sagittal view of the image at step 1610. The ultrasound probe height is aligned with the sagittal view of the image at step 1612. And the base and apex of the prostate are marked at step 1614. The image acquisition process ends at step 1615.

Figure 77:
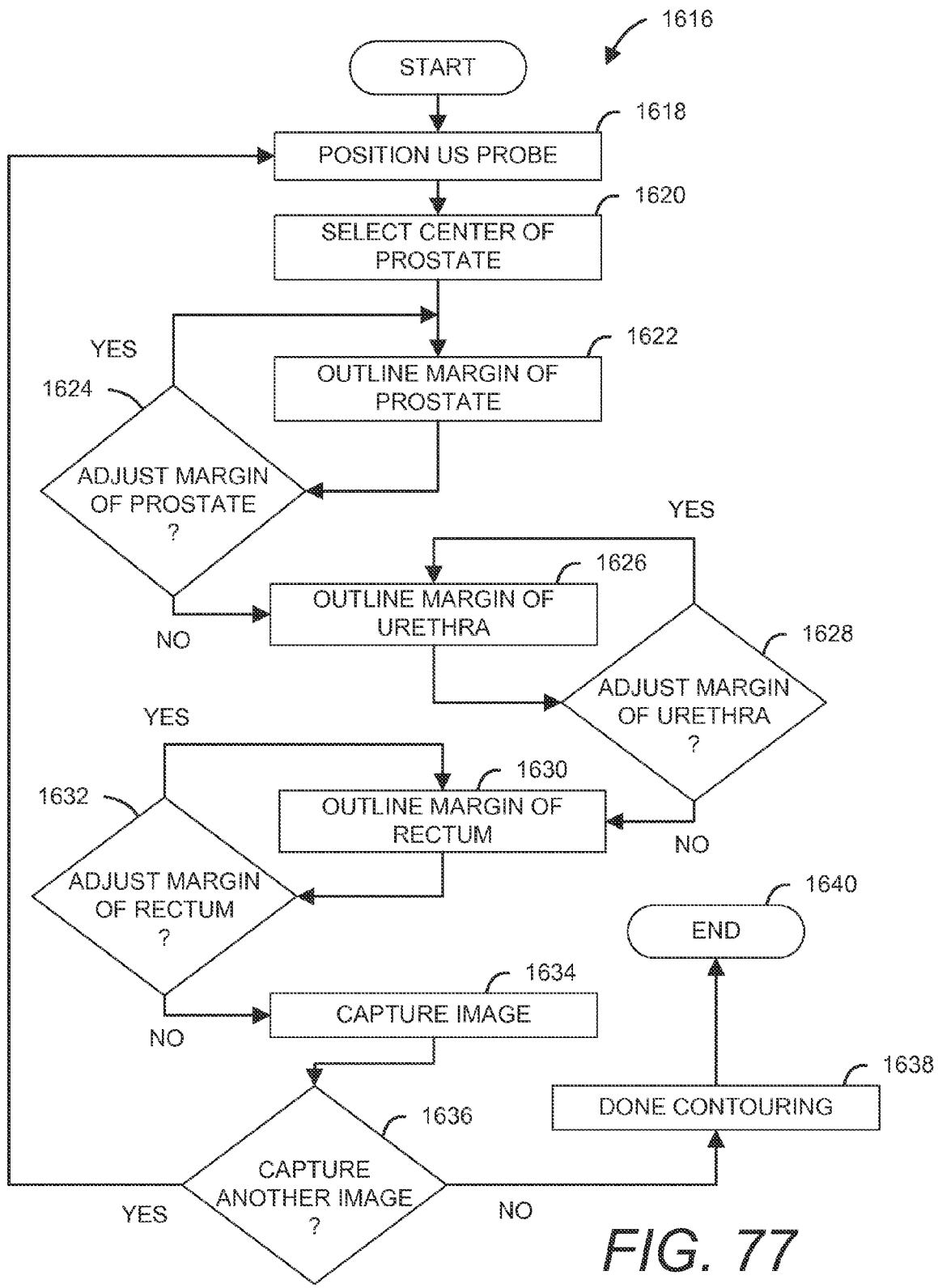
FIG. 77 is a diagram of a process of contouring images according to some embodiments of the disclosed subject matter.

The image is contoured at step 1616. FIG. 77 depicts an exemplary embodiment of the image contouring process 1616. The ultrasound probe is positioned at step 1618. The center of the prostate is selected at step 1620. The margin of the prostate is outlined at step 1622. The next step is determined at step 1624. Step 1622 may be repeated to refine the margin of the prostate. The margin of the urethra is outlined at step 1626. The next step is determined at step 1628. Step 1626 may be repeated to refine the margin of the urethra. The margin of the rectum is outlined at step 1630. The next step is determined at step 1632. Step 1630 may be repeated to refine the margin of the rectum. The contour image is captured at step 1634 creating an image slice. The next step is determined at step 1636. Steps 1618-1634 may be repeated to contour another image slice. Contouring is completed at step 1638. The contouring process ends at step 1640.

A three-dimensional image of the prostate, urethra, and rectum are generated from the image slices and aligned with the image at step 1642.

Figure 78:
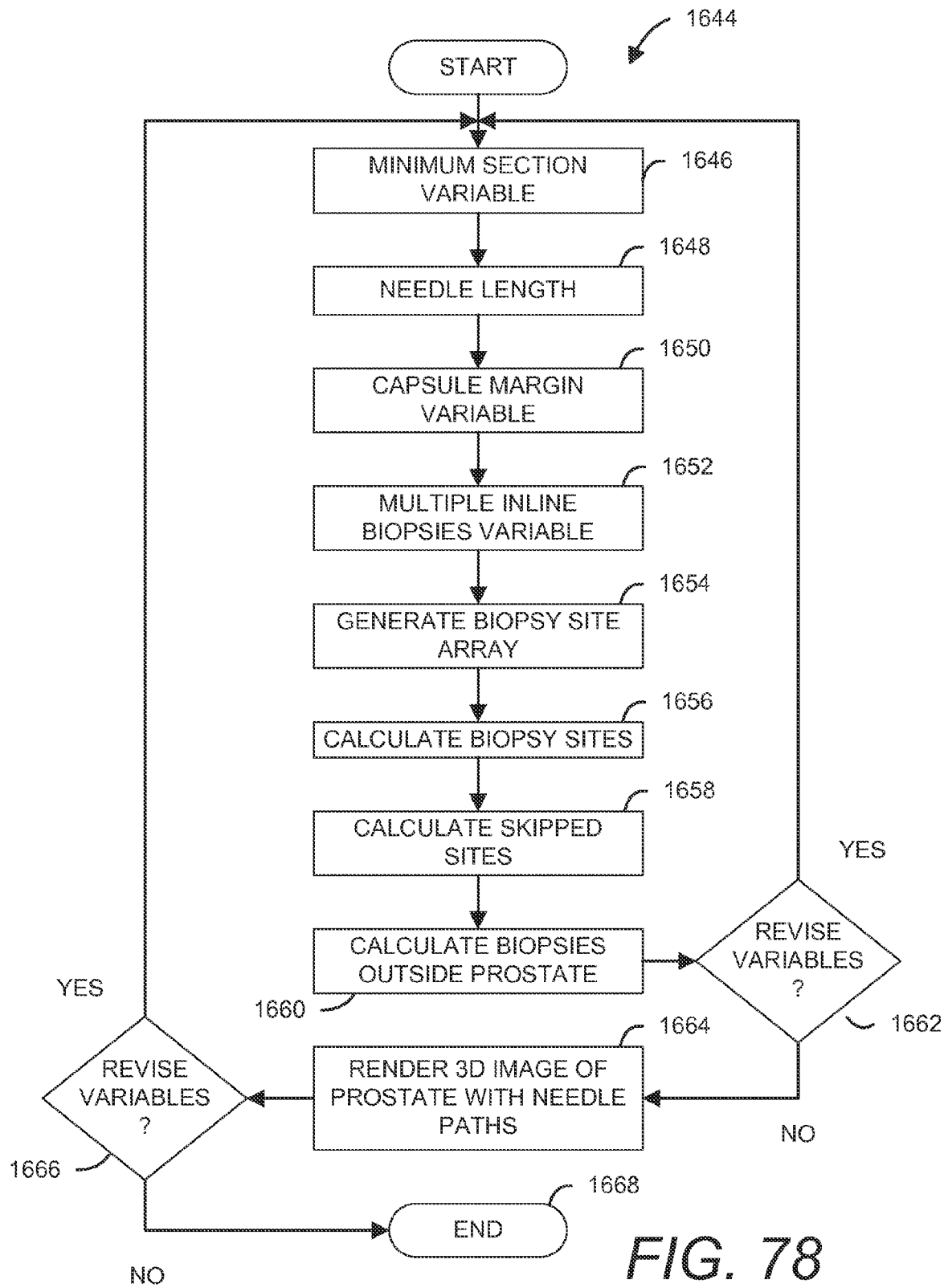
FIG. 78 is a diagram of a process of planning a biopsy site according to some embodiments of the disclosed subject matter.

The biopsy site plan process is created at step 1644. FIG. 78 depicts an exemplary embodiment of the biopsy site plan process 1644. The minimum section variable is selected at step 1646. The needle lengths are calculated at step 1648. The capsule margin variables are selected at step 1650. The multiple inline biopsy variables are determined at step 1652. The biopsy site array is generated at step 1654. The number of biopsy sites are calculated at step 1656. The number of skipped biopsy sites is calculated at step 1658. The number of biopsies that are outside the prostate are calculated at step 1660. The next step is determined at step 1662. Steps 1646-1660 may be repeated to modify the number of biopsy sites and their associated characteristics. A three-dimensional image of the prostate, urethra, and rectum with the biopsy needle paths is generated from the image slices and the biopsy site plan at step 1664. The next step is determined at step 1666. Steps 1646-1664 may be repeated to modify the number of biopsy sites and their associated characteristics. The biopsy site plan process ends at step 1668. The biopsy planning procedure ends at step 1670.

Figure 79:
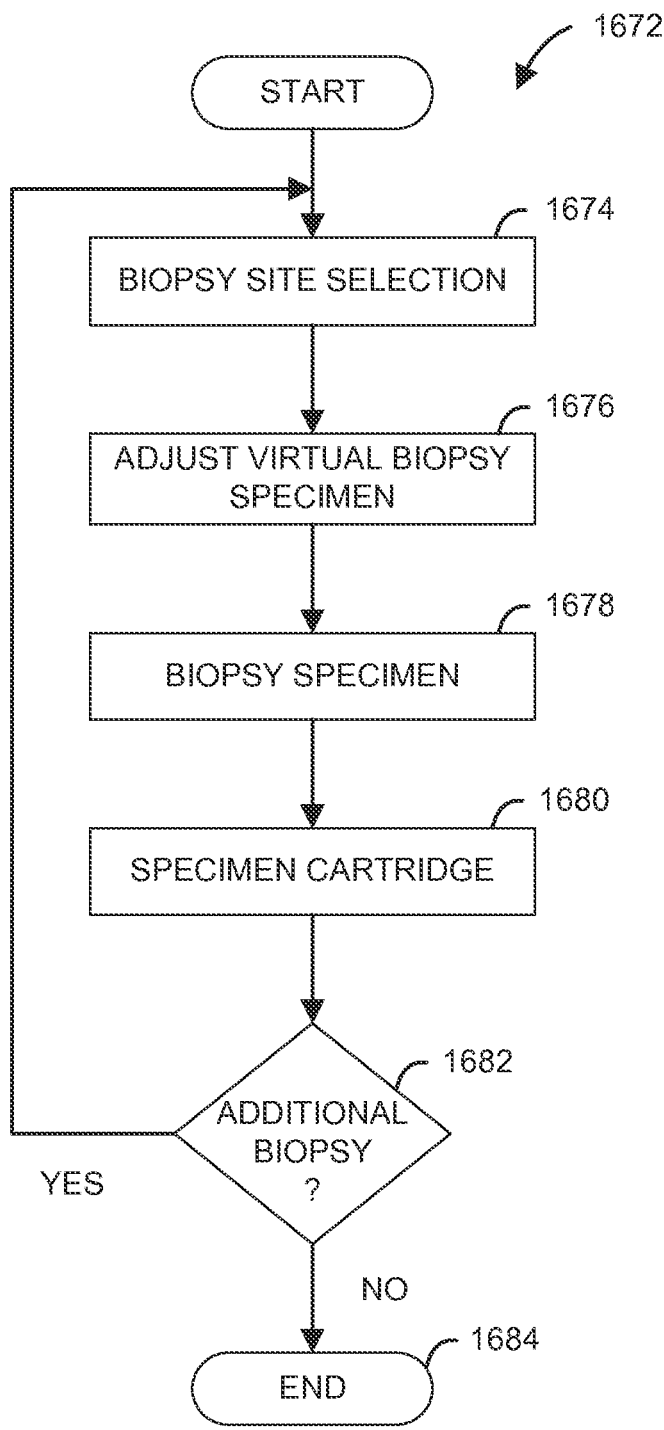
FIG. 79 is a diagram of a process of acquiring biopsy tissue specimens according to some embodiments of the disclosed subject matter.

FIG. 79 depicts an exemplary embodiment of the biopsy process 1672. A biopsy site is selected at step 1674. The virtual biopsy specimen location and length is adjusted on the image at step 1676. The biopsy specimen is taken at step 1678. The biopsy specimen is deposited in a specimen cartridge at step 1680. The next step is determined at step 1682. Steps 1674-1680 may be repeated to take additional biopsy specimens. The biopsy process ends at step 1684.

Figure 80:
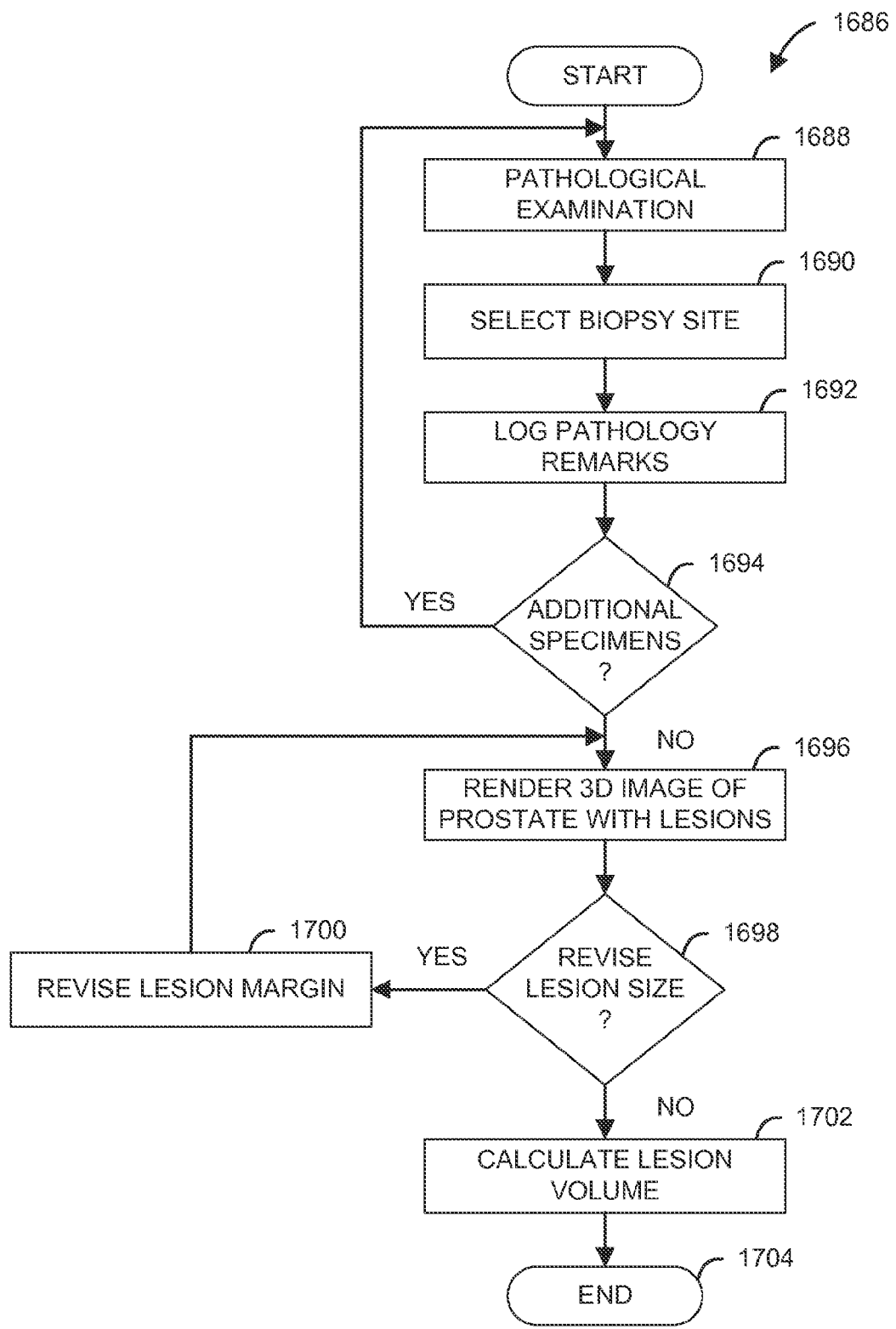
FIG. 80 is a diagram of a process of examining tissue specimens according to some embodiments of the disclosed subject matter.

FIG. 80 depicts an exemplary embodiment of the pathology process 1686. A biopsy specimen is selected and examined at step 1688. The biopsy site associated with the biopsy specimen is selected at step 1690. Remarks of the pathological findings of the examination, such as lesions, are entered into the system at step 1692. The next step is determined at step 1694. Steps 1688-1692 may be repeated to examine additional biopsy specimens. A three-dimensional image of the prostate, urethra, and rectum with lesions is generated from the image slices and the pathological findings at step 1696. The next step is determined at step 1698. Step 1700 may be repeated to adjust the margins of the lesions. The volume of the tissue lesions is calculated at step 1702. The pathology process ends at step 1704.

Figure 81:
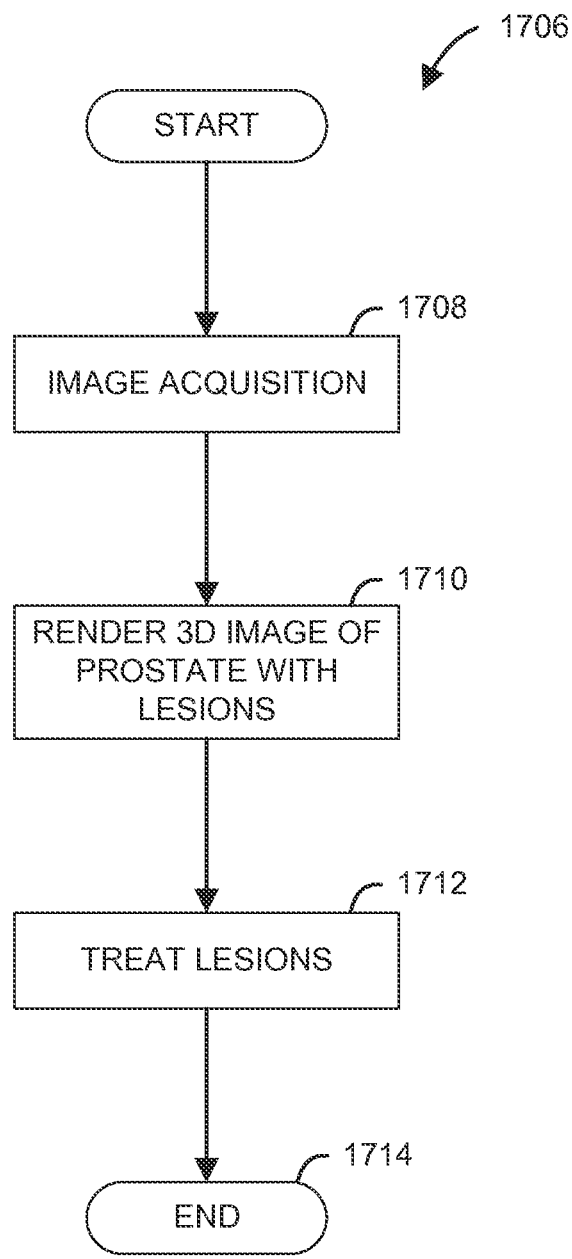
FIG. 81 is a diagram of a process of treating lesions according to some embodiments of the disclosed subject matter.

FIG. 81 depicts an exemplary embodiment of the treatment process 1706. The image is acquired at step 1708. The three-dimensional image of the prostate, urethra, and rectum with lesions is aligned with the image at step 1710. The lesions are treated at step 1712. The treatment process ends at step 1714.

Exemplary Hardware Configuration

Figure 82:
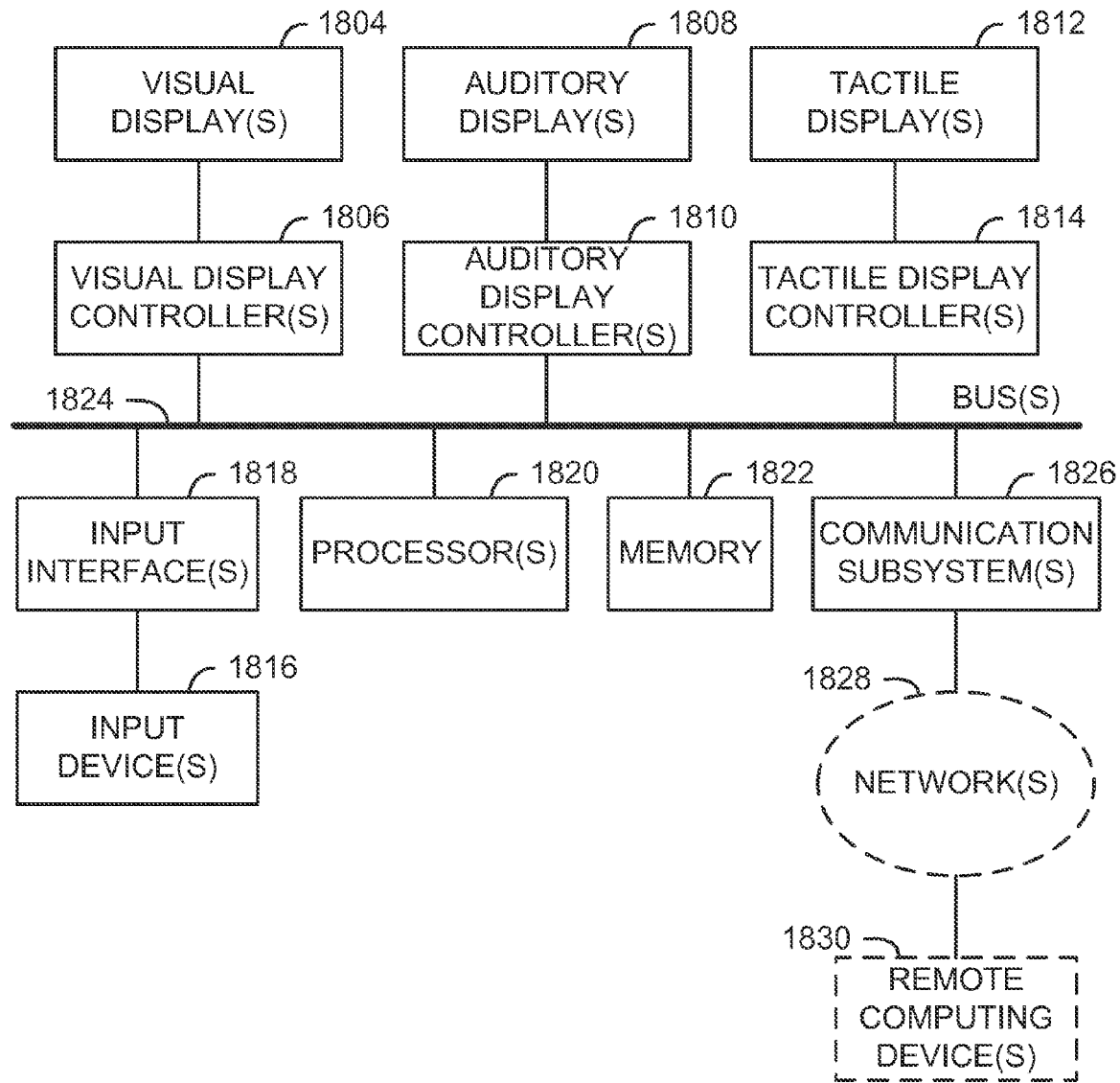
FIG. 82 is a block diagram of an exemplary hardware configuration model for a device implementing the system described in reference to FIGS. 33-81.

FIG. 82 is a block diagram of an exemplary hardware configuration model for a device implementing the system 1102 described in reference to FIGS. 33-81.

Some embodiments of the above-described systems and methods are implemented as software processes that are specified as a set of instructions recorded on a computer readable medium. When the instructions are executed by one or more computational element(s), the instructions cause the computational element(s) to perform the actions indicated by the instructions. The software processes function with common operating systems, including systems provided by Microsoft Corporation of Redmond, Wash., Apple Inc. of Cupertino, Calif., and International Business Machines Corporation of Armonk, N.Y.

The device can include one or more visual display(s) 1804 coupled with one or more visual display controller(s) 1806, one or more auditory display(s) 1808 coupled with one or more auditory display controller(s) 1810, and one or more tactile display(s) 1812 coupled with one or more tactile display controller(s) 1814. It can include one or more input devices 1816 for the input of data, information, and instructions into the system 1102 including, alphanumeric and other keys, a cursor control such as a mouse, trackball, or cursor direction keys, and any number of input structures existing in various forms including sensors, buttons, switches, control pad, stylus, wheel, camera, proximity sensor and/or motion sensing technologies, each coupled to one or more input interfaces 1818.

The device can include one or more computational elements, including processor(s) 1820 and one or more computer readable media, including memory bank(s) 1822 connected to one another and connected to the various display controller(s) and input interface(s) via one or more bus(ses) 1824. It can also be coupled with one or more communication subsystem(s) 1826 that communicate through one or more network(s) 1828 to one or more remote computing device(s) 217.

The one or more communication subsystems(s) 1826 may provide additional data channels for receiving and transmitting data, information, or instructions. The communication subsystem(s) 1826 may include one or more network interface hardware elements and associated communication protocols. The communication subsystem(s) 1826 provides two-way data communication to a network 1828. The communication subsystem(s) 1826 may include several types of systems, including a wireless carrier system, a wireless local area network (WLAN) system, an unstructured supplementary service data (USDD) system, a personal area network (PAN) system, a local area network (LAN) system, and a wide area network (WAN) system. The system 1102 may execute one or more sequences of one or more instructions or user data contained in one or more computer readable media connected to the network 1828. The network 1828 felicitates communication between the system 1102 and any other local or remote computer devices 1830, including third party computer devices, computer readable media, databases, servers, or web servers. The network 1820 can be all or a portion of a distributed or secure network, or a wireless or wired network.

The device may be powered by a suitable power source that may include one or more batteries or an AC power source, such as provided by an electrical outlet.

The term "computer" means a device or system with at least one microprocessor. Examples of computers include laptop computers, tablet computers, mobile phones, digital media players, game consoles, digital wristwatches, head-mounted display systems, digital televisions, set-top boxes and file servers. The term "device" is meant to be interchangeable with the term computer where it is clear from the context that the reference is to a computer as defined herein (i.e. with at least one microprocessor).

The terms "computer readable medium" and "computer readable media" can be used interchangeably to mean storage that can be accessed by a computer. These terms include non-volatile memory such as a dynamic storage device, random-access memory (RAM), read-only memory (ROM), flash memory, a hard drive, database, or any other suitable non-transitory computer-readable media, such as optical, magnetic, or solid-state computer readable media, as well as a combination thereof, provided that neither term is intended to include any propagated signal, any carrier wave or any other non-statutory subject matter.

The noun "display" means an output device for conveying information to a user, including visual display hardware (such as a cathode ray tube (CRT), a liquid crystal display (LCD), a light emitting diode (LED) display, an organic light emitting diode (OLED) display, an image projector, or other suitable display), auditory display hardware (such as speakers and headphones), tactile display hardware (such as braille and textural haptics, piezoelectric vibration motors and force-feedback systems) and other sensory displays. The visual display hardware, such as the visual display 1804, may include touch-sensitive functionality, such as a touch screen. The visual display hardware displays the graphical user interface 1104 that allows a user to interact with the system 1102. The graphical user interface 1024 may include various screens, layers, windows, images, elements, or components.

The invention claimed is:

1. A biopsy needle actuator device, comprising:
   an actuator moving a biopsy needle between a rest position and a first position;
   an engagement member operably connected to the actuator;
   a counter assembly operably connected to the needle actuator device registering movement of the biopsy needle between the rest position and the first position, comprising:
   a register wheel with a toothed exterior wherein the engagement member engages the toothed exterior upon movement of the biopsy needle between the rest position and the first position; and
   an index wheel operably connected to the register wheel registering rotational movement of the register wheel, comprising:
   an event counter sequentially registering movement of the biopsy needle between the rest position and the first position; and
   a cumulative counter sequentially registering cumulative movement of the biopsy needle between the rest position and the first position; and
   a button configured to adjust the event counter.

2. The actuator device of claim 1, further comprising a bypass button adapted for allowing movement of the biopsy needle between the rest position and the first position without advancing the counter assembly.

3. The actuator device of claim 1, further comprising a mechanical lockout that prevents movement of the biopsy needle when the cumulative counter registers a defined number of movements of the biopsy needle between the rest position and the first position.

4. The actuator device of claim 1, wherein the register wheel registers movement of the biopsy needle as the biopsy needle is moved from the rest position to the first position.

5. The actuator device of claim 1, wherein the biopsy needle is a cannula.

6. The actuator device of claim 1, further comprising a bubble level assembly.

7. A biopsy needle actuator device, comprising:
- an actuator moving a biopsy needle between a rest position and a first position; and
- a counter assembly operably connected to the actuator registering movement of the biopsy needle between the rest position and the first position, the counter assembly comprising:
- an event counter sequentially registering movement of the biopsy needle between the rest position and the first position; and
- a cumulative event counter sequentially registering cumulative movement of the biopsy needle between the rest position and the first position; and
- a bypass button adapted to allow movement of the biopsy needle between the rest position and the first position without advancing the counter assembly.

8. The actuator device of claim 7, further comprising:
- an index wheel operably connected to the event counter and cumulative event counter registering movement of the biopsy needle between the rest position and the first position; and
- wherein rotational movement of the index wheel sequentially advances each of the event counter and cumulative event counter one whole number.

9. The actuator device of claim 8, further comprising:
- an engagement member connected to the actuator engaging and rotating the index wheel.

10. The actuator device of claim 9, further comprising:
- a biasing member connected to the engagement member;
- wherein the index wheel is spaced apart from the actuator;
- wherein the engagement member extends rearward and upward from the actuator toward the index wheel when the actuator is at the rest position; and
- wherein the biasing member allows the engagement member to move away from the index wheel as the biopsy needle moves from the first position to the rest position.

11. The actuator device of claim 7, wherein the biopsy needle is a cannula.

12. The actuator device of claim 7, further comprising a bubble level assembly.

13. A biopsy needle actuator device, comprising:
- an actuator moving a biopsy needle between a rest position and a first position; and
- a counter assembly operably connected to the actuator for registering movement of the biopsy needle between the rest position and the first position, the counter assembly comprising:
- an event counter for sequentially registering movement of the biopsy needle between the rest position and the first position;
- a cumulative event counter for sequentially registering cumulative movement of the biopsy needle between the rest position and the first position;
- an index wheel operably connected to the event counter and cumulative event counter for registering movement of the biopsy needle between the rest position and the first position; and
- wherein rotational movement of the index wheel sequentially advances each of the event counter and cumulative event counter one whole number;
- an engagement member connected to the actuator for engaging and rotating the index wheel;
- a biasing member connected to the engagement member;
- wherein the index wheel is spaced apart from the actuator;
- wherein the engagement member extends rearward and upward from the actuator toward the index wheel when the actuator is at the rest position; and
- wherein the biasing member allows the engagement member to move away from the index wheel as the biopsy needle moves from the first position to the rest position.

14. The actuator device of claim 13, wherein the biopsy needle is a cannula.

15. The actuator device of claim 13, further comprises a bubble level assembly.

* * * * *